US007928205B2

(12) United States Patent
Dillon et al.

(10) Patent No.: US 7,928,205 B2
(45) Date of Patent: Apr. 19, 2011

(54) METHODS FOR REFOLDING OF RECOMBINANT ANTIBODIES

(75) Inventors: Thomas M. Dillon, Ventura, CA (US); Douglas Rehder, Phoenix, AZ (US); Pavel Bondarenko, Thousand Oaks, CA (US); Margaret Ricci, Camarillo, CA (US); Himanshu S. Gadgil, Seattle, WA (US); Douglas D. Banks, Bainbridge Island, WA (US); Joe Zhou, Shanghai (CN); Yuefeng Lu, Newbury Park, CA (US); Andrew Goetze, Newbury Park, CA (US); Yuling Zhang, Redmond, WA (US)

(73) Assignee: Amgen Inc., Thousand Oaks, CA (US)

( * ) Notice: Subject to any disclaimer, the term of this patent is extended or adjusted under 35 U.S.C. 154(b) by 479 days.

(21) Appl. No.: 11/255,528

(22) Filed: Oct. 21, 2005

(65) Prior Publication Data

US 2006/0194280 A1    Aug. 31, 2006

Related U.S. Application Data

(60) Provisional application No. 60/621,295, filed on Oct. 22, 2004, provisional application No. 60/701,762, filed on Jul. 22, 2005.

(51) Int. Cl.
*A61K 39/395* (2006.01)
*C07K 16/00* (2006.01)
(52) U.S. Cl. ............... 530/390.5; 424/177.1; 435/69.6; 530/408
(58) Field of Classification Search .................... None
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,737,323 A | 4/1988 | Martin et al. | |
| 4,745,051 A | 5/1988 | Smith et al. | |
| 4,766,205 A | 8/1988 | Ghosh-Dastidar | |
| 4,816,397 A | 3/1989 | Boss et al. | |
| 4,816,567 A | 3/1989 | Cabilly et al. | |
| 4,837,028 A | 6/1989 | Allen | |
| 4,870,009 A | 9/1989 | Evans et al. | |
| 4,952,496 A | 8/1990 | Studier et al. | |
| 5,169,784 A | 12/1992 | Summers et al. | |
| 5,225,539 A | 7/1993 | Winter | |
| 5,242,687 A | 9/1993 | Tykocinski et al. | |
| 5,243,041 A | 9/1993 | Fernandez-Pol | |
| 5,266,317 A | 11/1993 | Tomalski et al. | |
| 5,272,071 A | 12/1993 | Chappel | |
| 6,036,978 A | 3/2000 | Gombotz et al. | |
| 6,063,905 A * | 5/2000 | Capra et al. | 530/387.3 |
| 7,157,557 B2 * | 1/2007 | Sassenfeld et al. | 530/350 |
| 2002/0182665 A1* | 12/2002 | Sassenfeld et al. | 435/68.1 |
| 2003/0023586 A1 | 1/2003 | Knorr | |
| 2003/0138421 A1 | 7/2003 | van de Winkel et al. | |
| 2004/0071702 A1 | 4/2004 | van de Winkel et al. | |
| 2005/0101016 A1 | 5/2005 | McIntyre | |
| 2005/0260681 A1 | 11/2005 | McIntyre | |
| 2007/0082367 A1* | 4/2007 | Godavarti et al. | 435/7.2 |

FOREIGN PATENT DOCUMENTS

| | | |
|---|---|---|
| CA | 2066370 | 4/1996 |
| EP | 0 120 694 | 10/1984 |
| EP | 0 125 023 | 11/1984 |
| EP | 0 194 276 | 9/1986 |
| EP | 0 239 400 | 9/1987 |
| EP | 0 293 785 | 12/1988 |
| EP | 0 451 216 | 10/1991 |
| EP | 0510658 | 10/1992 |
| EP | 0 519 596 | 12/1992 |
| EP | 0 553 494 | 8/1993 |
| WO | WO-86/01533 | 3/1986 |
| WO | WO-93/08207 | 4/1993 |
| WO | WO-94/22902 | 10/1994 |
| WO | WO-95/32216 | 11/1995 |
| WO | WO-96/03141 | 2/1996 |
| WO | WO-96/40918 | 12/1996 |
| WO | WO-01/34638 | 5/2001 |
| WO | WO-01/49720 | 7/2001 |
| WO | WO-02/068455 | 9/2002 |
| WO | WO-02/072636 | 9/2002 |
| WO | WO-03/000014 | 1/2003 |
| WO | WO-2005/073732 | 8/2005 |

OTHER PUBLICATIONS

Zhang et al., BioProcessing Journal, p. 37-43 (2003).
International Search Report for PCT/US05/38045 issued on Apr. 20, 2007.
Zhang et al., Biotechnol. Prog., 18:509-513 (2002).
Aalberse et al., Immunology, 105:9-19 (2002).
Angel et al., Mol. Immunol., 30(1):105-108 (1993).
Bondarenko et al., Int. J. Mass Spectrom., 219:671-680 (2002).
Brasel et al., Blood, 88(6):2004-2012 (1996).
Buchner et al., Biochemistry, 30:6922-6929 (1991).
Buchner et al., J. Mol. Biol., 318:829-836 (2002).
Buchwald, Can. J. Biochem., 49:900-902 (1971).
Chaderjian et al., Biotechnol. Prog., 21:550-553 (2005).
Chaudhary et al., Nature, 339:394-397 (1989).
Chowdhury et al., Anal. Chem., 63:1660-1664 (1991).
Cohen, Annu. Rev. Biochem., 37:695-726 (1968).
Craescu et al., J. Biol. Chem., 261(31):14710-14716 (1986).
Creighton, Methods Enzymol., 107:305-329 (1984).
Davis et at., Biochemistry, 35:2482-2488 (1996).
Dillon et al., J. Chromatogr. A, 1053:299-305 (2004).
Dobo et al., Anal. Chem., 73(20):4763-4773 (2001).
Dormann et al., J. Biol. Chem., 268(22):16286-16292 (1993).
Fenn, J. Am. Soc. Mass. Specrom., 4:524-535 (1993).
Gregory et al., Mol. Immunol., 24(8):821-829 (1987).
Harris et al., J. Mol. Biol., 275(5):861-872 (1998).
Harris et al., Nature, 360:369-372 (1992).

(Continued)

*Primary Examiner* — David A Saunders
(74) *Attorney, Agent, or Firm* — Charles K. Sholtz

(57) ABSTRACT

The present invention is generally directed to methods of producing an increase in the enrichment or recovery of preferred forms of IgG proteins. More particularly, the invention relates to subjecting preparations of such recombinant IgG proteins with a reduction/oxidation coupling reagent and optionally a chaotropic agent.

44 Claims, 52 Drawing Sheets

OTHER PUBLICATIONS

Houee-Levin, Methods Enzymol., 353:35-44 (2002).
Houry et al., Nature, 402:147-154 (1999).
Hulett et al., Adv. Immunol., 57:1-127 (1994).
Jefferis et al., Immunol. Lett., 82:57-65 (2002).
Josic et al., Food Technol. Biotechnol., 39(3):215-226 (2001).
Kaufman et al., J. Biol. Chem., 263(13):6352-6362 (1988).
Keown et al., Methods Enzymol., 185:527-537 (1990).
Kuwajima, Proteins, 6:87-103 (1989).
Larrick et al., Biotechnology, 7:934-938 (1989).
Larson et al., J. Mol. Biol., 222:17-19 (1991).
Lilie et al., Curr. Opin. Biotechnol., 9:497-501 (1998).
Lilie et al., FEBS Lett., 362:43-46 (1995).
Lilie et al., J. Mol. Biol., 248:190-201 (1995).
Lilie et al., Protein Sci., 2:1490-1496 (1993).
Lilie et al., Protein Sci., 4:917-924 (1995).
Lim et al., Anal. Biochem., 295:45-56 (2001).
McKinnon et al., J. Mol. Endocrinol., 6:231-239 (1991).
Middelberg, Trends Biotechnol., 20(10):437-443 (2002).
Nakamura et al., Cell, 18:1109-1117 (1979).
Pace, Methods Enzymol., 131:266-280 (1986).
Perczel et al., Protein Eng., 4(6):669-679 (1991).
Phillips et al., Mol. Immunol., 31(15):1201-1210 (1994).
Ptitsyn et al., FEBS Lett., 262(1):20-24 (1990).
Rattenholl et al., Eur. J. Biochem., 268:3296-3303 (2001).
Riechmann et al., Nature, 332:323-327 (1988).
Ritz et al., Annu. Rev. Microbiol., 55:21-48 (2001).
Roberts et al., Nature, 328:731-734 (1987).
Rudolph et al., FASEB J., 10:49-56 (1996).
Saphire et al., J. Mol. Biol., 319:9-18 (2002).
Saphire et al., Science, 293:1155-1159 (2001).
Schauenstein et al., Int. Arch. Allergy Appl. Immunol., 80:174-179 (1986).
Schuurman et al., Immunology, 97:693-698 (1999).
Schuurman et al., Mol. Immunol., 38(1):1-8 (2001).
Seefeldt et al., Protein Sci., 13:2639-2650 (2004).
Segal et al., Proc. Natl. Acad. Sci. USA, 96:2758-2763 (1999).
St. John et al., Proc. Natl. Acad. Sci. USA, 96(23):13029-13033 (1999).
Studier et al., Methods Enzymol., 185:60-89 (1990).
Turner et al., Biochem. J., 107:171-178 (1968).
Umetsu et al., J. Biol. Chem., 278(11):8979-8987 (2003).
Urlaub et al., Proc. Natl. Acad. Sci. USA, 77(7):4216-4220 (1980).
Verhoeyen et al., Science, 239(4847):1534-1536 (1988).
von Heijne, J. Mol. Biol., 184:99-105 (1985).
Welfle et al., Biochim. Biophys. Acta, 1431:120-131 (1999).
Wood et al., J. Immunol., 145(9):3011-3016 (1990).
Wunderlich et al., J. Biol. Chem., 268(33):24547-24550 (1993).
Yoo et al., J. Immunol., 170:3134-3138 (2003).
Dillon et al., Structural and functional characterization of disulfide isoforms of the human IgG2 subclass. *J. Biol. Chem.* 283(23):16206-15 (2008).
Banks et al., Removal of cysteinylation from an unpaired sulfhydryl in the variable region of a recombinant monoclonal IgG1 antibody improves homogeneity, stability, and biological activity. *J. Pharmaceut. Sci.* 97(2): 764-9 (2008).
Guo et al., Electrophoretic evidence for the presence of structural isoforms specific for the IgG2 isotype. *Electrophoresis.* 29: 2550-6 (2008).
McIntyre et al., Panitumumab. Oncolytic—anti-EGFR human monoclonal antibody. *Drugs of the Future.* 29(8): 793-7 (2004).
Supplementary European Search Report, EP 05 81 1874, dated Aug. 10, 2009.

* cited by examiner

METHODS FOR REFOLDING OF RECOMBINANT ANTIBODIES

The present application claims the benefit of priority of U.S. Provisional Application 60/621,295 filed Oct. 22, 2004 and U.S. Provisional Application 60/701,762 filed Jul. 22, 2005. Each of the aforementioned applications is specifically incorporated herein by reference in its entirety.

BACKGROUND

1. Field of the Invention

The present invention is generally directed to methods of producing an increase in the enrichment and/or recovery of preferred forms of proteins. More particularly, the invention relates to methods for refolding recombinant antibody proteins.

2. Background of the Related Art

The advent of genetic engineering brought with it the promise of facile production of large quantities of biologically relevant polypeptides expressed in functional form in genetically-engineered organisms. In many instances, prokaryotes have been contemplated for use to achieve the expression of recombinant proteins. However, this promise has not been fully realized for a number of reasons. For example, in many instances where the polypeptide has been produced and retained in the cytoplasm of the host organism, inclusion bodies have resulted requiring denaturation and renaturation of the protein, frequently with only partial or little success. Many important target proteins are at best inefficiently expressed in soluble form in prokaryotic cells, due at least in part to the complexity of the protein folding process in vivo (Houry et al., Nature, 402: 147-154, 1999). Retrieval of the biologically active eukaryotic proteins from the inclusion bodies requires unfolding and refolding of the protein through the use of harsh conditions which include the use of chaotropic agents and reducing thiols. In other instances, the expressed protein or peptide is substantially degraded, not only leading to low yields but also generating complicated mixtures that are difficult to separate and purify.

Disulfide bond formation in proteins in vivo is a complex process, which is determined by the redox potential of the environment and specialized thiol-disulfide exchanging enzymes (Creighton, *Methods Enzymol.* 107, 305-329, 1984; Houee-Levin, *Methods Enzymol.* 353, 35-44, 2002; Ritz and Beckwith, Roles of thiol-redox pathways in bacteria, *Annu. Rev. Microbiol.* 55, 21-48, 2001.) The disulfides are formed in cells during or shortly after secretion of the nascent chains into the endoplasmic reticulum (Creighton, *Methods Enzymol.* 107, 305-329, 1984). Several conformational isoforms of the same protein, but with different disulfide structures, can be generated during recombinant protein production in mammalian cells due to the failing disulfide formation process, close proximity of three or more cysteine residues in the protein structure or surface exposure of unpaired cysteine residues.

In general, cysteine residues in proteins (including antibodies, IgG antibodies, IgG1 antibodies and the IgG1 antibody binding human IL-15) are either engaged in cysteine-cysteine disulfide bonds or sterically protected from the disulfide bond formation when they are a part of folded protein region. When a cysteine residue does not have a pair in protein structure and is not sterically protected by folding, it can form a disulfide bond with a free cysteine from solution (cysteinylation). The free cysteine residues are typically available in fermentation media together with other amino acids, building blocks of the proteins. The cysteinylation is undesirable posttranslational modification in pharmaceutical proteins, which may lead to a conformational isoform with undesirable properties, such as low binding, low biological activity and low stability. This invention provides method for removing the cysteinylation and increasing relative abundance of the desired conformational isoform without cysteinylation.

Unpaired cysteine residues in proteins can be subjected to cysteinylation, which can lead to significant changes in properties and function of the proteins. Cysteinylation of proteins was reported on proteins in vivo (Craescu et al., J. Biol. Chem. 261, 14710-14716, 1986; Dormann et al., J. Biol. Chem. 1993, 268, 16286-16292; Davis et al., Biochemistry 1996, 35, 2482-2488; Lim et al., Anal. Biochem. 2001, 295, 45-56, Bondarenko et al., Int. J. Mass Spectrom. Ion Processes 2002, 219, 671-680.) Modifications of cysteine residue modulated protein activity. For example, covalent binding of glutathione to hemoglobin increases the oxygen-binding properties of this protein (Craescu et al., J. Biol. Chem. 261, 14710-14716, 1986). In another example, liver type fatty acid-binding proteins (LABP) lost binding affinity after cysteinylation and glutathionylation (Dormann et al., J. Biol. Chem. 1993, 268, 16286-16292). HIV-1 protease activity was regulated through cysteinylation and glutathionylation (Davis et al., Biochemistry 1996, 35, 2482-2488). There are reports that there is a fraction of human antibodies in circulation that possesses an unpaired cysteine. For example, in one report it is shown that an immunoglobulin light chain of lambda type possesses a free cysteine in position 33, such that the light chain possesses a total of six cysteine residues (Buchwald et al., Can. J. Biochem. 1971, 49, 900-902). It was indicated that this free cysteine is a feature of a subgroup III of lambda light chains.

Although unpaired cysteines have been reported in IgG molecules there are no reported cases of cysteinylation of unpaired cysteins. Detection of cysteinylation can be analytically challenging and the failure to observe cysteinylation in earlier report could be due to the use of reduction in one of the steps in the analysis (reduction will eliminate cysteinylation). Cysteinylation when present in the CDR region can affect the biological activity as is seen in the case of 146B7, a fully human antibody directed against human IL-15. Removal of cysteinylation by refolding helps in minimizing heterogeneity hence improving product homogeneity. Removal of cysteinylation by refolding also increased product efficacy. There is a good chance that cysteinylation will be present on other IgG molecules containing one or more unpaired cysteines and removal of the cysteinylation could be the key for pharmaceutical viability of such products.

PCT Publication No. WO 02/68455 discloses a process for refolding a tumor necrosis factor receptor Fc fusion protein. The protein was bioengineered by fusing Fc region of IgG1 antibody and two tumor necrosis factor receptors (TNFr) and does not occur naturally. The document does not address proteins that have heterogeneous structures due to the presence of at least one free or unpaired cysteine, i.e., a cysteine that is not participating in a disulfide bond. Complex proteins bearing free cysteines are known to exist and at least some immunoglobulins are commercially relevant example of such proteins. In particular, it is noteworthy that WO 02/68455 provides no examples of processing of naturally occurring molecules such as immunoglobulins, nor does it discuss or address protein-folding problems of large complex proteins that contain free or unpaired cysteines.

In vitro folding of inclusion body proteins produced by microbial cells (*E. coli*) is well described in the literature and includes two steps. First, the inclusion body proteins are solubilized in a presence of high concentration of a chaotropic reagent and reducing reagent to break all disulfide bonds (Middelberg, A. P. Preparative protein refolding. *Trends Biotechnol.* 2002, 20, 437-443). For example, an inclusion body solubilization solution includes 6 M guanidine hydrochloride and 100 mM DTT in a review by Rudolph, R.; Lilie, H. In vitro folding of inclusion body proteins. *FASEB J.* 1996, 10, 49-56. The second step is protein folding in presence of a moderate concentration of guanidine hydrochloride (0.5-1.0 M) and a mild redox environment (Middelberg, A. P. Preparative protein refolding. *Trends Biotechnol.* 2002, 20, 437-443). This invention does not include the step of solubilization by protein complete denaturation and reduction of all disulfide bonds in a presence of the high concentrations of chaotropic and reducing agents. The invented method does not denature the protein or denatures it only and reduces/oxidizes (reshuffles) only a few disulfides. This invention is dealing with proteins produces in mammalian cells. The production by mammalian cells includes in vivo protein folding and disulfide formation, while microbial cells produce proteins as a high density, unfolded, non-soluble proteins agglomerates with mixed disulfides (inclusion bodies). Because the mammalian cells link most of the disulfide bonds correctly, there no need for complete protein denaturation and reduction of all disulfide bonds.

U.S. Pat. No. 4,766,205 recognizes that recombinant production of proteins is hampered by the formation of inappropriate intramolecular disulfide bonds that lead to "non-native" conformations of the recombinant protein that are "frozen" in that they cannot readily be converted to the native conformation. Such non-native products are at least partially biologically inactive. To address this issue, U.S. Pat. No. 4,766,205 discloses a process that involves exposure of the protein to a reductant, addition of an adduct forming disulfide compound, followed by addition of an oxidant with the temporally coordinated removal of the reductant. The detailed description of the invention indicates that proteins are subjected to solubilization by complete denaturation and reduction of disulfide bonds. The number of steps involved and the number of compounds required render this approach cumbersome. It is noteworthy that U.S. Pat. No. 4,766,205 provides no discussion on the use of the disclosed process for refolding mammalian produced proteins, and large complex proteins that are formed by intermolecular bonding, such as immunoglobulins.

The above discussion shows that there remains a substantial need and interest in developing systems for the efficient and economic production, purification and analysis of active large polypeptides where the desired polypeptide has been produced, for example through recombinant means, such that the produced polypeptide is provided in an active conformation or conveniently processed and renatured to a functional state. Additionally, despite the fact that there are techniques that have been extensively used in the analysis of low molecular weight proteins such as insulin, or low molecular weight digests of larger proteins, there remains a need for additional methods and techniques for producing sequence and detailed conformational information about larger proteins, in particular, proteins having more than one subunits that are formed by intermolecular interaction. The present invention is directed at addressing these needs.

SUMMARY OF THE INVENTION

The present invention is directed to providing efficient and economic production, purification and analysis of active polypeptides that have proven refractory to existing methods of recombinant production due to the presence of scrambled disulfide bonds, and free or unpaired cysteine residue. More particularly, the invention describes methods of refolding proteins to produce improved pharmaceutical and crystallization properties. As described in further detail hereinbelow, the addition of reduction/oxidation (redox) coupling reagents can facilitate the formation of native-like disulfide bonds in the recombinant proteins and thus produce structurally homogeneous, more active forms of the molecule.

One aspect according to the invention provides a method of producing a recombinant IgG antibody, (e.g., an IgG1, and IgG2, an IgG3 or an IgG4 antibody) comprising: contacting a polypeptide that has been recombinantly produced by mammalian cells with a reduction/oxidation coupling reagent at a pH of about 5 to about 11. The method may optionally comprise contacting said preparation with a chaotropic agent before, after or concurrently with said contacting with said reduction/oxidation coupling reagent. In some embodiments, the polypeptide is a recombinant IgG1. More preferably, the IgG1 is an IgG1 having at least one free cysteine residue. An exemplary such antibody is the antibody designated as 146B7 in U.S. Publication Nos. 2003/0138421; 2003/023586; and 2004/0071702, all of which are incorporated by reference herein in their entireties. In other preferred embodiments, the IgG is an IgG2 molecule. Preferably, the method reduces the heterogeneity of the IgG2 molecule. Other embodiments involve methods of refolding IgG4 molecules to decrease the presence of IgG4 half molecules (referred to as "half-mers" herein).

Accordingly, the methods of the present invention are particularly directed to refolding recombinant forms of a IgG antibodies. An example of the production of such a IgG antibody is the production of a recombinant antibody by the recombinant expression of that antibody in CHO cells. An exemplary IgG1 antibody is described in the aforementioned U.S. Publications, 146B7 is a fully human antibody, i.e., IgG1, directed against human IL-15.

As noted above, certain embodiments of the invention provide a recombinant IgG1 antibody that has a free or unpaired cysteine residue. An antibody with an unpaired cysteine is understood to have one or more free cysteine residues, wherein a free cysteine residue is defined as an amino acid in the antibody polypeptide heavy chain or light chain that is not typically involved in the formation of a disulfide bond, but is proximal to a cysteine disulfide pair and if the disulfide bond of that pair is broken, the free cysteine is capable of forming a different disulfide bond with one of the previously paired cysteines. It is also understood that an antibody with a free cysteine may be capable of assuming more than one conformation depending on which cysteines are paired. It is also understood that antibody with a free cysteine may be capable of assuming more than one conformation depending if the cysteine residue is cysteinylated or glutathionelated.

Consistent with the foregoing, an aspect of the invention is drawn to a method of producing a recombinant IgG antibody, comprising: contacting a IgG molecule that has been recombinantly produced by mammalian cells with a reduction/oxidation coupling reagent at a pH of about 5 to about 11; and optionally further contacting the IgG molecule with a chaotropic agent before, after or concurrently with the contacting with the reduction/oxidation coupling reagent.

The methods thus comprise producing a preparation of such a recombinant IgG molecule, comprising contacting a preparation of the IgG molecule that has been recombinantly produced by mammalian cells (i.e., recombinant IgG) with a reduction/oxidation coupling reagent at a pH of about 5 to about 11; optionally, further contacting said preparation with a chaotropic agent before, after or concurrently with said contacting with said reduction/oxidation coupling reagent; and, optionally, isolating a fraction of the treated preparation of the recombinant IgG molecule wherein the IgG has refolded into a desired conformation. More specifically, the pH of the reduction/oxidation coupling reagent is from about 7 to about 10; further more specifically, the pH of the reduction/oxidation coupling reagent is from about 7.6 to about 9.6. In specific, non-limiting exemplary embodiments, the pH of the reduction/oxidation coupling reagent is about 8.0; in other embodiments the pH is about 8.6. The method is conducted at a temperature of from −20° C. to 37° C., more specifically, from −10° C. to +8° C. In specific embodiments, the method is conducted at 4° C.

The redox coupling reagent may be any redox coupling reagent(s). In some embodiments, the redox coupling reagent comprises reduced glutathione and oxidized glutathione. More specifically, in certain embodiments, the ratio of reduced glutathione to oxidized glutathione in the reduction/oxidation coupling reagent is about 1:1 to about 100:1. In other particular embodiments, the reduction/oxidation coupling reagent comprises cysteine/cystine. Specifically, the reduction/oxidation coupling reagent comprises from about 0.1 mM to about 10 mM cysteine and from about 0.1 mM to about 10 mM cystine. In yet other embodiments, the cysteine and cystine are present in a cysteine:cystine ratio of about 1:1 to about 10:1. In specific, non-limiting exemplary embodiments, the reduction/oxidation coupling reagent comprises about 6 mM cysteine and either about 1 mM or about 6 mM cystine. In some embodiments of the method of producing a recombinant IgG molecule (e.g., IgG1, IgG2, IgG3 or IgG4), the cysteine/cystine comprises about 6 mM cysteine and about 6 mM cystamine.

The contacting with the redox reagent may be performed over any convenient period of time sufficient to allow the unfolding and refolding to occur. In some embodiments, the contacting step with the redox coupling reagent, and further with or without the chaotropic agent, is performed for about 30 minutes or more. In some embodiments, the contacting step with the redox coupling reagent, with or without the chaotropic agent, is performed for about 4 to about 48 hours.

In other aspects of the invention, the contacting with the reduction/oxidation coupling reagent comprises providing the reduction/oxidation coupling reagent to the growth medium of the cell culture (i.e., the cell culture medium) from which the recombinant IgG is produced.

In some embodiments of the method of producing a recombinant IgG antibody, the contacting step comprises contacting at least a partially purified (or partially isolated) preparation of the recombinant IgG with the reduction/oxidation coupling reagent. Whether partially purified or not, the concentration of the recombinant IgG is contemplated as extending from the range of 1 mg/ml to about 50 mg/ml.

The methods of the present invention may further comprise an additional step of contacting the isolated recombinant protein that has been refolded according to the methods described above with a further composition comprising a reduction/oxidation coupling reagent. While in some embodiments a reductant and an oxidant are used, it is also contemplated that a reductant may be used alone.

In another aspect of the invention, the method of producing a recombinant polypeptide comprises contacting the polypeptide with a chaotropic agent before, after or concurrently with the contacting of the polypeptide with the reduction/oxidation coupling reagent. The chaotropic agent is any chaotropic compound or physical condition known in the art. An exemplary chaotropic agent is selected from the group consisting of urea, arginine, SDS and guanidine hydrochloride. In specific embodiments, the chaotropic agent is guanidine hydrochloride. Chaotropic agent also encompasses a low temperature condition, in which the temperature is low enough to cause a structural perturbation of, for example, IgG; in particular, a temperature ranging from zero to −30 degrees Celsius is contemplated. The concentration of any of the chaotropic agent compounds, such as the guanidine hydrochloride, may be varied according to particular conditions, however, in some embodiments, the concentration of the agent, e.g., guanidine hydrochloride, in the reaction mixture is from about 0.1 M to about 1M, and in other embodiments, the reaction mixture is from about 0.1M to about 1.5M. In particular embodiments, the concentration in the reaction mixture is about 0.5M. In still other exemplary embodiments, the concentration of the agent, e.g., guanidine hydrochloride, in the reaction mixture is about 0.9M. High pressure (1000-3000 bar), elevated temperature (above 55° C.), alcohol (up to 30%), low pH (below 3.5) are known to partially unfold IgG antibodies and can perform the role of the chaotropic agent. Combination of two or more of these unfolding elements can be used.

Another aspect of the invention provides a method of producing a recombinant polypeptide, as described above, further comprising isolating the contacted polypeptide or isolating a fraction of the contacted polypeptide having a desired refolded conformation. The isolating step used herein may be any isolating step conventionally employed to isolate proteins. The isolating step may comprise one or more techniques selected from the group consisting of reversed phase chromatography (e.g., HPLC), size-exclusion chromatography, ion-exchange chromatography, hydrophobic interaction chromatography, affinity chromatography, and electrophoresis, e.g., capillary electrophoresis. In embodiments that employ HPLC, the isolating comprises introducing a sample of the recombinant IgG preparation of the recombinant protein onto a reversed-phase chromatography column; separating the recombinant IgG from the other components of the preparation by eluting the recombinant IgG molecule from the reversed-phase HPLC, wherein the HPLC column is heated to a temperature of from about 50° C. to about 90° C.; and wherein the mobile phase of the reversed-phase HPLC comprises a water miscible organic solvent having a C18 eluotropic strength coefficient of at least 6.0, wherein the method produces a homogeneous population of IgG moieties than a similar method conducted in the absence of the reduction/oxidation coupling reagent or the HPLC separation parameters. The recombinant IgG can be similarly separated using cation exchange chromatography. A "homogeneous" population of an antibody means an antibody population that comprises largely a single form of the antibody, for example, at least 90% of the antibody in the solution or composition is in the properly folded form. Similarly, a "homogeneous" population of a polypeptide having a free or unpaired cysteine means a population of said polypeptide which comprises largely a single, properly folded form. The concentration of the recombinant IgG in the methods of the invention may be any concentration of the IgG that is amenable to refolding. As such, the concentration of IgG may be an industrial quantity (in terms of weight in grams) of IgG (e.g., an industrial amount of a specific IgG) or alternatively may be in milligram quantities. In specific embodiments, the concentration of the recombinant IgG molecule in the reaction mixture is from about 1 mg/ml and about 50 mg/ml, more specifically, 10 mg/ml or 15 mg/ml. The recombinant IgG1 molecules in these concentrations are particularly contemplated. In some embodiments, the recombinant IgG molecule is contacted with the reduction/oxidation coupling reagent at a pH of about 8.0.

In other aspects of the invention, the methods of the invention are characterized in that the contacting with the reduction/oxidation coupling reagent produces at least a 2-fold increase in the biological activity of the recombinant IgG antibody, (e.g., an IgG1, IgG2, IgG3 or IgG4 antibody) as compared to the same IgG antibody, that has not been refolded due to the production of an increase in the concentration of the active form of the IgG in the preparation prepared by the method as a result of treatment with the reduction/oxidation coupling reagent. In other embodiments, the contacting with the chaotropic agent produces at least a two-fold increase in the biological activity of IgG preparation as compared to the same antibody that has not been refolded, due to the production of an increase in the concentration of the active form of IgG in the preparation prepared by the method as a result of treatment with the chaotropic agent. In still other embodiments, the contacting of the recombinant polypeptide with the reduction/oxidation coupling reagent and the further contacting with the chaotropic agent produce a polypeptide having at least a three-fold increase in the biological activity of the polypeptide compared to the same polypeptide that is not contacted.

In still other embodiments, the combined effect of contacting with the chaotropic agent and the reduction/oxidation coupling reagent produces at least a 3-fold increase in the biological activity of the IgG preparation as compared to the same antibody that has not been refolded, due to the production of an increase in the concentration of the active form of IgG in the preparation prepared by the method as a result of treatment with the combination of the reduction/oxidation coupling reagent and the chaotropic agent. By refolding using the methods described herein the concentration of the desired conformational form of the protein is increased (enriched or increased abundance). During the isolation step after the refolding, more grams of desired conformational form are isolated. During the isolation step of the IgG without refolding, fewer grams of desired conformational form are isolated. The methods taught herein produce an at least 2-fold or a 3-fold increase in activity by increasing concentration of the active form from 40% to at least 80% or from 30% to at least 90%. The refolding procedure converts non-(or less)-active IgG molecules into (more) active IgG.

In a particular embodiment of the invention, the chaotropic agent is guanidine hydrochloride present in the reaction mixture in a final concentration of about 0.1M to about 1.5M.

The methods of the invention are further characterized in that they produce a more compact IgG structure in which the recombinant IgG, refolded in the presence of the reduction/oxidation reagent and chaotropic agent, produces an alteration in the compactness of the structure of the IgG protein. When treating the recombinant IgG with redox agents and chaotropic agent the IgG becomes less compact (as seen by SEC and LC/MS analysis) as compared to the non-treated material and the IgG treated with redox agents alone becomes more compact.

The methods of the invention produce an IgG population, which may further be processed by formulating the population of the IgG moieties, produced by the method, into a sterile bulk form. In other embodiments, a sterile unit dose form results from the formulating of the population of the IgG moieties produced by the method.

Also provided by the invention are methods of treating a subject in need of a recombinant IgG molecule comprising administering to the subject a homogeneous population of the IgG molecule prepared according to the methods of the present invention. In certain embodiments, the methods involve intravenous or subcutaneous administration of the IgG molecule.

Also contemplated for the present invention is a method for removing cysteinylation of IgG protein having free or unpaired cysteine and increasing relative abundance of the desired conformational isoform without cysteinylation, comprising contacting such proteins with a reduction/oxidation coupling reagent. Such proteins include, for example, IgG1.

Also contemplated for the present invention is a method for improving storage stability, thermal stability, homogeneity, or crystal properties of a protein having a free or unpaired cysteine comprising contacting said protein with a reduction/oxidation coupling reagent. In certain embodiments, the recombinant protein/antibody is a high molecular weight protein has a molecular mass of about 90 kDa.

In a related aspect of the invention, the method of producing a recombinant polypeptide comprises a contacting step wherein the contacting produces a polypeptide which is more stable in storage than the same polypeptide that is not contacted. Exemplary embodiments include methods wherein the contacting produces a polypeptide which is more thermally stable than the same polypeptide that is not contacted. In other embodiments, the method of producing a recombinant polypeptide comprises a contacting step wherein the contacting produces a polypeptide which has an improved crystal property compared to the same polypeptide that is not contacted.

Also encompassed by the present invention is a population of the recombinant IgG antibody moieties, prepared according to the methods described herein. For example, the invention comprehends a preparation of a polypeptide having at least one free cysteine residue prepared according to the method of producing a recombinant polypeptide described herein, wherein the preparation has a homogeneous population of the polypeptide, such as an IgG1, IgG2, IgG3, IgG4 polypeptide.

In a related aspect, the preparation comprises a recombinant IgG antibody and further comprises a pharmaceutically acceptable carrier, excipient or diluent (i.e., the preparation comprises a pharmaceutical composition). An exemplary embodiment of this aspect of the invention is a preparation of a recombinant polypeptide comprising at least one free cysteine residue. In some embodiments, the pharmaceutical composition comprises a population, e.g., a homogeneous population, of an IgG molecule, and a pharmaceutically acceptable carrier, excipient or diluent. The invention contemplates any known route of administration for the preparations comprising a polypeptide and a pharmaceutically acceptable carrier, excipient or diluent, such as intramuscular, parenteral, intravenous, or subcutaneous injection or implantation, urethral, rectal, or retroorbital delivery, and the like.

Other specific aspects of the invention include methods of producing an IgG antibody preparation comprising contacting a purified preparation of an IgG antibody that has been recombinantly produced by mammalian cells with a reduction/oxidation coupling reagent at a pH of about 5 to about 11; and optionally further contacting the preparation with a chaotropic agent before, after or concurrently with the contacting with the reduction/oxidation coupling reagent.

In such methods, the IgG antibody may be selected from the group consisting of an IgG1, IgG2, IgG3 and IgG4 antibody or fragments thereof that exhibit heterogeneity. Such heterogeneity may be introduced by the presence of IgG monomers, IgG multimers, IgG half molecules, or other fragments of an IgG molecule.

In some embodiments, the IgG antibody is an IgG2 antibody that elutes as several separate forms on RP-HPLC and the method decreases the number of forms eluting on RP-HPLC, or alters the relative distribution of the several separate forms on the RP-HPLC. In specific such embodiments, the method preferentially enriches at least one of the several separate forms in the preparation as determined by RP-HPLC. More particularly, the preferentially enriched form has a pharmaceutically desirable property as compared to a preparation that has not been treated by the method.

The term by "preferentially enriched" means an increase in relative abundance of a desired form or increase in relative proportion of a desired form. Pharmaceutically desirable properties as used herein include, but are not limited to increased stability, decreased viscosity, longer half life in circulation. For example, using the methods of the present invention the preparation is produced that is stable at a temperature of about 2-8° C. for at least one year; at about 25° C. for at least one month; following freezing and thawing. In addition, the more stable preparation is one which forms fewer dimers, aggregates, clips, particles than the same IgG antibody that is not contacted. A desirable preparation produced by the methods of the invention is an IgG antibody (or IgG antibody fragment) preparation which has lower viscosity than the same IgG antibody (or IgG antibody fragment) that is not been contacted with the reduction/oxidation and optional chaotropic agent as described herein. Another desirable IgG antibody (or IgG antibody fragment) preparation prepared according to the methods of the invention is one which has longer life in circulation than an IgG antibody (or IgG antibody fragment) of the same class that has not been contacted with the reduction/oxidation and optional chaotropic agent as described herein. In certain embodiments, such a desirable preparation has a half-life in circulation 20% longer than an IgG antibody (or IgG antibody fragment) of the same class that has not been contacted with the reduction/oxidation and optional chaotropic agent as described herein. The term "half-life" as used herein is the time it takes for the plasma concentration of a drug (in the present examples, an IgG antibody or fragment thereof) to reach half of it's original concentration at time zero.

In other embodiments, the IgG antibody is a recombinant IgG1 antibody having at least one free cysteine residue or a fragment of a recombinant IgG1 antibody having at least one free cysteine residue.

In other embodiments, the IgG antibody is an IgG4 antibody and the method decreases the formation of half molecules of IgG4.

In particular embodiments, it is contemplated that the method does not comprise contacting the preparation with a chaotropic agent.

The pH of the reduction/oxidation coupling reagent is from about 5 to about 10; for example between 7.6 to about 9.6 or more particular, about 8.0 to 8.6.

The reduction/oxidation coupling reagent comprises reduced glutathione and oxidized glutathione. For example, the ratio of reduced glutathione to oxidized glutathione is about 1:1 to about 100:1. In other embodiments, the reduction/oxidation coupling reagent comprises cysteine/cystine. For example, the cysteine/cystine comprises from about 0.1 mM to about 10 mM cysteine. In other examples, the redox coupling reagent comprises from about 0.1 mM to about 10 mM cystine and no exogenous cysteine is added. In still other examples, the cysteine/cystine is present in a cysteine:cystine ratio of about 1:1 to about 10:1. In other examples, the cysteine/cystine comprises about 6 mM cysteine and about 1 mM cystine. In still other examples, the cysteine/cystine comprises about 6 mM cysteine and about 6 mM cystamine.

The methods may involve a contacting step which is performed for at least 30 minutes. In other examples, the contacting step is performed for about 4 to about 48 hours.

In particular examples, the recombinant IgG antibody is purified from the media into which it has been secreted prior to the contacting. In other embodiments, the contacting occurs when the recombinant IgG antibody is in the media in which it has been secreted. In still other embodiments, the recombinant IgG antibody is partially purified from the media in which it has been secreted in that, for example, the cells and other particulate matter have been removed from the media prior to the contacting.

In specific embodiments, the methods of the invention involve multiple steps of contacting the recombinant IgG antibody with a reduction/oxidation coupling reagent.

In specific embodiments, the methods of the invention involve isolating the IgG antibody from the culture medium of mammalian cells in a method comprising culturing a mammalian cell that expresses and secretes into culture medium an IgG antibody or an IgG antibody fragment; adding reduction/oxidation coupling reagent at a pH of about 5 to about 11, and optionally contains a chaotropic agent upon secretion of antibody from the cell. Such isolating may involve one or more chromatography steps.

The methods of the invention may be performed on a media or other preparation that comprises a concentration of from about 1 mg/ml and about 50 mg/ml of the recombinant IgG antibody.

The methods of the invention are such that the contacting produces a IgG antibody which is more stable in storage than the same IgG antibody that is not contacted. The methods of the invention are such that the contacting produces a IgG antibody which is more thermal stable than the same IgG antibody that is not contacted. In other embodiments, the contacting produces a IgG antibody which has an improved crystallization property compared to the same IgG antibody that is not contacted. As used herein the term crystallization property refers to crystal growth, morphology, size, uniformity, crystal yield, suspendability of the crystal, suspendability of the crystal, or any other property of the IgG crystal that facilitates its preparation into a pharmaceutical preparation. Preferably, the crystal will be used in solution, either alone or in combination with a pharmaceutically acceptable adjuvant, diluent or excipient.

The contacting with the reduction/oxidation reagent (and optionally the chaotrope) produces an IgG antibody population which is more homogeneous than the same IgG antibody population that is not contacted. In other aspects, the contacting produces a IgG antibody having at least a two-fold increase in its biological activity compared to the same IgG antibody that is not contacted. In specific embodiments, the method contemplates contacting the IgG antibody with a chaotropic agent before, after or concurrently with the contacting with the reduction/oxidation coupling reagent. The chaotropic agent may be selected from the group consisting of: urea, arginine, SDS and guanidine hydrochloride. In preferred embodiments, the chaotropic agent comprises guanidine hydrochloride.

In some embodiments, the concentration of guanidine hydrochloride is from about 0.1 M to about 1.5 M. In others, the concentration of guanidine hydrochloride is from about 0.1 M to about 1M. In a specific embodiment, the concentration of guanidine hydrochloride is about 0.5M. In another specific embodiments, the concentration of guanidine hydrochloride is about 0.9M.

In particular embodiments, the contacting with the reduction/oxidation coupling reagent and the further contacting with the chaotropic agent produce an IgG antibody having at least a three-fold increase in its biological activity compared to the same IgG antibody that is not contacted.

The methods of the invention also may comprise formulating the IgG antibody produced by the methods into a sterile bulk form. In other embodiments, the methods further comprise formulating the IgG antibody as produced by the method into a sterile unit dose form. In still other embodiments, the methods further comprise isolating a fraction of the contacted IgG antibody having a desired refolded conformation. Such a procedure for the isolating is selected from the group consisting of: reversed-phase chromatography HPLC, size-exclusion chromatography, ion-exchange chromatography, hydrophobic interaction chromatography, affinity chromatography, and electrophoresis. In specific embodiments, the procedure for the isolating is ion-exchange chromatography.

Also contemplated herein is a preparation of an IgG antibody prepared according to the methods described herein, the preparation having a homogeneous population of the IgG antibody. The preparation may further comprise pharmaceutically acceptable carrier, excipient or diluent.

Also contemplated is a composition comprising a homogeneous population of a recombinant IgG antibody and a pharmaceutically acceptable carrier, excipient or diluent. The composition can contain an IgG1 antibody, IgG2 antibody, an IgG4 antibody, or IgG monomers of an IgG1, IgG2 or IgG4, IgG multimers of an IgG1, IgG2 or IgG4, IgG half molecules of an IgG1, IgG2 or IgG4, or other fragments of such IgG molecules. Methods of treating a subject with such homogeneous populations also are contemplated. In such methods, the administration may be fore example subcutaneous or intravenous administration.

Also contemplated is a method of detecting or monitoring the quality of a recombinant IgG antibody during the manufacturing, formulation, and/or storage thereof, comprising:

a) contacting a preparation of the IgG that has been recombinantly produced by mammalian cells with a reduction/oxidation coupling reagent at a pH of about 5 to about 11, and, optionally, further contacting the preparation with a chaotropic agent before, after or concurrently with the contacting with the reduction/oxidation coupling reagent;

b) cleaving the IgG molecule that has been treated according to step a) into fragments; and c) subjecting the intact IgG and/or fragments from step b) to a chromatography analysis, thereby detecting or monitoring the quality of the IgG molecule.

In such methods the IgG antibody is an IgG1 antibody and the monitoring the quality comprises monitoring the status of free or unpaired cysteine of the IgG1 antibody.

In other such methods, the IgG antibody is an IgG2 antibody and the monitoring the quality comprises monitoring the number of forms of the IgG2 to determine heterogeneity of the preparation.

In other such methods the IgG molecule is an IgG4 molecule and the monitoring the quality comprises monitoring the presence of half molecules of IgG4.

In some aspects the chromatography comprises an LC/MS analysis.

In specific aspects, the detecting or monitoring is conducted during the purification step of the IgG molecule, the purification comprising column chromatography.

Also provided are methods of producing a recombinant IgG antibody, or an IgG antibody fragment comprising:

contacting an IgG antibody or an IgG antibody fragment that has been recombinantly produced by mammalian cells with a reduction/oxidation coupling reagent at a pH of about 5 to about 11; and optionally further contacting the IgG antibody or IgG antibody fragment with a chaotropic agent before, after or concurrently with the contacting with the reduction/oxidation coupling reagent.

In some embodiments, prior to such methods the IgG antibody or IgG antibody fragment is isolated from the culture medium of mammalian cells in a method comprising culturing a mammalian cell that expresses and secretes into culture medium an IgG antibody or an IgG antibody fragment; adding reduction/oxidation coupling reagent at a pH of about 5 to about 11, and optionally contains a chaotropic agent upon secretion of antibody from the cell.

It should be understood that the recombinant IgG antibody may be an IgG1, IgG2 or IgG4.

The methods of the invention provide for preparation of a crystallized form of an intact recombinant IgG antibody by performing the refolding methods described herein and preparing a crystallized form of the recombinant IgG antibody. In some embodiments, prior to preparation of such crystals, the methods may involve isolating the recombinant IgG antibody prepared by the methods described herein.

In specific embodiments, the recombinant IgG antibody is attached to a stationary phase of a chromatographic column and redox reagents and chaotropic reagents are a part of the mobile phase. In other embodiments, the reduction/oxidation coupling reagent is an enzyme. In still other embodiments, the reduction/oxidation coupling reagent includes bivalent metal ions and oxygen.

Also described herein is a method of producing an IgG antibody preparation comprising contacting an isolated preparation of an IgG antibody that has been recombinantly produced by mammalian cells with a reduction/oxidation coupling reagent at a pH of about 5 to about 11; and optionally further subjecting the preparation to denaturation by high pressure before, after or concurrently with the contacting with the reduction/oxidation coupling reagent.

The present invention involves a method of producing an IgG antibody or a fragment thereof comprising culturing a mammalian cell that expresses and secretes into culture medium an IgG antibody or an IgG antibody fragment; and adding reduction/oxidation coupling reagent at a pH of about 5 to about 11, and optionally contains a chaotropic agent upon secretion of antibody from the cell; and thereby producing an IgG antibody or fragment thereof having improved pharmaceutical and crystallization properties as compared to an IgG antibody or fragment thereof that has not been exposed to the reduction/oxidation reagent and optionally chaotropic agent.

Described herein is an improvement in a mammalian cell-based method for producing a recombinant IgG antibody or a recombinant IgG antibody fragment, the improvement comprising adding to a culture medium used for the production of the IgG antibody or the IgG antibody fragment a reduction/oxidation coupling reagent at a pH of about 5 to about 11; and optionally a chaotropic agent upon secretion of the IgG antibody or the IgG antibody fragment into the medium.

Other features and advantages of the invention will become apparent from the following detailed description. It should be understood, however, that the detailed description and the specific examples, while indicating some embodiments of the invention, are given by way of illustration only, because various changes and modifications within the spirit and scope of the invention will become apparent to those skilled in the art from this detailed description.

BRIEF DESCRIPTION OF THE FIGURES

The following drawings form part of the present specification and are included to further illustrate aspects of the present invention. The invention may be better understood by reference to the drawings in combination with the detailed description of the specific embodiments presented herein.

FIG. 25. Glu-C peptide maps of IgG1 CHO: (A) bulk and (B) native refold.

DETAILED DESCRIPTION OF THE INVENTION

Figure 1:
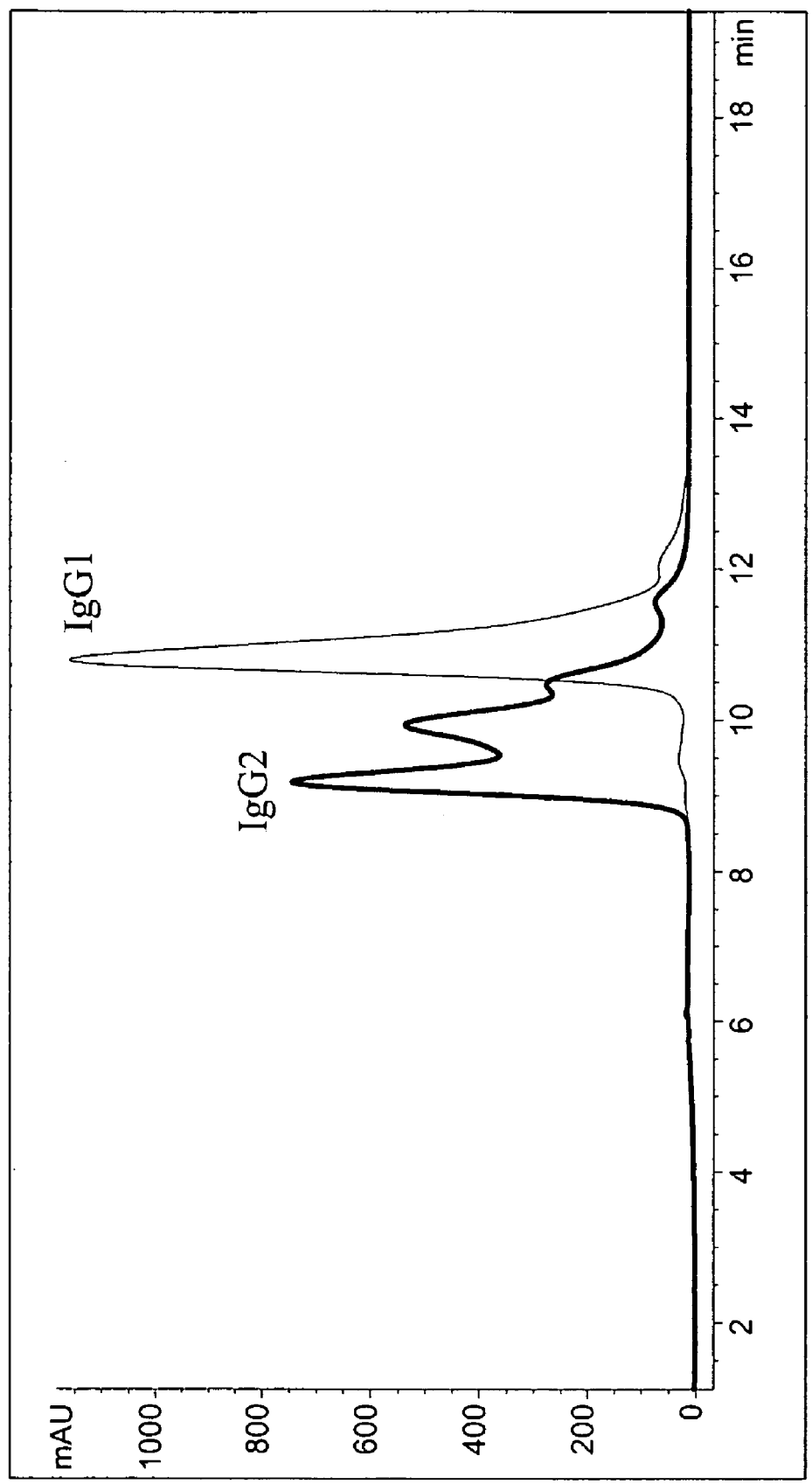
FIG. 1 shows RP chromatograms of two recombinant monoclonal human antibodies with the same CDRs and implemented as IgG1 and IgG2 modalities. There is 95% amino acid homology between the two molecules but there is significant difference in the homogeneity of the antibodies preparation depending on whether the antibodies are IgG1 or IgG2 antibodies.

Oxidative refolding of proteins from the inclusion body state is a common practice in the prokaryotic production of recombinant proteins but is not typically implemented in eukaryotic cell production processes for the production of recombinant proteins. This is because eukaryotic cells are thought to contain sufficient cellular machinery to correctly refold the recombinantly produced proteins. However, as described in U.S. Patent Application Nos: 60/548,302, Dillon et al., filed Feb. 27, 2004, and 60/538,982 Bondarenko et al., filed Jan. 23, 2004, (each incorporated herein by reference in its entirety), recent improvements in RP-HPLC-separation and detection techniques reveal that there is significant conformational heterogeneity in recombinantly produced high molecular weight proteins that were previously thought to be homogeneous. As discussed in the aforementioned applications, the nature of the heterogeneity is due at least in part to disulfide scrambling.

The interest in the structure and function of IgG molecules has been revived recently in the protein pharmaceutical industry. IgG1 and IgG2 subclasses have attracted special interest, because they are the most abundant, long lasting and stable immunoglobulins in circulation. The present invention is directed to addressing a need for methods of producing more structurally homogeneous recombinant proteins, and more particularly, mammalian-cell produced recombinant IgG antibodies and particularly, IgG1, IgG2 and IgG4 therapeutic antibodies with improved activity.

It has been suggested in several previous reports, that IgG2 molecules contain free thiol groups and are structurally heterogeneous as compared to other subclasses of gamma globulins. In one report, the content of free thiol groups was determined for all four human IgG antibodies by the reaction with 5,5'-dithio(2,2'-dinitro)benzoate (DTNB)(Schauenstein et al 1986 Int. Arch. Allergy Immunol., v. 80, p. 174-179). The uncovered free thiols (about 0.24 per mole of human IgG) were assigned to IgG2 subclass. Others have also reported that all four human IgG subclasses were subjected to reduction of interchain disulfide bonds by thioredoxin with thioredoxin reductase and NADPH. IgG2 was found different from other subclasses in two effects: 1) it resisted reduction and 2) consumed NADPH reagent. The later finding suggested that the reagent was consumed by reduction of a labile interchain or surface-exposed mixed disulfide. In yet another study, IgG2 covalent dimers were detected in pooled human gamma globulin and several normal sera (Yoo et al., 2003, J. Immunol., v. 170, p. 3134-3138). Cyanogen bromide cleavage analysis of the dimers indicated that one or more cysteine residues in the hinge are involved in dimer assembly, again suggesting presence of free or labile cysteines in hinge of IgG2. A study by Phillips et al. (J. Immun., v. 31, p. 1201-1210, 1994), using sedimentation and electron microscopy analysis, identified multiple shapes of IgG2 molecules and their complexes with bivalent hapten and only a single form for other three subclasses of human gamma globulins.

According to a recent report, well over 200 structures of antibody fragments, mainly Fab and Fab', have been determined (Saphire et al., 2002, J. Mol. Biol., v. 319, p. 9-18). Crystals of intact antibodies have been reported only ten times and only seven of these crystals provided partial or complete structures. All these structures were either murine. IgG or human IgG1 antibodies, but not human IgG2 (Saphire et al., 2002, J. Mol. Biol., v. 319, p. 9-18). Entire structures of IgGs with full-length hinges have been reported only three times: mAb 231, a murine IgG2a (Harris et al., 1992, Nature, v. 360, p. 369-372; Larson et al., 1991, J. Mol. Biol., v. 222, p. 17-19), mAb 61.1.3, a murine IgG1 (Harris et al., 1998, J. Mol. Biol., v. 275, p. 861-872); and a human IgG1 b12, directed against HIV-1 gp120 (Saphire et al., 2001, Science, v. 293, p. 1155-1159; Saphire et al., 2002, J. Mol. Biol., v. 319, p. 9-18). Fragments of the crystal image of a human IgG1 antibody near the hinge from PDB number 1HZH is available (Saphire et al., 2001, Science, v. 293, p. 1155-1159). The fact, that crystal structure of a human IgG2 is not available, leaves the question about exact disulfide connectivity unanswered and also suggests that this IgG subclass may be heterogeneous, which makes it a difficult subject for crystallization. It also highlights a need for new methods of structural analysis. The inventors used their newly developed method of analysis of intact antibodies by using reversed-phase chromatography on-line with mass spectrometry to facilitate discovery and characterization of heterogeneity of human IgG2 antibodies (Dillon et al., 2004, J. Chromatogr. A, v. 1053, p. 299-305).

Having discovered that there is significant conformational heterogeneity in recombinant IgG2 antibodies expressed in mammalian cells, the inventors developed a refolding procedure to enrich two forms of the protein as described in Examples 1-3 herein. Influence of additives, such as GndHCl, glutathione, L-arginine, on refolding of a single-chain immunoglobulin-folded proteins was discusses in (Umetsu et al., 2003, J. Biol. Chem., v. 278, p. 8979-8987). Spontaneous folding in the 1M GndHCl buffer resulted in a structure in which a correct disulfide bonding was achieved; however, the addition of L-arginine resulted in the formation of a partially folded intermediate without disulfide linkages (Umetsu et al., 2003, J. Biol. Chem., v. 278, p. 8979-8987).

In another specific example, the present inventors have discovered that one of the antibodies against IL-15 described in, e.g., U.S. Publication No. 2003/0138421, i.e., 146B7, contains an unpaired cysteine residue. Specifically, 146B7 has a free cysteine in position 104 of the CDR3 heavy chain. This free cysteine can be a source of covalent dimerization and lead to stability issues during formulation or storage. The presence of this residue confounds attempts to produce a uniform, active sample of that recombinant IgG1. The addition of redox agents facilitates the production of a structurally homogeneous and more active form of this IgG1 molecule. The addition of the redox agents is combined with the addition to chaotropic agents to facilitate the production of refolded IgG1 molecules that are more homogeneous than the same molecules that have not been treated with the redox coupling agent and chaotropic agent.

As discussed in Example 9, the methods of the present invention also are useful in the preparation of uniform intact IgG4 molecules. As IgG4 does not activate complement, the chance of an immunogenic response and inflammation due to antigen-antibody-complement complexes is very small with IgG4 molecules. This makes IgG4 a very attractive candidate for therapy as it is expected to be a safe therapeutic modality: IgG4 should simply bind to antigen and should not trigger any additional response in human body.

An IgG4-based response is generated in response to, for example, antigens such as dust mite, grass pollen or bee sting. These antigens are typically eliminated without significant immune response and inflammation. On the other hand, due to the unique structure of the hinge of IgG4, this IgG is present as a mixture of intact and half molecules. Without being bound to any particular theory or mechanism of action, it is noted that the presence of half molecules of IgG4 could be deleterious in the development of IgG4 moieties as therapeutic compositions. The half molecules can potentially create a problem, because they can exchange between two different IgG4 molecules. In such circumstances, an IgG4 molecule is created, which would bind to two antigens with two halves (arms). Such an IgG4 is bifunctional and monovalent. It is contemplated that such bifunctional and monovalent features on an IgG4 would render the hybrid IgG4 molecule potentially unsafe as a therapeutic agent. For example, a therapeutic IgG4 can be developed with the purpose to bind to an arthritic related receptor. If other IgG4 half molecules are present in the site of injection or entire human body, it may lead to the bifunctional IgG4, which binds both the receptor and grass pollen antigen. This may lead to immune response and inflammation. In the present invention, methods are provided for refolding IgG4 moieties. Such refolding will be used to eliminating the half molecules of IgG4, which often are present together with intact IgG4 molecules.

In some aspects of the invention, the introduction and optimization of redox components and/or chaotropic agents directly into the fermentation medium in which the eukaryotic cells are grown such that the appropriate redox potential is achieved for refolding of the IgG (i.e.; the IgG1, IgG2, IgG3, or IgG4) product secreted into the media are also contemplated. Thus, the media is supplemented with, or optimized for, components such as cysteine, cystine, cystamine, glutathione, copper, and/or other reducing/oxidizing agents in order to achieve the appropriate redox potential. The optimization of the redox components is achieved by varying the components in the fermentation media. The heterogeneity of the secreted IgG product may be assessed using HPLC/MS methods or any other protein separation technique that yields information about the heterogeneity of the composition separated. The redox reagents and/or chaotropes that provide a more uniform homogeneous recombinant product are thus readily identified.

Alternatively to, or in combination with, inclusion of the redox reagents in the fermentation media of the recombinant protein producing host cells, a separate, distinct processing step may be introduced in which oxidative refolding of the protein is achieved. In such a further processing step, the refolding solution may contain denaturants such as guanidine hydrochloride or urea; folding agents such as, polyols, polymers, or detergents and/or reducing agents.

Methods for producing recombinant antibodies in mammalian cells are known. In such methods, the antibody production involves induction of protein expression. Nucleic acids encoding an IgG antibody or an IgG antibody fragment are conveniently rendered expressible by operative association with a promoter, preferably a controllable promoter functional in mammalian cells. Such recombinant constructs are designed for expression of IgG antibody protein in a suitable host (e.g., bacterial, murine, or human). Suitable promoters for expression of proteins and polypeptides herein are widely available and are well known in the art. Inducible promoters or constitutive promoters that are linked to regulatory regions (e.g., enhancers, operators, and binding regions for transcription or translation factors) are preferred. An "inducible" promoter is defined herein as a controllable promoter, including promoters typically referenced as inducible promoters (i.e., subject to positive regulation in being inactive until activated or induced by the presence of an activator or inducer) or as derepressible promoters (i.e., subject to negative regulation in being active unless a repressor is present, with removal of the repressor, or depression, resulting in an increase in promoter activity). Promoters contemplated herein include, for example, but are not limited to, the trp, lpp, tac, and lac promoters, such as the lacUV5, from *E. coli*; the P10 or polyhedrin gene promoter of baculovirus/insect cell expression systems (see, e.g., U.S. Pat. Nos. 5,243,041, 5,242,687, 5,266,317, 4,745,051, and 5,169,784) and inducible promoters from other eukaryotic expression systems, as would be known in the art. For expression of the proteins, such promoters are inserted in a plasmid in operative linkage with a control region such as the operator region of the trp operon.

Preferred promoter regions are those that are inducible and functional in mammalian cells, for example. Examples of suitable inducible promoters and promoter regions for bacterial expression include, but are not limited to: the *E. coli* lac operator responsive to isopropyl β D thiogalactopyranoside (IPTG; see Nakamura et al., 1979. Cell 18:1109-1117); the metallothionein promoter metal-regulatory-elements responsive to heavy-metal (e.g., zinc) induction (see, e.g., U.S. Pat. No. 4,870,009); the phage T7lac promoter responsive to IPTG (see, e.g., U.S. Pat. No. 4,952,496; and Studier et al., 1990 Meth. Enzymol. 185:60-89) and the TAC promoter. Depending on the expression host system to be used, the vector (e.g., plasmid, phagemid, cosmid, artificial chromosome, virus) may optionally include a selectable marker gene or genes that are functional in the host. Thus, for example, a selectable marker gene includes any gene that confers a phenotype on a host cell that allows transformed host cells to survive under certain conditions, such as exposure to an antibiotic. Also contemplated are screenable markers for inclusion in a vector, with screenable markers conferring a distinguishable phenotype on transformed host cells. Suitable selectable marker genes for hosts include, for example, the ampicillin resistance gene (Ampr), tetracycline resistance gene (Tcr) and the kanamycin resistance gene (Kanr).

In various expression systems, vectors (e.g., plasmids) may also include DNA encoding a signal for secretion of the operably linked protein. Secretion signals suitable for use are widely available and are well known in the art. Eukaryotic secretion signals functional in mammalian cells are preferred. A variety of eukaryotic secretion signals are known to those of skill in the art, all of which are contemplated (see, e.g., von Heijne, J. Mol. Biol. 184:99-105, 1985). In specific embodiments, it is contemplated that the redox agent is introduced into the cell culture medium of cells expressing and secreting the recombinant antibodies at a point when the expression of the recombinant IgG antibody or fragment thereof has been induced in those cells. The redox agent may be added in a single dose bolus or may be added in multiple doses. For example in the case of cysteine/cystine as reduction/oxidation coupling reagents it may be desirable to have multiple daily doses of cysteine/cystine added to maintain the appropriate amount of cysteine/cystine in the refolding medium.

In yet another aspect the redox agent is introduced directly into the protein crystallization solutions such that is folded protein can refold in solution and attach to the growing protein crystal resulting in improved protein crystallization yields. The crystallization step may be combined with any improvements achieved through the use of protein material that has already been treated by refolding using the redox conditions in the fermentation media, and/or through the further processing steps. By refolding of the protein during fermentation, in a separate processing step or within the crystallization solution, the present invention provides products with improved pharmaceutical and crystallization properties, including improved homogeneity, activity/potency, stability, crystal growth, and crystallization yield. This approach for improving the pharmaceutical and crystallization properties of the recombinant proteins is preferably to the use CEX chromatography because the latter technique would require collection of only the active component from a bulk recombinant protein mix, which is more costly and leads to significant loss of material.

In some other aspects of the present invention, there are provided methods of producing human or humanized IgG antibodies, such as, for example a fully human IgG1 against IL-15, or IgG2 against IL-1R, which methods include a step of refolding of the IgG produced by recombinant Chinese Hamster Ovary (CHO) cells and obtaining structurally homogeneous, active forms of the IgG molecule. In those circumstances where the IgG is an IgG2, the structurally homogeneous forms are one of the forms 1, 2, 3, or 4 identified through HPLC profiles described herein such that only e.g., form 3 is produced, or only form 1 is produced etc. In those circumstances where the IgG is an IgG1 antibody, it is contemplated that any unpaired free cysteines are treated so that they do not lead to deleterious dimerization. In the case of IgG4 antibodies, the methods of the invention provide for IgG4 preparations that are intact rather than present as half-molecules. To achieve these beneficial outcomes in certain embodiments, the refolding can be performed using cysteine-cystine, cysteine-cystamine, glutathione, copper, molecular oxygen, and chaperones and different buffer, temperature and time compositions. Typical refolding conditions include for example, incubation of the recombinant IgG molecule at 3-15 mg/mL in two buffers 1) 200 mM Tris buffer at pH 8.0 (native refold); 2) 200 mM Tris buffer at pH 8.0 with 0.9M GuHCl (GuHCl refold). A combination of cysteine: cystine is added at the approximate molar ratio of 6 mM:1 mM, respectively. The samples were placed at 2-8° C. for 48 hours. Aliquots were taken at 24 and 48 hours for analysis. Refolding of the recombinant IgG molecule using such typical refolding conditions in the presence of redox reagent and chaotropic agent produces a single structural form with a three-fold increased activity per gram of protein. In certain embodiments, the refolding step will thus triple the production of an IgG molecule and reduce by three times the protein concentration need in formulation solutions to achieve the same activity.

It should be understood that the methods of the invention can be used to prepare a protein formulation for use in a patient, e.g., an IgG1 such as an IgG1 directed against IL-15, or an IgG2 against IL-1R where the preparation involves mammalian cell production of the protein, purification of the protein from that mammalian cell culture, refolding of the purified protein using the refolding methods described herein, exchanging the buffer of the composition thus produced to formulation buffer and producing a single dose formulation that may be used in the patient. Alternatively, the preparation of formulation involves the steps of mammalian cell production of the protein, purification of the protein followed by refolding of the protein as described herein, followed by isolation of desired form of the protein, after which the buffer of the composition thus produced is exchanged to formulation buffer and producing a single dose formulation that may be used in the patient.

The invention provides methods of increasing the recovery of active recombinant proteins. In addition the invention employs chaotrope treatments (such as, for example, denaturants such as SDS, guanidium hydrochloride or urea) to further process the proteins. The methods of producing the appropriately refolded protein are combined with advantageous LC methods of isolating the protein as described in detail below. These combined refolding production and protein purification methods of the invention are particularly advantageous when the recombinant protein is intended to be used in vivo as a drug or biologic.

Use of the LC methods will allow the skilled person to assess those particular refolding conditions that yield the desired protein conformation for any given recombinant protein. Other purification and isolation methods also may be used.

The desired conformation of a recombinant protein may or may not have a different arrangement of disulfide bonds, although preferably the conformation contains native disulfide bonds.

It has been found that the methods described herein form a gentle and effective process for improving the production process for recombinant IgG antibodies or fragments thereof that can adopt multiple conformations. In one aspect, the methods of the invention can be used on preparations of recombinant IgG antibodies or fragments thereof in which the preparation of the IgG antibody or fragment thereof is a heterogeneous mixture which contains stable and unstable conformations of the IgG antibody or fragment thereof. The terms "stable" and "unstable" are used as relative terms. The stable conformation will have, for example, a higher melting temperature (Tm) than the unstable conformation when measured in the same solution. A conformation is stable compared to another conformation when the difference in the Tm is at least about 2° C., more preferably about 4° C., still more preferably about 7° C., yet more preferably about 10° C., even more preferably about 15° C., still more preferably about 20° C., even still more preferably about 25° C., and most preferably about 30° C., when measured in the same solution.

Thus, in one aspect, the invention contemplates contacting a preparation of recombinant protein that is made up of a heterogeneous mixture of least two configurational isomers of the recombinant protein to a reduction/oxidation coupling reagent for a time sufficient to increase the relative proportion of the desired configurational isomer and determining the relative proportion of the desired configurational isomer in the mixture. In another aspect, the invention contemplates contacting a preparation of a recombinant protein that has been produced by mammalian cells with a reduction/oxidation coupling reagent, at a pH of about 7 to about 11, and isolating a fraction of the preparation of the recombinant protein with a desired conformation. Some recombinant proteins are glycosylated recombinant proteins such as, e.g., those produced by eukaryotic cells. In certain aspects, the methods of the present invention are used to reduce the conformational heterogeneity that is induced by disulphide scrambling. In more specific aspects this conformational heterogeneity is present in antibodies, and more particularly, IgG1, IgG2, IgG3, or IgG4 antibodies. It should be noted that the term "configuration" is used interchangeably with the term "conformation" herein throughout and is intended to mean a protein that has a different secondary, tertiary or quaternary structure from another protein that has the same primary structure (the same amino acid sequence). Using the redox reagents either alone or in combination with the further processing using chaotropic agents such as guanidine hydrochloride, it is possible to produce a more homogeneous, and more therapeutically active IgG protein as compared to a sample of the same protein produced in the same manner but for the presence of the redox reagents and/or chaotropes.

Generally, the methods of the invention are useful for improving production processes for recombinant IgG (i.e., the IgG1, IgG2, IgG3, or IgG4) molecules or proteins. Recombinant molecules or recombinant proteins are proteins produced by the process of genetic engineering. The term "genetic engineering" refers to any recombinant DNA or RNA method used to create a host cell that expresses a gene at elevated levels, at lowered levels, and/or a mutant form of the gene. In other words, the cell has been transfected, transformed or transduced with a recombinant polynucleotide molecule, and thereby altered so as to cause the cell to alter expression of a desired protein. Methods and vectors for genetically engineering cells and/or cell lines to express a protein of interest are well known to those skilled in the art; for example, various techniques are illustrated in Current Protocols in Molecular Biology, Ausubel et al., eds. (Wiley & Sons, New York, 1988, and quarterly updates) and Sambrook et al., Molecular Cloning: A Laboratory Manual (Cold Spring Laboratory Press, 1989). Genetic engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, Proc. Natl. Acad. Sci. USA 96(6):2758-63).

In the methods of treating a disease, disorder, or condition, in addition to the prophylactic methods or method of preventing such diseases, disorders and conditions, an "effective amount" of a recombinant polypeptide is an amount of the polypeptide that will produce the desired biological or physiological effect, as would be known in the art. Particularly with respect to treatment methods, as well as the methods of ameliorating a symptom associated with a disease, disorder or condition, an "effective amount" is used synonymously with a "therapeutically effective amount." In such methods, a "subject in need" is any animal, e.g., a human, exhibiting a symptom of, at risk of developing, or diagnosed as having a disease, disorder or condition.

The invention finds particular use in improving the production of any recombinant proteins that is produced in e.g., mammalian cells and requires appropriate refolding. In some embodiments, the invention is specifically directed to improved production and refolding of 146B7, an anti-IL-15 IgG1 molecule. The heterogeneity of such proteins due to the presence of an unpaired cysteine residue at position 104 (Cys104) is significantly reduced as a result of the use of the redox reagents described herein. These beneficial results may be assessed by monitoring such heterogeneity using the LC and LC/MS methods known to those of skill in the art. Specifically, proteins that are secreted by fungal cell systems (e.g., yeast, filamentous fungi) and mammalian cell systems will be glycosylated. Preferably, the proteins are secreted by mammalian production cells adapted to grow in cell culture. Examples of such cells commonly used in the industry are CHO, VERO, BK, HeLa, CV1 (including Cos), MDCK, 293, 3T3-myeloma cell lines (especially murine), PC12 and WI38 cells. Particularly preferred host cells are Chinese hamster ovary (CHO) cells, which are widely used for the production of several complex recombinant proteins, e.g. cytokines, clotting factors, and antibodies (Brasel et al., 1996, Blood 88:2004-2012; Kaufman et al., 1988, J. Biol Chem 263: 6352-6362; McKinnon et al., 1991, J Mol Endocrinol 6:231-239; Wood et al., 1990, J. Immunol 145:3011-3016). The dihydrofolate reductase (DHFR) deficient mutant cell line (Urlaub et al., 1980, Proc Natl Acad Sci USA 77:4216-4220), DXB11 and DG-44, are the CHO host cell lines of choice because the efficient DHFR selectable and amplifiable gene expression system allows high level recombinant protein expression in these cells (Kaufman R. J., 1990, Meth Enzymol 185:527-566). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

It has been found that the invention is a gentle and effective process for improving the production process for recombinant IgG (e.g., IgG1, IgG2, IgG3, or IgG4) molecules that can adopt multiple conformations and/or contain more than one domain. A "domain" is a contiguous region of the polypeptide chain that adopts a particular tertiary structure and/or has a particular activity that can be localized in that region of the polypeptide chain. For example, one domain of a protein can have binding affinity for one ligand, and one domain of a protein can have binding affinity for another ligand. In a thermostable sense, a domain can refer to a cooperative unfolding unit of a protein. Such proteins that contain more than one domain can be found naturally occurring as one protein or genetically engineered as a fusion protein. In addition, domains of a polypeptide can have subdomains.

The inventive compositions and methods are also useful for preparation of other types of recombinant IgG proteins, including immunoglobulin molecules or portions thereof, and chimeric antibodies (e.g., an antibody having a human constant region coupled to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody based polypeptides (see, for example, Larrick et al., 1989, Biotechnology 7:934-938; Reichmann et al., 1988, Nature 332:323-327; Roberts et al., 1987, Nature 328:731-734; Verhoeyen et al., 1988, Science 239:1534-1536; Chaudhary et al., 1989, Nature 339:394-397). Preparations of fully human antibodies (such as are prepare using transgenic animals, and optionally further modified in vitro), as well as humanized antibodies, can also be used in the invention. The term humanized antibody also encompasses single chain antibodies. See, e.g., Cabilly et al., U.S. Pat. No. 4,816,567; Cabilly et al., European Pat. No. 0,125,023 B1; Boss et al., U.S. Pat. No. 4,816,397; Boss et al., European Pat. No. 0,120,694 B1; Neuberger, M. S. et al., WO 86/01533; Neuberger, M. S. et al., European Pat. No. 0,194, 276 B1; Winter, U.S. Pat. No. 5,225,539; Winter, European Pat. No. 0,239,400 B1; Queen et al., European Pat. No. 0 451 216 B1; and Padlan, E. A. et al., EP 0 519 596 A1. The method of the invention may also be used during the preparation of conjugates comprising an antibody and a cytotoxic or luminescent substance. Such substances include: maytansine derivatives (such as DM1); enterotoxins (such as a Staphlyococcal enterotoxin); iodine isotopes (such as iodine-125); technium isotopes (such as Tc-99m); cyanine fluorochromes (such as Cy5.5.18); and ribosome-inactivating proteins (such as bouganin, gelonin, or saporin-S6).

Preparations of various fusion proteins can also be prepared using the inventive methods. Examples of such fusion proteins include proteins expressed as a fusion with a portion of a recombinant IgG (i.e., the IgG1, IgG2, IgG3, or IgG4) molecule, proteins expressed as fusion proteins with a zipper moiety, and novel polyfunctional proteins such as a fusion proteins of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins. Any of the above molecules can be expressed as a fusion protein including but not limited to the extracellular domain of a cellular receptor molecule, an enzyme, a hormone, a cytokine, a portion of an immunoglobulin molecule, a zipper domain, and an epitope.

The preparation of the recombinant protein is preferably achieved by using the redox reagents described herein in the media of the cell culture. The recombinant proteins are produced by the cells in that culture and subsequently purified. The preparation of recombinant protein can be a cell culture supernatant, cell extract, but is preferably a partially purified fraction from the same. By "partially purified" means that some fractionation procedure, or procedures, have been carried out, but that more polypeptide species (at least 10%) than the desired protein or protein conformation is present. One of the advantages of the methods of the invention is that the preparation of recombinant protein can be at a fairly high concentration. Some concentration ranges are 0.1 to 20 mg/ml, more preferably from 0.5 to 15 mg/ml, and still more preferably from 1 to 10 mg/ml.

The preparation of recombinant protein can be prepared initially by culturing recombinant host cells under culture conditions suitable to express the polypeptide, in the presence of the redox reagents as described herein. The polypeptide can also be expressed as a product of transgenic animals, e.g., as a component of the milk of transgenic cows, goats, pigs, or sheep which are characterized by somatic or germ cells containing a nucleotide sequence encoding the polypeptide. The resulting expressed polypeptide can then be purified, or partially purified, from such culture or component (e.g., from culture medium or cell extracts or bodily fluid) using known processes. While fractionation including but not limited to one or more steps of filtration, centrifugation, precipitation, phase separation, affinity purification, gel filtration, ion exchange chromatography, hydrophobic interaction chromatography (HIC; using such resins as phenyl ether, butyl ether, or propyl ether), HPLC, or some combination of above may be used herein, the advantageous methods of the present invention may employ LC fractionation and purification of the high molecular weight therapeutic proteins as described in U.S. Patent Application No. 60/548,302, Dillon et al. filed Feb. 27, 2004 and No. 60/538,982 Bondarenko et al., filed Jan. 23, 2004, (each incorporated herein by reference in its entirety).

The LC and LC/MS methods described herein below also may be combined with other purification methods, such as for example, purification of the polypeptide using an affinity column containing agents which will bind to the polypeptide; one or more column steps over such affinity resins as concanavalin A-agarose, Heparin-Toyopearl® or Cibacrom blue 3GA Sepharose®; one or more steps involving elution; and/or immunoaffinity chromatography. The polypeptide can be expressed in a form that facilitates purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. The polypeptide can be tagged with an epitope and subsequently purified by using a specific antibody directed to such epitope. One such epitope (FLAG®) is commercially available from Kodak (New Haven, Conn.). It is also possible to utilize an affinity column comprising a polypeptide-binding polypeptide, such as a monoclonal antibody to the recombinant protein, to affinity-purify expressed polypeptides. Other types of affinity purification steps can be a Protein A or a Protein G column, which affinity agents bind to proteins, that contain Fc domains. Polypeptides can be removed from an affinity column using conventional techniques, e.g., in a high salt elution buffer and then dialyzed into a lower salt buffer for use or by changing pH or other components depending on the affinity matrix utilized, or can be competitively removed using the naturally occurring substrate of the affinity moiety. In one embodiment of the invention, the preparation of recombinant protein may be partially purified over a Protein A affinity column.

Some or all of the foregoing purification steps, in various combinations, can also be employed to prepare an appropriate preparation of a recombinant IgG (i.e., the IgG1, IgG2, IgG3, or IgG4) for use in the methods of the invention, and/or to further purify such a recombinant polypeptide after contacting the preparation of the recombinant protein with a reduction/oxidation coupling reagent. The polypeptide that is substantially free of other mammalian polypeptides is defined as an "isolated polypeptide". The specific LC methods that may be combined with the redox reagent-based methods described herein are described in further detail in U.S. Patent Application No. 60/548,302, Dillon et al. filed Feb. 27, 2004 and No. 60/538,982 Bondarenko et al., filed Jan. 23, 2004, (each incorporated herein by reference in its entirety).

The polypeptide can also be produced by known conventional chemical synthesis. Methods for constructing polypeptides by synthetic means are known to those skilled in the art. The synthetically-constructed polypeptide sequences can be glycosylated in vitro.

The desired degree of final purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, and/or (if the polypeptide is radiolabeled) by auto radiography.

By "contacting" is meant subjecting to, exposing to, in solution. The protein or polypeptide can be contacted with the redox reagents while also bound to a solid support (e.g., an affinity column or a chromatography matrix). Preferably, the solution is buffered. In order to maximize the yield of protein with a desired conformation, the pH of the solution is chosen to protect the stability of the protein and to be optimal for disulfide exchange. In the practice of the invention, the pH of the solution is preferably not strongly acidic. Thus, some pH ranges are greater than pH 5, preferably about pH 6 to about pH 11, more preferably from about pH 7 to about pH 10, and still more preferably from about pH 7.6 to about pH 9.6. In one non-limiting embodiment of the invention, the optimal pH was found to be about pH 8.6. However, the optimal pH for a particular embodiment of the invention can be easily determined experimentally by those skilled in the art.

The reduction/oxidation coupling reagent is a source of reducing agents. Some reducing agents are free thiols. The reduction/oxidation coupling reagent is preferably comprised of a compound from the group consisting of reduced and oxidized glutathione, dithiothreitol (DTT), 2-mercaptoethanol, dithionitrobenzoate, cysteine and cystine/cystamine. For ease of use and economy, reduced glutathione and/or reduced cysteine can be used. It has to be noted that, at neutral pH, cysteine forms disulfides with itself generating cystine. The rate of this oxidation reaction increases in presence of oxygen, which is often present in solutions including the redox solutions used for refolding. Practically, a neutral pH solution, which initially contains only cysteine (reducing reagent), quickly produces cystine (oxidizing reagent). Therefore, redox coupling reagent can be introduced in the solution by adding only cysteine.

The redox reagent may be added to the fermentation media in which the cells producing the recombinant protein are grown. In additional embodiments, the reagents also may be added to the LC mobile phase during the LC separation step for separating the recombinant protein. In certain embodiments, the protein is immobilized to a stationary phase of the LC column and the redox and chaotrope are part of the mobile phase. In specific embodiments, the untreated IgG antibody may elute as a heterogeneous mixture as indicated by the number of peaks. The use of the reduction/oxidation coupling reagent and/or chaotropic agent produces a simpler and more uniform peak pattern. It is contemplated that this more uniform peak of interest may be isolated as a more homogeneous preparation of the IgG.

The reduction/oxidation coupling reagent is present at a concentration sufficient to increase the relative proportion of the desired conformation. The optimal absolute concentration and ratio of the reduction/oxidation coupling reagent depends upon the concentration of total IgG and in some circumstances the specific IgG subclass. When used for preparing IgG1 molecules it also will depend on the number and accessibility of the unpaired cysteines in the protein.

Generally, the concentration of free thiols from the reduction/oxidation coupling reagent can be from about 0.05 mM to about 50 mM, more preferably about 0.1 mM to about 25 mM, and still more preferably about 0.2 mM to about 20 mM.

In addition, the reduction/oxidation coupling reagent can contain oxidized thiols at approximately higher, equal or lower concentrations as the reduced thiol component. For example, the reduction/oxidation coupling reagent can be a combination of reduced glutathione and oxidized glutathione. It has been found that a ratio of reduced glutathione to oxidized glutathione of from about 1:1 to about 100:1 (reduced thiols:oxidized thiols) can function equally well. Alternatively in another embodiment, the reduction/oxidation coupling reagent can be cysteine or a combination of cysteine and cystine/cystamine. Thus, when oxidized thiols are included in the initial reduction/oxidation coupling reagent, the ratio of reduced thiols to oxidized thiols can in some embodiment be from about 1:10 to about 1000:1, more preferably about 1:1 to about 500:1, still more preferably about 5:1 to about 100:1 even more preferably about 10:1.

Contacting the preparation of recombinant protein with a reduction/oxidation coupling reagent is performed for a time sufficient to increase the relative proportion of the desired conformation. Any relative increase in proportion is desirable, including for, example, at least 10%, 20%, 30%, 40%, 50%, 60%, 70% and even 80% of the protein with an undesired conformation is converted to protein with the desired conformation. Typical yields that have been achieved with the methods of the invention range from 40 to 80%. The contacting may be performed by providing the redox reagent to the fermentation medium in which the protein is being generated. Alternatively, the contacting takes place upon partial purification of the protein from the cell culture in which it is generated. In still other embodiments, the contacting is performed after the protein has been eluted from the HPLC column but before any further processing. Essentially, the contacting may be performed at any stage during preparation, purification, storage or formulation of the antibody.

The contacting may be also performed with IgG antibodies attached to a stationary phase of a chromatographic columns, while the redox reagents and chaotropic reagents are a part of the mobile phase; In this case the contacting may be performed as a part of chromatographic purification procedure. Examples of representative chromatographic refolding processes may include size exclusion (SEC); solvent exchange during reversible adsorption on protein A column; hydrophobic interaction chromatography (HIC); immobilized metal affinity chromatography (IMAC); reversed-phase chromatography (RPC); use of immobilized folding catalyst, such as GroE1, GroES or other proteins with folding properties. The on column refolding is attractive because it is easily automated using commercially available preparative chromatographic systems. The refolding on column of recombinant proteins produced in microbial cell was recently reviewed in (Li et al., 2004).

If the contacting step is performed on a partially or highly purified preparation of recombinant protein, the contacting step can be performed for as short as about 1 hour to about 4 hours, and as long as about 6 hours to about 4 days. It has been found that a contacting step of about 4 to about 16 hours or about 18 hours works well. The contacting step can also take place during another step, such as on a solid phase or during filtering or any other step in purification.

The methods of the invention can be performed over a wide temperature range. For example, the methods of the invention have been successfully carried out at temperatures from about 4° C. to about 37° C., however the best results were achieved at lower temperatures. A typical temperature for contacting a partially or fully purified preparation of the recombinant protein is about 4° C. to about 25° C. (ambient), but can also be performed at lower temperatures and at higher temperature.

In addition, it is contemplated that the method may be performed at high pressure. Previously, high hydrostatic pressures (1000-2000 bar), combined with low, nondenaturing concentrations of guanidine hydrochloride below 1M has been used to disaggregate (solubilize) and refold several denatured proteins produced by *E-coli* as inclusion bodies that included human growth hormone and lysozyme, and b-lactamase (St John et al., Proc Natl Acad Sci USA, 96:13029-13033 (1999)). B-lactamase was refolded at high yields of active protein, even without added GdmHCl. In another study (Seefeldt et al., Protein Sci, 13:2639-2650 (2004)), the refolding yield of mammalian cell produced protein bikunin obtained with high pressure modulated refolding at 2000 bas was 70% by RP HPLC, significantly higher than the value of 55% (by RP-HPLC) obtained with traditional guanidine hydrochloride "dilution-refolding". These findings indicate, that high hydrostatic pressure facilitates disruption of inter- and intra-molecular interactions, leading to protein unfolding and disaggregation. The interaction of the high pressure on protein is similar to the interaction of proteins with chaotropic agents. Thus, it is contemplated that in the methods of the invention, instead of using chaotropic agents, high pressure is used for protein unfolding. Of course, a combination of high pressure and chaotropic agents also may be used in some instances.

The preparation of recombinant protein can be contacted with the reduction/oxidation coupling reagent in various volumes as appropriate. For example, the methods of the invention have been carried out successfully at the analytical laboratory-scale (1-50 mL), preparative-scale (50 mL-10 L) and manufacturing-scale (10 L or more). Thus, the methods of the invention can be carried out on both small and large scale with reproducibility.

In certain embodiments, the proteins produced using media contain redox reagents are further processed in a separate processing step which employs chaotropic denaturants such as, for example, sodium dodecyl sulfate (SDS), urea or guanidium hydrochloride (GuHCl). Significant amounts of chaotropic agents are needed to observe perceptible unfolding. In some embodiments the processing step uses between 0.1M and 2 M chaotrope that produces an effect equivalent to the use of 0.1 M to 2M guanidine hydrochloride. In a specific embodiment, the oxidative refolding is achieved in the presence of approximately 1.0 M guanidine hydrochloride or an amount of other chaotropic agent that produces the same or similar amount of refolding as 1M guanidine hydrochloride. In some embodiments, the methods use between about 1.5 M and 0.5 M chaotrope.

Figure 36:
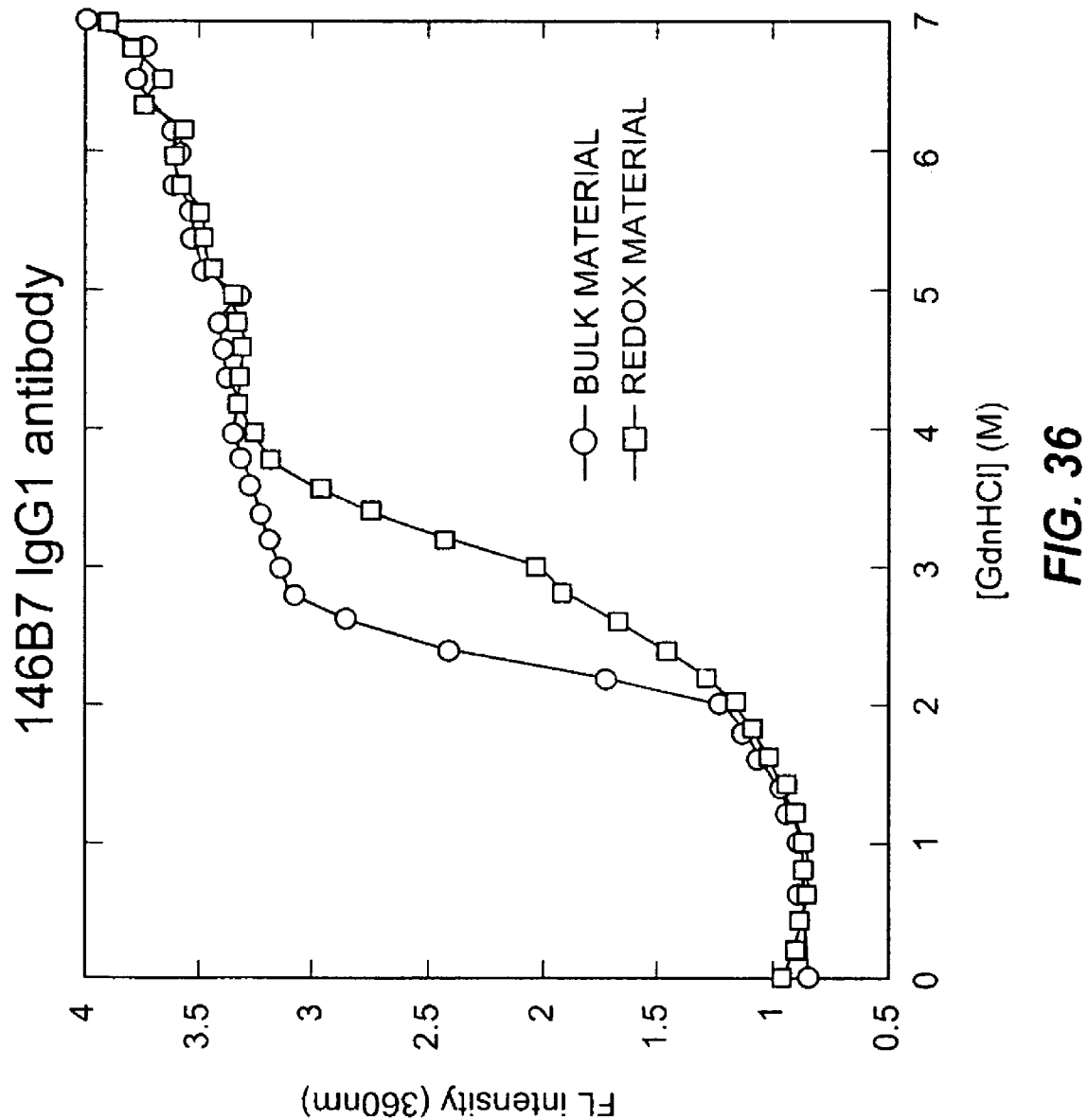
FIG. 36. GdnHCl equilibrium denaturation of bulk and redox treated CHO-derived 146B7 IgG1 antibody monitored by Fluorescence emission at 360 nm. Redox treated 146B7 IgG1 antibody is more stable to chemical denaturant as indicated by a shift in the Cm value of roughly 0.7M GdnHCl. Lines are drawn to guide the eye and do not represent fits of the data.

The amount of chaotropic agent used is based on the structural stability of the protein in the presence of the said chaotrope. One needs to have enough chaotrope present to perturb the local tertiary structure and/or quarternary structure of domain interactions of the protein, but less than that required to fully unfold secondary structure of the molecule and/or individual domains. To determine the point at which a protein will start to unfold by equilibrium denaturation, one practiced in the art would titrate a chaotrope into a solution containing the protein and monitor structure by a technique such as circular dichroism or fluorescence (FIG. 36).

There are other parameters that could be used to unfold or slightly perturb the structure of a protein that may be used instead of a chaotrope. Temperature and pressure are two fundamental parameters that have been previously used to alter the structure of a protein and may be used in place of a chaotropic agent while contacting with a redox agent. The inventors contemplate that any parameter that has been shown to denature or perturb a protein structure may be used by someone practiced in the art in place of a chaotropic agent.

Disulfide exchange can be quenched in any way known to those of skill in the art. For example, the reduction/oxidation coupling reagent can be removed or its concentration reduced through a purification step, and/or it can be chemically inactivated by, e.g., acidifying the solution. Typically, when the reaction is quenched by acidification, the pH of the solution containing the reduction/oxidation coupling reagent will be brought down below pH 7. In some embodiment, the pH is brought to below pH 6. Generally, the pH is reduced to between about pH 2 and about pH 6.

Determining the conformation of a protein, and the relative proportions of a conformation of a protein in a mixture, can be done using any of a variety of analytical and/or qualitative techniques. If there is a difference in activity between the conformations of the protein, determining the relative proportion of a conformation in the mixture can be done by way of an activity assay (e.g., binding to a ligand, enzymatic activity, biological activity, etc.). Biological activity of the protein also could be used. Alternatively, the binding assays can be used in which the activity is expressed as activity units/mg of protein.

If the two conformations resolve differently during separation techniques such as chromatography, electrophoresis, filtering or other purification technique, then the relative proportion of a conformation in the mixture can be determined using such purification techniques. For example, at least two different conformations of the recombinant IgG could be resolved by way of hydrophobic interaction chromatography. Further, since far UV Circular Dichroism has been used to estimate secondary structure composition of proteins (Perczel et al., 1 991, Protein Engrg. 4:669-679), such a technique can determine whether alternative conformations of a protein are present. Still another technique used to determine conformation is fluorescence spectroscopy which can be employed to ascertain complementary differences in tertiary structure assignable to tryptophan and tyrosine fluorescence. Other techniques that can be used to determine differences in conformation and, hence, the relative proportions of a conformation, are on-line SEC to measure aggregation status, differential scanning calorimetry to measure melting transitions (Tm's) and component enthalpies, and chaotrope unfolding. In some embodiments described in detail herein below the invention uses LC/MS detection to determine the heterogeneity of the protein.

By the term "isolating" is meant physical separation of at least one component in a mixture away from other components in a mixture. Isolating components or particular conformations of a protein can be achieved using any purification method that tends to separate such components. Accordingly, one can perform multiple chromatography steps in addition to the RP-HPLC described below, including but not limited to HIC, hydroxyapatite chromatography, ion exchange chromatography, affinity, and SEC. Other purification methods are filtration (e.g., tangential flow filtration), electrophoretic techniques (e.g., electrophoresis, electroelution, isoelectric focusing), and phase separation (e.g., PEG-dextran phase separation), to name just a few. In addition, the fraction of the preparation of recombinant protein that contains the protein in the undesired conformation can be treated again in the methods of the invention, to further optimize the yields of protein with the desired conformation.

The invention also optionally encompasses further formulating the proteins. By the term "formulating" is meant that the proteins can be buffer exchanged, sterilized, bulk-packaged and/or packaged for a final user. For purposes of the invention, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption. Such compositions can comprise an effective amount of the protein, in combination with other components such as a physiologically acceptable diluent, carrier, and/or excipient. The term "pharmaceutically acceptable" means a non-toxic material that does not interfere with the effectiveness of the biological activity of the active ingredient(s). Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. In addition, sterile bulk forms and sterile unit forms may contain a small concentration (approximately 1 microM to approximately 10 mM) of a reduction/oxidation coupling reagent (e.g., glutathione, cysteine, etc.). The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in Remington's Pharmaceutical Sciences, 16th ed. 1980, Mack Publishing Company, Easton, Pa. In addition, such compositions can be complexed with polyethylene glycol (PEG), metal ions, and/or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. Such compositions will influence the physical state, solubility, stability, rate of in vivo release, and rate of in vivo clearance, and are thus chosen according to the intended application, so that the characteristics of the carrier will depend on the selected route of administration. Sustained-release forms suitable for use include, but are not limited to, polypeptides that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

The methods of the present invention are useful for the analysis of recombinant IgG (e.g., IgG1, IgG2, IgG3, or IgG4) proteins, and are particularly useful for analysis of such high molecular weight proteins. The methods are also useful for the analysis of protein monomers of high molecular weight and protein heteromultimers, e.g., antibodies. It is contemplated that these proteins will contain post-translational modifications, such as oligosaccharide moieties and the like. In specific embodiments, the methods of the present invention are used for the analysis of antibodies and antibody domains. In one example, the methods are used for the analysis of proteins having a molecular weight greater than 90 kDa, including intact antibodies, any tertiary protein structure having a molecular weight greater than 90 kDa. It is to be understood that the molecular weight is calculated based on amino acid sequence and includes the known post-translational modifications of the protein; e.g., carbohydrate modification. The methods are applied to characterize the oligosaccharide composition, cleavage, dimer or multimer formation and oxidation of the proteins, structural variants with different disulfide structures, and/or specific amino acids within the protein.

In some embodiments, the methods of the invention are used to analyze antibodies and antibody fragments. The sample to be analyzed may comprise an intact antibody comprising an Fc domain and two Fab domains. Alternatively, the methods of the invention are employed to analyze the structure of a portion of an antibody such as for example an $F_C$ domain or one or both of the Fab domains. It is particularly contemplated that the methods of the invention will be useful in the analysis of the products of partial cleavage of an intact antibody. Such cleavage may be performed prior to the RP-HPLC separation. Typical proteolysis will be performed with the use of an enzyme e.g., papain, lyc-C protease or pepsin to yield cleavage of the antibody at the hinge region. Alternatively, the cleavage may employ a reducing agent to reduce the disulfide bonds that connect the two chains of an antibody structure. Such reduction may be achieved using e.g., dithiothreitol, mercaptoethanol, tributylphosphine, and tri(2-carboxyethyl)phosphine hydrochloride. For a review of analytical and preparative methods used in the preparation of antibodies and fragments thereof, those of skill are referred to Josic and Lim: Methods for Purification of Antibodies, *Food Technol. Biotechnol.* 39 (3) 215-226 (2001).

In exemplary embodiments, the limited proteolysis is achieved using endoproteinase Lys-C from a range of 10 to 60 minutes at a pH range of 7.0 to 8.0. The digestion is performed without denaturation at 37° C. with a molar enzyme:protein ratio of 1:150. This produces a few large fragments of the antibody without undue clipping of the protein. The limited proteolysis products are then subjected to RP-HPLC/MS methods described herein. Using this limited proteolysis Fab and Fc fragments at the hinge region of an IgG1 were generated. These methods allowed the detection of a +16 Da increase in the mass of the fragments due to an oxidation of a methionine residue and the detection of a +2 Da increase due to incomplete disulfide bond formation.

The methods of the invention may be used to analyze native proteins, fusion proteins, humanized antibodies, chimeric antibodies, human antibodies, single chain antibodies and the like. In one example, the methods can also be used to analyze any antibody or a fragment thereof that may be as small as 40 kDa, 50 kDa, 55 kDa, 60 kDa, 65 kDa, 70 kDa, 75 kDa, 80 kDa, 85 kDa or greater. In some embodiments, the antibody loaded onto the RP-HPLC column is an intact Fab region. In other embodiments, the antibody being analyzed is an (Fab)$_2$ region generated by cleavage of the Fc region of the antibody. Analogously, the methods of the invention also may be used to analyze the Fc region of an antibody generated from such cleavage. In specific embodiments, the antibody being analyzed comprises an intact Fc region and only one intact Fab region. In addition the methods of the invention are used to analyze a protein comprising an antibody Fc region and additional peptides attached thereto, or a protein comprising an Fab region of antibody with additional peptides attached thereto.

The methods of the present invention may be used to analyze recombinant antibodies. Recombinant antibodies can either contain an Fc domain or not contain an Fc domain. In particular, multivalent antibodies may be analyzed using the present invention. As used herein "multivalent antibodies" are recombinant antibody-like molecules that contain binding domains for more than one epitope. For example, such antibody-derived proteins include molecules in which an antibody Fab chain has been fused to binding domains e.g., (Fab-scFv bibodies or tribodies). These molecules are useful intermediate weight recombinant bispecific antibodies that do not containing an Fc portion. Producing antibodies that lack the Fc domain is advantageous because the presence of such a domain on an antibody-related therapeutic molecule tends to increase the serum persistence time of the molecule by protecting it from metabolism in the liver and can also crosslink other cells via its interaction with the Fc receptor, thereby giving rise to toxic side effects due to systemic triggering of immune effector cells. Thus, certain antibody related therapeutic molecules lack the Fc domain. Those of skill in the art are aware of methods to engineer such antibody-related molecules. For example, recombinant antibodies may be produced from a combination of antibody derived building blocks (such as Fc, (Fab')2, Fab, scFv, diabody) with heterodimerizing motifs in order to efficiently create multispecific antibodies.

The methods of the invention are particularly useful in determining the integrity of an antibody and in particular a therapeutic antibody. The antibody is separated and analyzed using the RP-HPLC/MS methods described herein in order to determine the presence of antibody degradation products. The methods described herein allow those skilled in the art to assess the presence of dimers, antibody cleavage products, deamidation, presence of oxidation or formation of N-terminal pyroglutamic acid or scrambling of disulfide bonds of the antibody. These characteristics are all degradations that occur in an antibody and diminish the structural integrity of the antibody.

The methods demonstrated in the examples herein below show the improved chromatographic separation and accurate molecular weight measurements of pharmaceutical antibodies and their degradation products. The method utilizes a high resolution high precision mass spectrometer capable of measuring mass difference between two variants of an antibody that differ by one amino acid residue (e.g., glycine 57 Da) or one sugar moiety (e.g., galactose 162 Da). The mass resolution of the spectrometer should be at least 3000 for a typical IgG antibody with molecular weight of 150 kDa. The mass resolution is calculated as:

$$\text{Resolution} = MW/\Delta MW = 150 \text{ kDa}/57 \text{ Da} \approx 3000$$

In certain embodiments, the methods of the present invention are able to detect the change in mass of an antibody or protein of greater than 100 kDa before and after oxidation, i.e., a mass difference of 16 Da. This produces a mass resolution of 10,000 for a typical antibody. The methods of the invention are further illustrated in the examples below.

EXAMPLES

The following examples are included to demonstrate some embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

U.S. Provisional Application No. 60/621,295 (incorporated herein by reference) provides a disclosure of refolding of an IgG2 molecule in the presence of reduction/oxidation agents, and optionally, chaotropic agents. The biological activity of such a refolded IgG2 was six time higher than the IgG2 refolded without a chaotropic agent and was three to four times higher than IgG2 bulk antibody that has been prepared without the use of redox agents to produce refolding of the protein. According to the aforementioned application, using the refolded IgG2, it will be possible to deliver a larger effective dose of the IgG2, whilst using less amount of protein. Such a reduction in the overall amount of protein that is needed to produce a biologically effective response will be advantageous because reducing the amount of such a protein that must delivered to an animal will be likely to produce less of an adverse reaction when delivered e.g., by intravenous or subcutaneous injection.

The following Examples provide exemplary embodiments for achieving advantageous refolding of recombinant IgG molecules.

Example 1

Discussion of Refolding of Proteins

Refolding of proteins produced in *E. coli*. Advances in refolding of proteins produced in *E. coli* were recently reviewed by Rudolph and coworkers (Lilie et al., 1998; Rudolph and Lilie, 1996). The authors pointed that protein folding is one of the most complicated mechanism in the machinery of the protein production and "the specific conditions regarding buffer composition, protein concentration, temperature, and so on, has to be optimized for every protein." The incorrect disulfide bonds is one of the problems. One mean "to enhance correction of incorrect disulfide bonds in the periplasm of *E. coli* is to over express the endogenous periplasmic DsbC protein, which is a disulfide isomerase. Another way is cultivation in the presence of thiol reagents, which lead to reshuffling of incorrect disulfide bonds, has been proven to enhance the yield of native proteins containing multiple disulfide bonds (Glockshuber et al., Verbesserung der ausbeute bei der sekretion von disulfidverbruchten proteinen. [U.S. Pat. No. 0,510,658 B1], 1992; Wunderlich et al., J. Biol. Chem., 268:24547-24550, 1993). Several other patents related to protein refolding are sited in (Lilie et al., Curr. Opin. Biotech., 9:497-501, 1998). It was also shown that prosequence facilitates folding of several proteins including human nerve growth factor (Rattenholl et al., Eur. J. Biochem., 268:3296-3303, 2001) from *Escherichia coli* inclusion bodies.

Folding intermediates of murine monoclonal IgG antibodies. The folding pathways of a murine antibody of subclass k/IgG1 were investigated in (Lilie et al., J. Mol. Biol., 248: 190-201, 1995b) including domain folding, association through disulfide bonding and prolyl cis/trans isomerization. The study identified that in Fab renaturation, the folding reaction after association of Fd and light chain is determined by prolyl isomerization. At least four folding intermediates have to be assumed according to the folding stage of light chain and the configuration of at least one prolyl-peptide bond. Pro159 within the Fd fragment may be responsible for the observed slow folding phase and may require the quaternary but not the tertiary structure to facilitate the isomerization (Lilie et al., J. Mol. Biol., 248:190-201, 1995b). For the same Fab antibody fragment, domain-domain interactions were found to be a rate-limiting step of folding, thus accumulating folding intermediates at a late step of folding (Lilie et al., Protein Sci., 4:917-924, 1995a). Earlier, Lilie et al (Lilie et al., Protein Sci., 2:1490-1496, 1993) show that several members of prolyl isomerases (PPIs) accelerated the in-vitro refolding process of an antibody Fab fragment and increased the yield of correctly folded molecules. They acted as catalysts of protein folding by accelerating the time-limited isomerization of Xaa-Pro peptide bond (Lilie et al., Protein Sci., 2:1490-1496, 1993).

An alternatively folded state of murine monoclonal IgG antibodies. An alternatively folded state that is different from the native states have been described for monoclonal IgG antibodies with intact disulfide bonds (Buchner et al., Biochemistry, 30:6922-6929, 1991; Welfle et al., Biochim. Biophys. Acta, 1431:120-131, 1999). This conformational state is reportedly formed upon incubation of either the native or the denatured IgG molecule at acidic pH (<3). This A-state is characterized by a high degree of secondary structure, increased hydrophobicity, increased stability against denaturant and thermal unfolding and existence of tertiary structure (Buchner et al., Biochemistry, 30:6922-6929, 1991). It was found (Buchner et al., J. Biol. Chem., 318:829-836, 2002), that both the reduced Fab fragment of the murine monoclonal antibody and its reduced light chain formed a specific, stable, but non-native structure at low pH. It is interesting that apparent stability of the alternatively folded state of the reduced light chain is higher than that of the oxidized light chain, suggesting that the intradomain disulfides, which are critical for the stability of the native state, destabilize the alternatively folded state (Buchner et al., J. Biol. Chem., 318:829-836, 2002). Interactions between the light and heavy chains, stabilized by the interchain disulfide within the Fab fragment, were found essential for formation of the alternatively folded state (Lilie et al., FEBS Lett., 362:43-46, 1995). Welfe et al. found that lowering pH to between pH 3.4 and 2.0 induced conformational changes and the formation of new structure and suggested, that desorpotion from affinity columns should be performed at pH 3.5 or above (Welfle et al., Biochim. Biophys. Acta., 1431:120-131, 1999).

Refolding of immunoglobulin-folded proteins using GndHCl and L-arginine. Influence of additives, such as GnHCl, glutathione, L-arginine, on refolding immunoglobulin-folded proteins was discusses in (Umetsu et al., J. Biol. Chem., 278:8979-8987, 2003). Spontaneous folding at the 1 m GndHCl resulted in a structure in which a correct disulfide bonding was achieved; however, the addition of L-arginine resulted in the formation of a partially folded intermediate without disulfide linkages (Umetsu et al., J. Biol. Chem., 278:8979-8987, 2003).

Example 2

Recognition of Structural Heterogeneity in Human Monoclonal IgG2 Antibodies

X-ray crystallography pictures of human IgG1 antibodies have been published in several reports (Saphire et al., Science, 293:1155-1159, 2001; Saphire et al., J. Mol. Biol., 319:9-18, 2002). For example, Saphire et al., (2001), showed an X-ray crystallography trace of human IgG1 b12 antibody. However, to date there has been no resolution of the X-ray crystal structures of IgG2 antibody. The present invention shows that human IgG2 antibodies posses structural heterogeneity, and such heterogeneity may be responsible for the difficulties in producing an X-ray crystallographic data for IgG2.

Figure 2A:
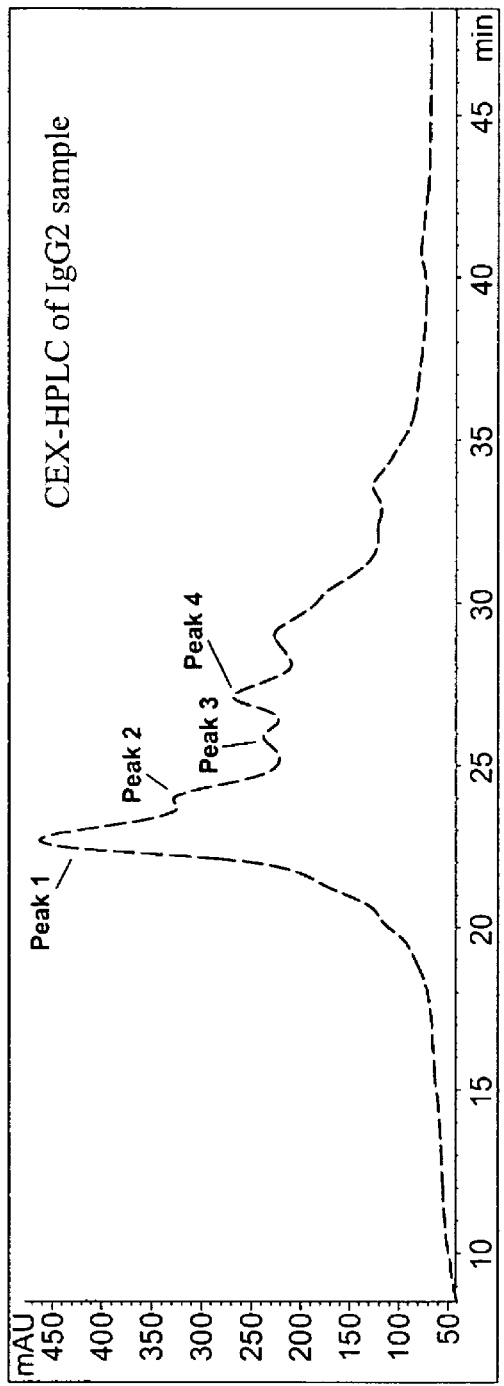
FIG. 2 shows (A) cation exchange CEX of whole IgG2 sample and (B) reversed-phase chromatograms of the same whole IgG2 sample and collected CEX fractions.

Data from reversed-phase (RP) HPLC/MS and cation-exchange (CEX) HPLC methods experiments showed that all studied humanized IgG2 antibodies show multiple peaks on RP and CEX chromatograms, while IgG1 antibodies elute as single peak. FIG. 1 shows RP chromatograms of recombinant human antibodies with the same CDRs implemented in IgG1 and IgG2 modalities. The amino acid sequences have 95% homology between these two molecules, but RP chromatogram again are different and contain multiple peaks for IgG2 and a single peak for IgG1. CEX chromatography of IG2 shows similar profile of peaks as compared to RP chromatograph (FIG. 2). After the collected CEX fractions were re-injected on the RP column, they co-eluted with the RP peaks of the whole IgG2 sample (FIG. 2).

Figure 3A:
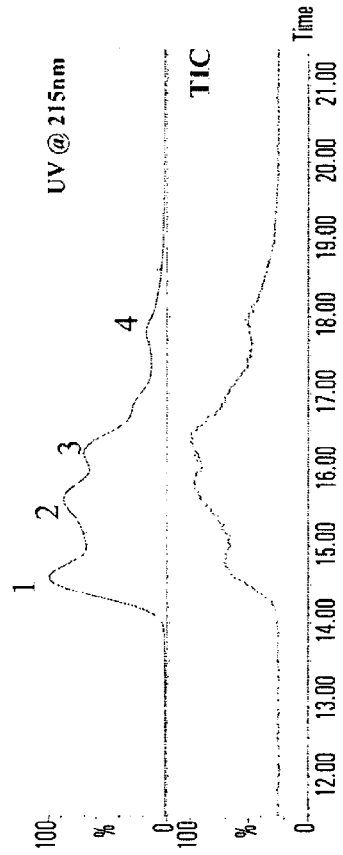
FIG. 3A shows reversed phase chromatogram of IgG2 detected using absorbance at UV 215 nm and total ion current (TIC) of mass spectrometer. 3B shows electrospray ionization mass spectra of IgG2 structural variants eluted from RP column as peaks 1, 2, 3, and 4 from FIG. 3A.
Figure 3B:
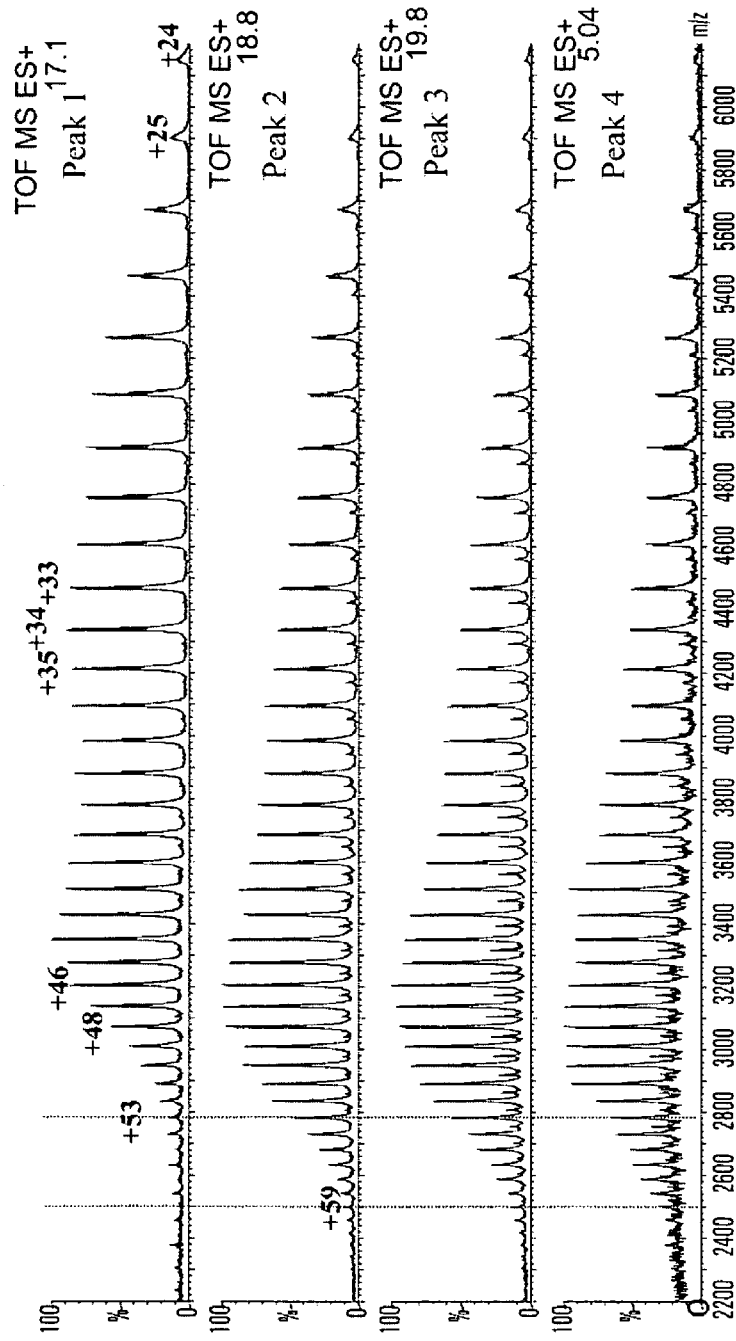

A high resolution Micromass/Waters Q-TOF mass spectrometer was used to obtain mass spectra of the peaks separated by RP HPLC. FIG. 3A shows RP chromatogram of IgG2 antibody detected by using both, absorbance of LW at 215 nm and total ion current of the mass spectrometer. The figure indicates that peak 1 produces less mass spec current as compared to other peaks. FIG. 3B indicates that IgG2 ions eluting in peaks 1 contain maximum of 53 protons on the surface of the ion giving the ion 53 positive charges. IgG2 molecular ions of peak 1 accommodate approximately 6 protons less than the other IgG2 molecules eluting as peaks 2, 3, and 4, which indicates that peak 1 contain IgG2 molecules, which are more compactly folded as compared to other eluting molecules of this sample. The fewer-charges-on-the-surface ions of peak 1 also produce smaller TIC signal (FIG. 3A). On the other hand, deconvoluted electrospray ionization mass spectra reveal that all IgG2 isoforms separated by RP HPLC have the same molecular weight (MW) values within the mass precision of the instrument of ±2 Da. This finding eliminates possibility of most of the reported structural modifications of IgG antibodies. After reduction and alkylation, the RP chromatography for both IgG1 and IgG2 antibodies produce narrow peaks for light and heavy chains without heterogeneity. The fact that reduction eliminates the heterogeneity indicates that it is disulfide-connectivity related.

Figure 4:
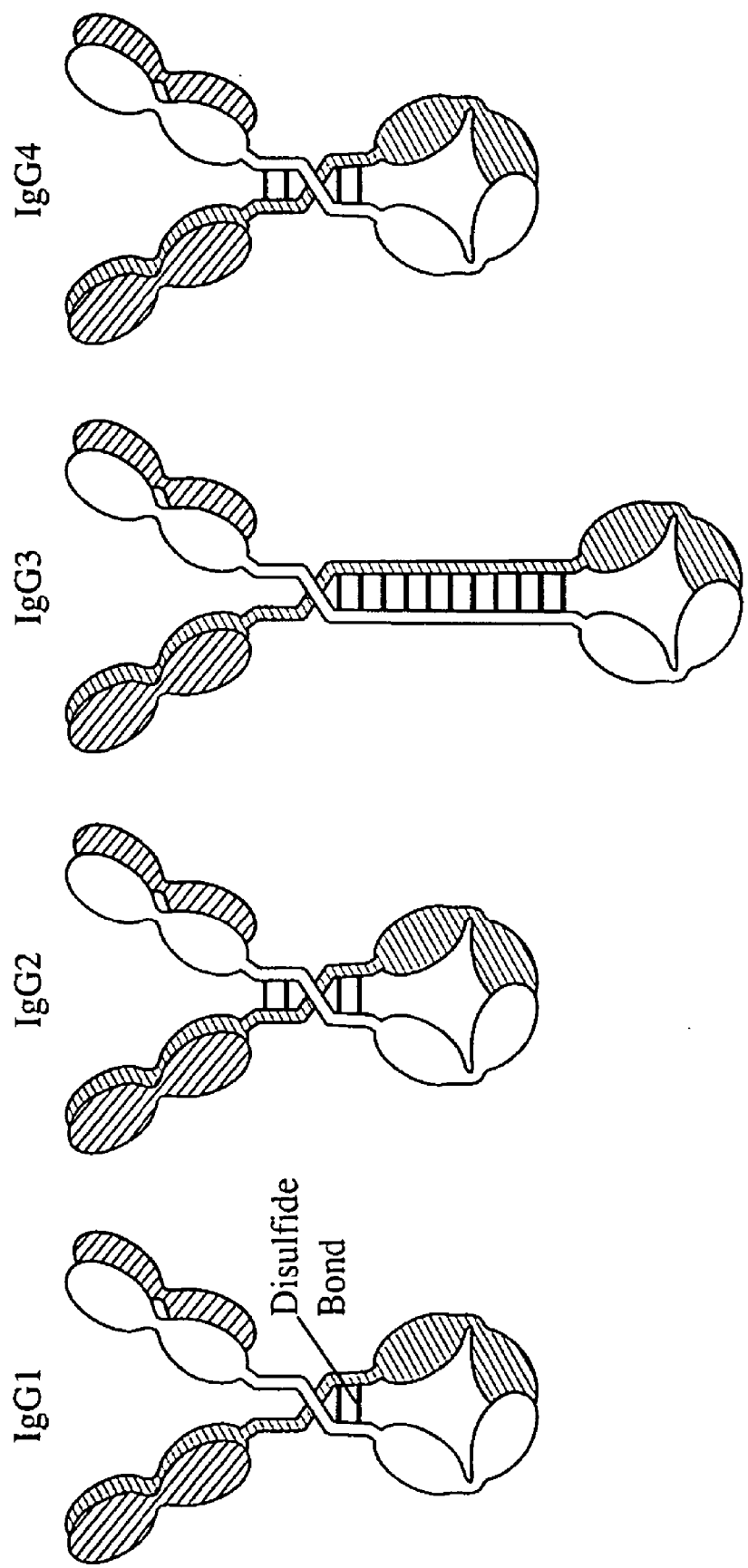
FIG. 4 shows the four subclasses of human IgGs. Adopted form Kuby Chapter 4, Immunoglobulins: Structure and function.
Figure 43:
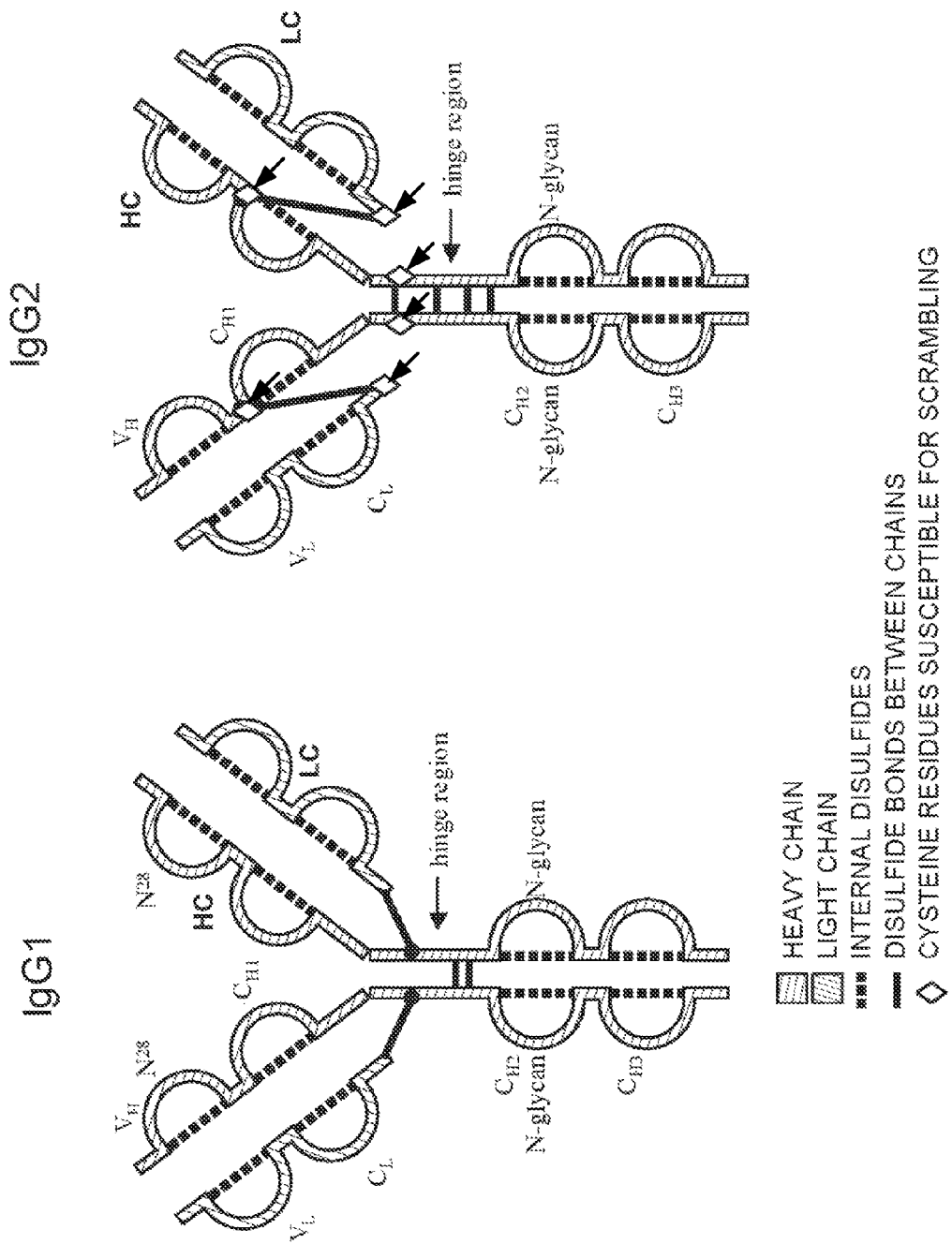
FIG. 43. Schematics of IgG1 and IgG2 antibodies. IgG2's have a unique attachment of the light chain and have two additional inter-chain disulfides in the hinge region. Legend: vertical diagonal lines=heavy chain (HC); horizontal diagonal lines=light chain (LC); dotted line=internal disulfides; solid line=disulfide bonds between chains; diamonds with arrows=cysteine residues susceptible to scrambling.

The IgG1 and IgG2 subclasses of antibodies are different by the structure of hinge region, which includes two interchain disulfide bonds in IgG1 and four in IgG2 (FIGS. 4 and 43). The above studies strongly suggest that multiple IgG2 isoforms are populated by molecules with different disulfide bond connectivity in the hinge region.

Figure 5:
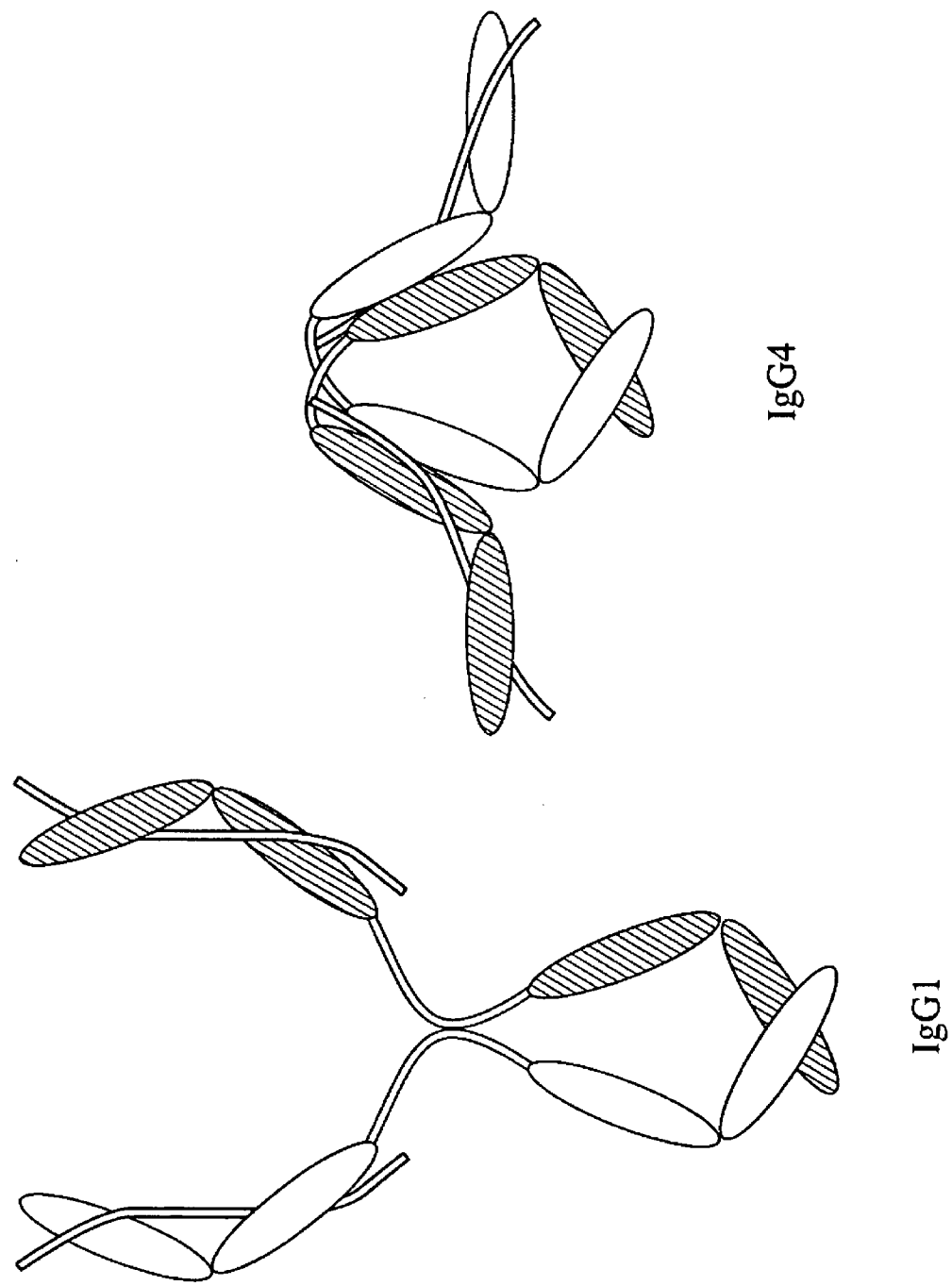
FIG. 5 shows the proposed IgG1 and IgG4 structures. Note that the structure of IgG4 is more compact than the structure of IgG1.

Analyzing the above-described results, the inventors concluded that IgG2 molecules have several structural variants, which differ by disulfide connectivity in the hinge region. FIG. 4, adopted from Kuby Chapter 4 Immunoglobulins: Structure and Function, 2002, shows all four subclasses of IgG antibodies in their conventional textbook configuration. In reality, a study by Aalberse and Schuurman (Aalberse et al., Immunology, 105:9-19, 2002) identified that in the preferred IgG4 configuration, CH1 regions interact with CH2 domains of this antibody (FIG. 5). FIG. 4 shows that IgG4 structures are very similar including the four disulfide links in the hinge region. There are differences in amino acid sequence of the hinge, so the configurations of IgG2 and IgG4 are not expected to be same, but may have similarities and, possibly, even fold as IgG4 antibody in FIG. 5.

Figure 6:
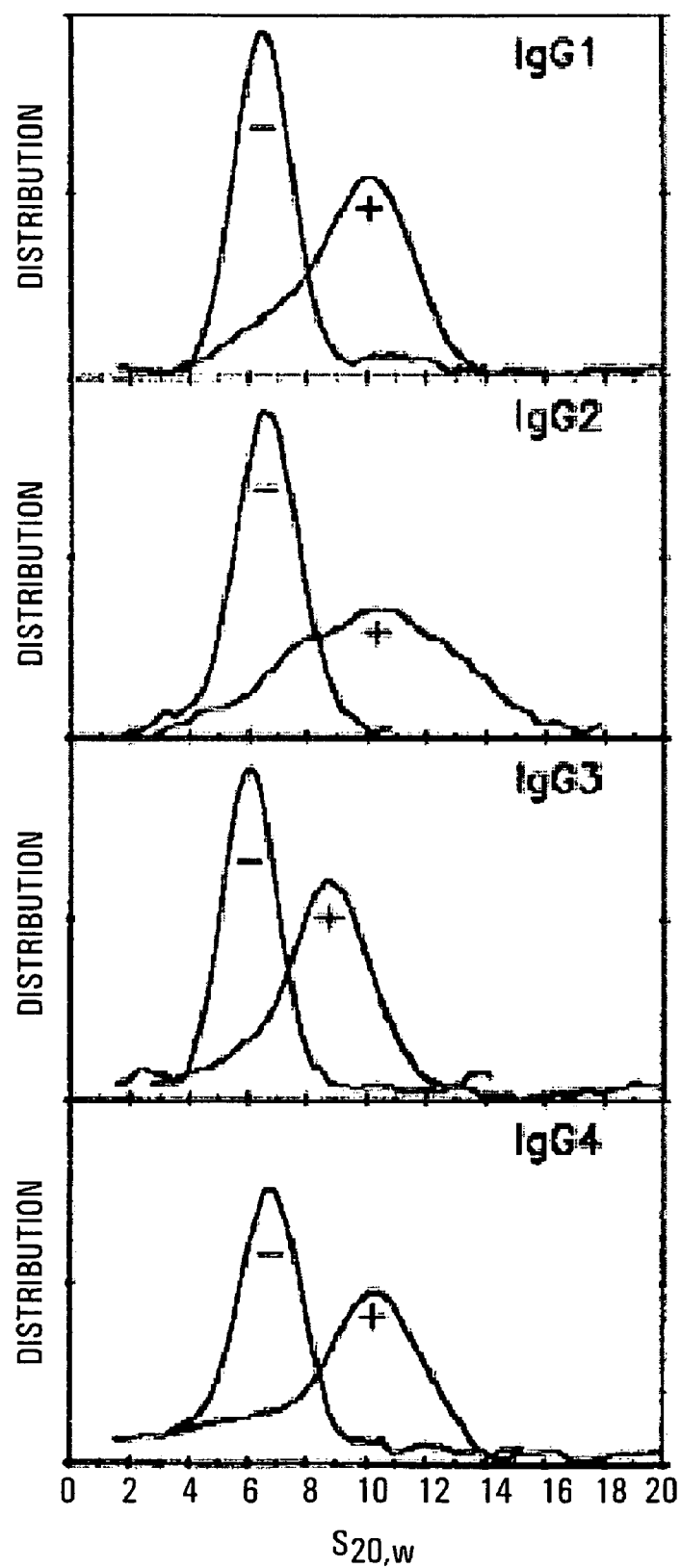
FIG. 6 shows the sedimentation data of chimeric IgG1, 2, 3 and 4 antibodies (Adopted from Phillips et al., Mol. Immunol., v. 31, p. 1201-1210, 1994.) The Figure legend in Phillips et al., noted that this figure shows: the sedimentation of chimeric immunoglobulins containing different human subclass regions in the presence and absence of bis-dansyl cadaverine. (A) integral scans of the immunoglobulins in the absence of bivalent hapten. Conditions of centrifugation were: IgG1 20° C., 52,000 rpm consecutive integral scans (280 nm) at 12 min intervals; IgG2 21.7° C., 52,000 rpm consecutive integral scans at 8 min intervals; IgG3 21.6° C., 52,000 rpm consecutive integral scans at 8 min intervals; IgG4 20.7° C., 52,000 rpm consecutive integral scans at 8 min intervals. (B) Integral scans of the immunoglobulins in the presence of equimolar bis-dansyl cadaverine. Conditions of centrifugation were: IgG1 21.7° C., 42,000 rpm, 12 min intervals; IgG2 21.4° C., 44,000 rpm, 8 min intervals; IgG3 21.7° C., 44,000 rpm, 12 min intervals; IgG4 21.7° C., 44,000 rpm, 12 min intervals. (C) Sedimentation coefficient distributions (uncorrect for diffusion) of the different subclasses in the absence (−) and presence (+) of equimolar bis-dansyl cadaverine.
Figure 7:
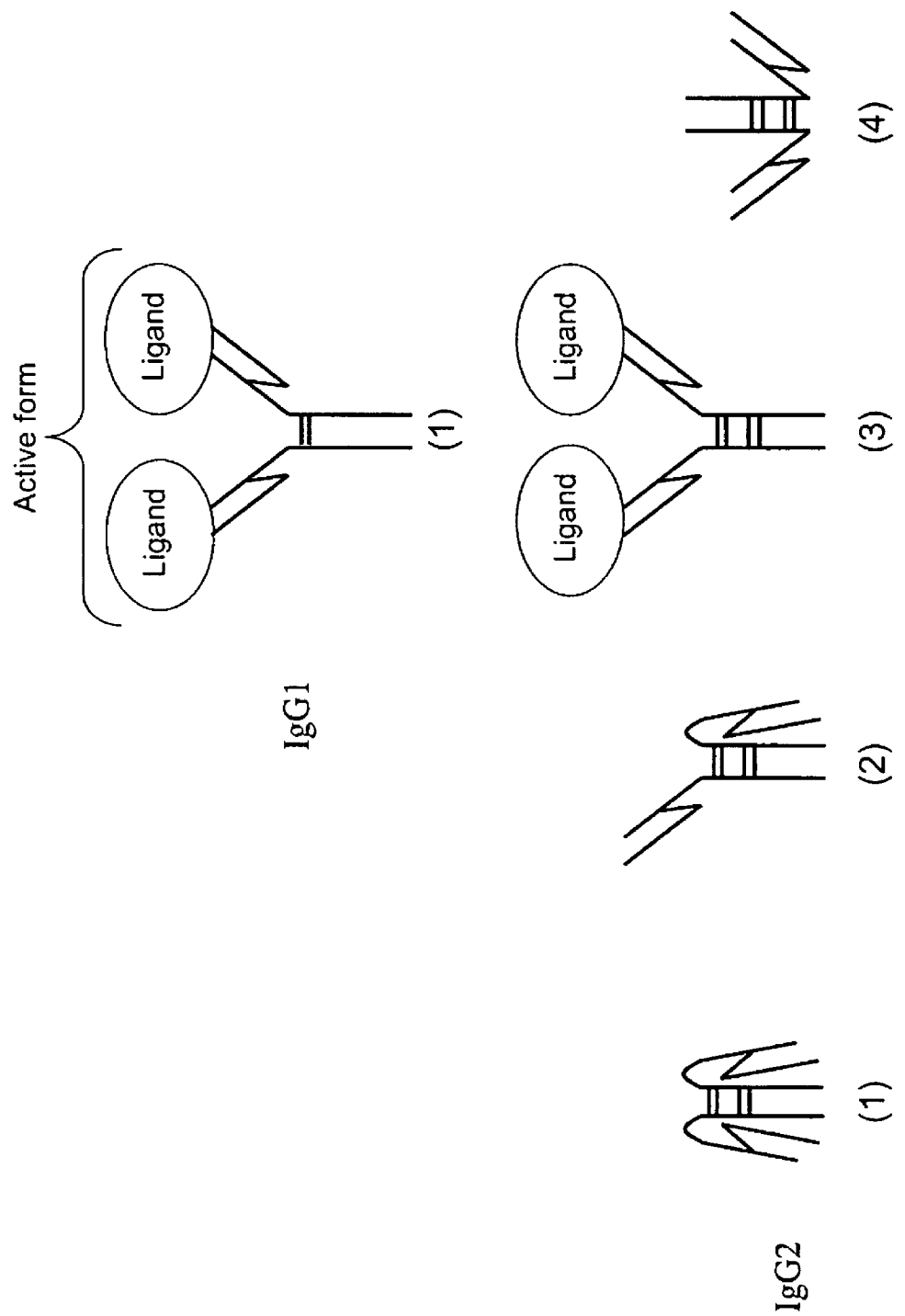
FIG. 7 shows structure of IgG1 antibody as compared to the proposed structure of IgG2 antibodies.

Another study by Phillips et al. (Phillips et al., Mol. Immun., 31:1201-1210, 1994), using electron microscopy and sedimentation analysis showed the distribution of shapes of IgG2 compare to other three subclasses of antibodies. The authors of that study observed "a distribution of complexes which was noticeably different from the other subclasses. Some circular dimmers, some linear dimmers and a large amount of monomer were seen. This was interpreted in terms of an energy barrier to ring closure arising from the orientation of the Fab arms of IgG2 probably leading to linear dimers as the predominate complex seen with the analytical ultra-centrifuge." The sedimentation data (FIG. 6) show partially resolved multiple peaks, further indicating that IgG2 molecules are structurally heterogeneous (Phillips et al., Mol. Immun., 31:1201-1210, 1994). In another article, Gregory et al (Gregory et al., Mol. Immun., 24:821-829, 1987) described the use of sedimentation and small angle X-ray scattering analysis of the subclasses of human IgG. According to the authors, "IgG1 is suggested to have a hinge length of 0-15 A and non-coplanar Fab arms; IgG2 to be effectively hingeless with folded-back Fab arms." The two sited above reports (Gregory et al., Mol. Immun., 24:821-829, 1987; Phillips et al., Mol. Immun., 31:1201-1210, 1994), suggest that IgG2 may have several conformational states, including the configuration with folded back Fab arms. FIG. 7 contains several structures of IgG2 antibody proposed by authors of the current report. FIG. 7 also contains, the corny reported structure of IgG1 antibody from the studies using X-ray crystallography.

Example 3

Refolding of IgG2 Antibodies in the Presence of Redox Reagents Reduces Structural Heterogeneity of IgG2 and Increases its Activity The above-described studies led to the idea of refolding the IgG2 antibody in order to verify its activity. The refolding was done by incubating the antibody in a cysteine-cystine containing buffer, at pH 8, 4° C. for 72 hours.

A preferred redox coupling system employed herein is the cysteine/cystine as reduction/oxidation coupling reagents. The starting material was a purified preparation of IgG2 antibody. Buffers were 0.1 M citrate or 0.2 M Tris at pH 8.5. Protein concentration of the IgG2 in the reaction was varied from 0.5 mg/mL to 10 mg/mL. In preferred examples the protein was varied from 2.5 mg/mL to 3 mg/mL.

The redox coupling system of L-cysteine (varying from 0 to 50 mM) was utilized and the procedure was assessed in the presence or absence of equal amounts of L-cystine and in the presence and absence of 1 mM EDTA. Incubation temperature was assessed at 4° C., 15° C., and 22° C. for 6, 18, and 48 hours. Treated preparations of recombinant protein were characterized by RP-HPLC as described in the Examples above and in the Figure legends of FIGS. 1 to 15 in Dillon et al., U.S. Provisional Application 60/621,295 and PCT/US05/001840.

It is determined that refolding readily occurs when the redox system contains from about 0.1 mM to about 10 mM cysteine and from about 0.1 nM to about 10 mM cystine. The cysteine/cystine may but need not be present in a 1:1 concentration ratio.

Figure 8:
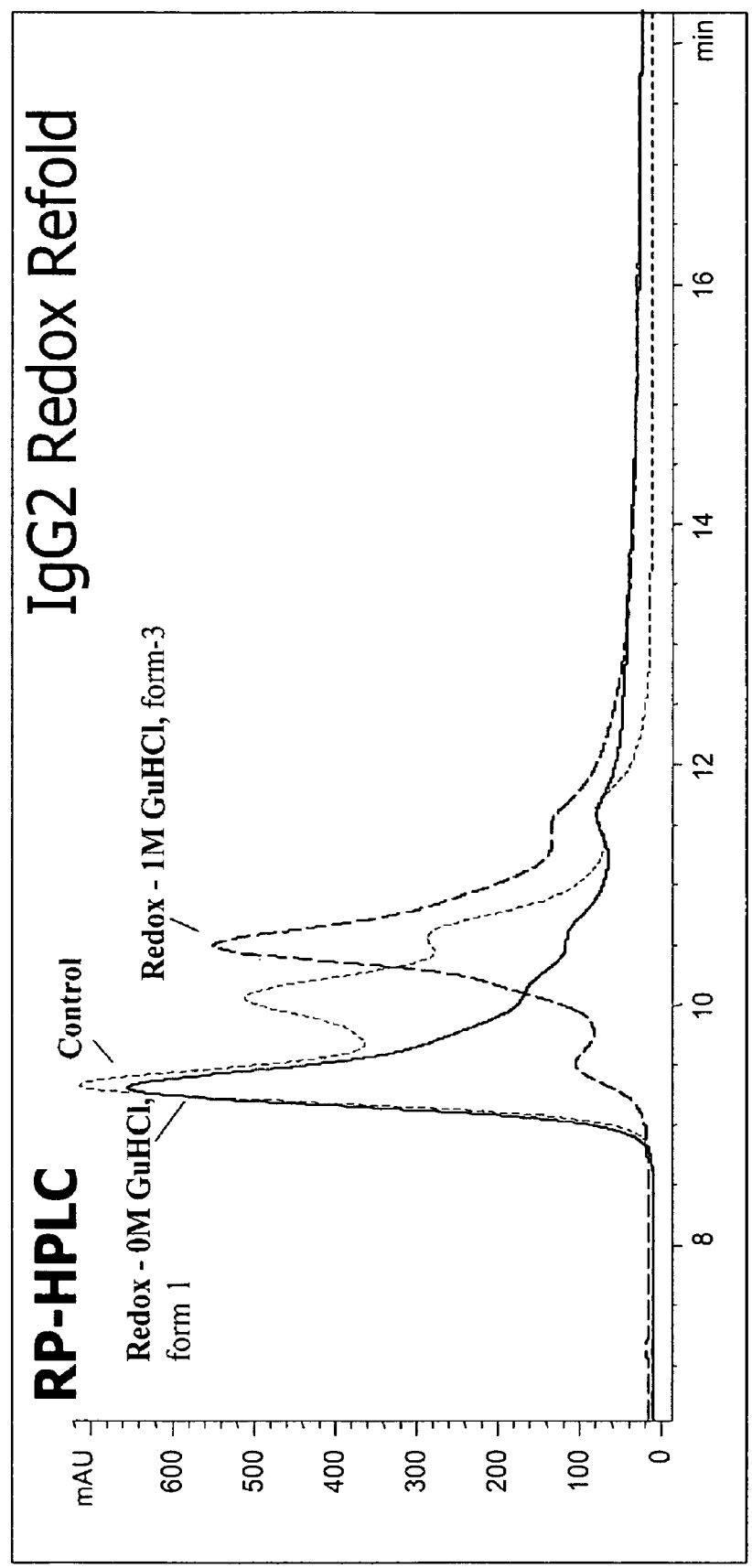
FIG. 8 shows the RP chromatograms of the two refolded IgG2 antibodies. Note that the refolded native form and the refolded in the presence of denaturing 0.89M guanidine hydrochloride aligned with the profile of the currently produced bulk IgG2 material. When four different IgG2 antibodies were refolded, again a similar pattern was seen in which the presence of cysteine/cystine for 48 hours at room temperature produced a uniform single peak, use of guanidine hydrochloride in the presence of cysteine/cystine for 48 hours at room temperature also produced a single peak which eluted later than the peak produced by cysteine/cystine treatment alone, whereas absence of treatment with cysteine/cystine produced a heterogeneous mixture containing multiple peaks associated with the IgG2 preparation.

In addition, the protocol included 0.9 M GndHCl in the buffer to slightly unfold-(relax) the structure during refolding/oxidation. FIG. 8 shows results of the two refolding experiments. The results indicate, that the two refolded sample of IgG2 antibody are homogenous in structure and co-elute with peaks 1 and 3 of the RP chromatograph elution profile.

Figure 52:
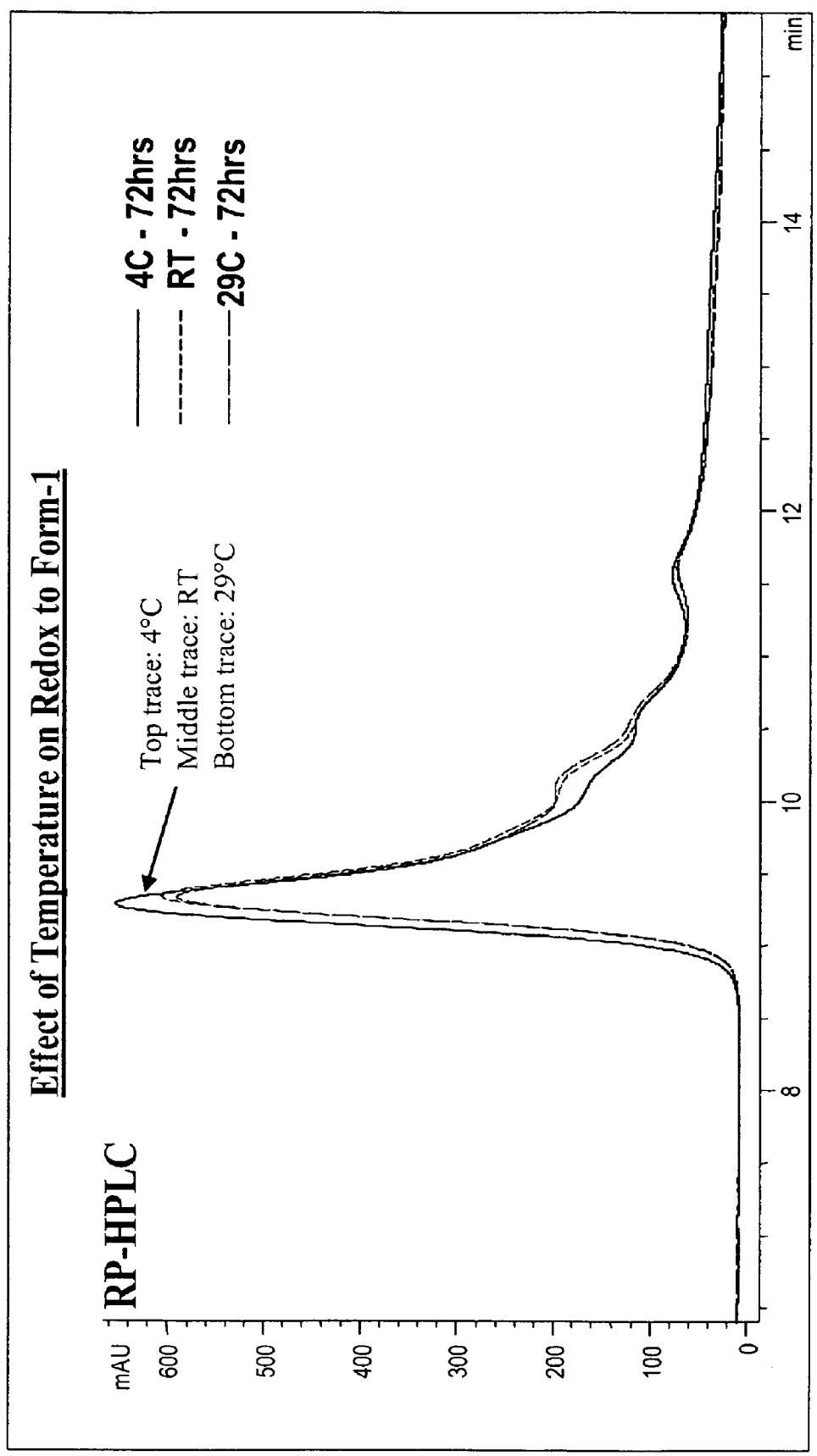
FIG. 52. Reversed phase chromatograms displaying the effect of incubation temperature during redox treatment of an IgG2 (anti IL-1R) antibody.

Yet another redox coupling system that may be used is one in which reduced glutathione and glutathione (GSH/GSSG at a ratio of 10:1) is added at varying concentrations of from 0.1 to 5 mM GSH. The effect of pH and temperature of incubation in the presence of this redox coupling agent may be assessed. pH may be varied from pH 5 to pH 9. Incubation temperature may be varied at 4° C., 22° C. or 31° C. In other embodiments, the temperature at which the IgG2 was incubated in the GSH/GSSG redox coupling system was varied. The refolding is more efficient at 4° C. than at room temperature (FIG. 52).

Figure 47:
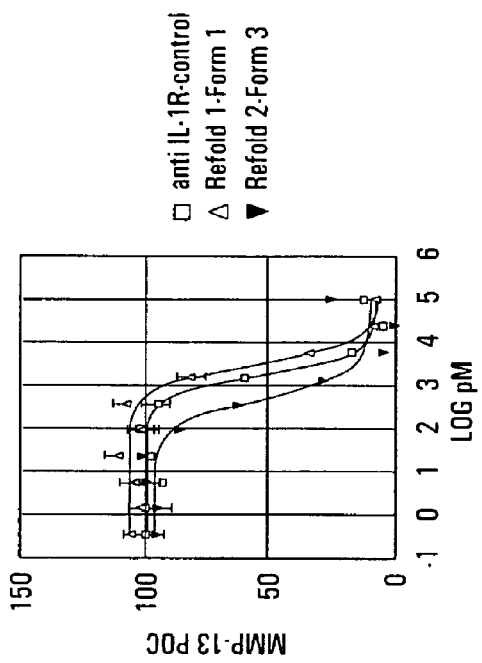
FIG. 47. Bioassay curves for anti IL-1R IgG2 antibody, native redox (Form 1), and GuHCl redox (Form 3) material. Dramatic differences were seen in the biological activity of the oxidative refold material. The assays were repeated over three days providing good statistical confidence.
Figure 47:
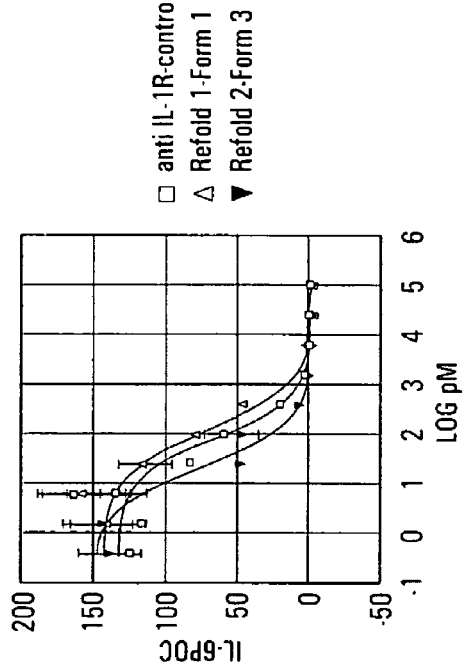
Figure 48:
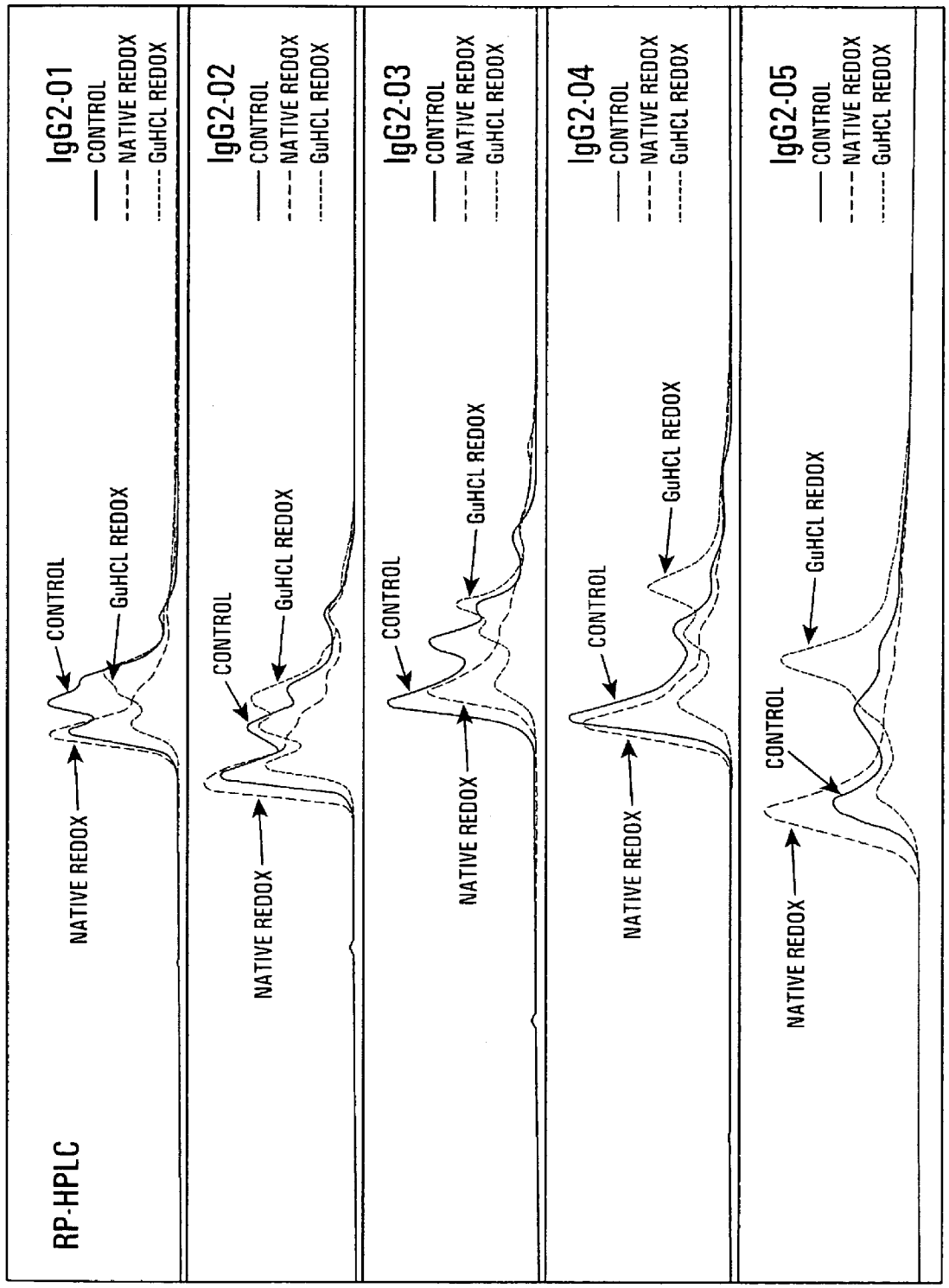
FIG. 48. Reversed phase chromatograms of other IgG2 antibodies that were treated with the same oxidative refold conditions as an IgG2 antibody. All of the IgG2 antibodies showed significant differenced by RP-HPLC that were consistent with the previous IgG2 antibody refold experiments.

The biological activity of the IgG2 refolded in the presence of 0.89M guanidine hydrochloride, is six time higher than the IgG2 refolded without guanidine hydrochloride and was three to four times higher than IgG2 bulk antibody that has been prepared without the use of redox agents to produce refolding of the protein. (FIG. 47).

The refolding methods can be performed on grains and kilograms of CHO-produced IgG2 bulk material to significantly increase concentration of the active IgG2 form per gram of the material and reduce the protein concentrations of formulation solution. The guanidine hydrochloride processing of the protein thus produced will further increase the yield of biologically active protein. The RP-HPLC/MS studies described herein show that all IgG2 antibodies contain multiple forms and can be modified according to the proposed refolding technique.

Using the refolded IgG2, it will be possible to delivery a larger effective dose of the IgG2, whilst using less amount of protein. Such a reduction in the overall amount of protein that is needed to produce a biologically effective response will be advantageous because reducing the amount of such a protein that must delivered to an animal will be likely to produce less of an adverse reaction when delivered e.g., by intravenous or subcutaneous injection. The methods of the present invention advantageously allow the production of homogeneous preparations of IgG2, which are in many cases a preferred modality of antibody pharmaceuticals as compared to IgG1 because there is more of a risk associated with elevated complement-binding activity of IgG1 as compared to IgG2.

While the exemplary protocols using the redox agents discussed above treat a purified preparation of recombinantly produced IgG2, it is contemplated that the IgG2 may be produced in the presence of such redox coupling systems, wherein the reagents are added to the media of the cell cultures in which the protein is produced. Alternatively, the redox agents can be added after purification of the proteins. Further, while the examples provided herein are directed to an examination of heterogeneity of IgG2, it is contemplated that the methods may readily be adapted and used for any recombinant protein that undergoes post-translational refolding and exhibits heterogeneity due to presence of disulfide bond that are amenable to scrambling. The methods described herein may be especially useful for the production of other IgGs such as for example, IgG3 and IgG4 antibodies which may exhibit heterogeneity.

Example 4

Further Studies on the Discovery and Characterization of Conformational Isoforms of Human Monoclonal IgG2 Antibodies Human therapeutic proteins produced in microbial cells often misfold and accumulate as insoluble inclusion bodies. The protein must be subsequently refolded using chaotropic agents under reduction/oxidation conditions in order to gain biological activity. Until recently, mammalian cell production of human therapeutic proteins had been thought to yield product having the correct fold and post-translational modifications. In the present Example there are identified four structural variants for an anti IL-1R IgG2 antibody and several other IgG2 antibodies. These newly characterized structural variants are unique to the IgG2 subclass (in both recombinant and naturally occurring IgG2's) which have not been seen in IgG1 s or IgG4s. Based on these findings, it is proposed that the IgG2 subclass of human immunoglobulins may be further divided into sub-subclasses to represent the conformational variants.

Materials and Methods

The following materials and methods are exemplary methods used in the instant Example. Similar such methods were-used in the other examples as specifically indicated in those examples. It should be understood that these exemplary methods may be readily modified for use in analysis of other IgG moieties in the context of the present invention.

An anti IL-1R IgG2 antibody and other human monoclonal IgG antibodies used in this study were recombinantly expressed and purified using standard manufacturing procedure. IgG2 kappa human myeloma from plasma was purchased from Sigma, #15404.

Refolding Procedure: In another specific example of a refolding procedure used in the present invention, human monoclonal anti IL-1R IgG2 antibody was incubated at either 3 mg/mL or 10 mg/mL in two buffers 1) 200 mM Tris buffer at pH 8.0 (native refold); 2) 200 mM Tris buffer at pH 8.0 with 0.9M GuHCl (GuHCl refold). A combination of cysteine: cystine were added at the molar ratio of 6 mM:1 mM (3 mg/mL) and 10 mM:1 mM (10 mg/mL), respectively. The precise concentration of cystine was not determined due to its poor solubility of the cystine, however, the cystine was provided by weight fall within the ratio noted above. The samples were placed at 2-8° C. for 48 hours. Other refolding conditions tried included the use of arginine and urea as a chaotropic agent, different ratios of cysteine: cystine and using cystamine in place of cystine, a range of GuHCl concentration for 0-2 M, and multiple temperatures during the redox process.

CEX analysis of intact antibody: The proteins were injected onto a Dionex WCX10 weak cation exchange column operated at 0.80 ml/min flow rate and 25° C. A gradient elution was used by increasing concentration of solvent B and, correspondently, decreasing A in the mobile phase. Solvent A was 20 mM sodium acetate at pH 5.0, solvent B included 20 mM sodium acetate, 0.5 M NaCl at pH 5.0.

Reversed-phase LC/MS analysis of intact antibody and antibody fragments: The proteins were injected onto a Zorbax 300SB C8 column operated at 75° C. The optimized method used a mobile phase consisting of a mixture of isopropyl alcohol and acetonitrile with 0.1% TFA. An Agilent 1100 Capillary HPLC system was connected on-line to a Waters Q-T of Micro mass spectrometer equipped with an electrospray ionization (ESI) source. The ESI-Q-TOF mass spectrometer was set to run in positive ion mode with a capillary voltage of 3400 V, sample cone voltage of 70-100 V, m/z range of 1000-5000, and mass resolution of 5000. The instrument was tuned and calibrated using multiply charged ions of bovine trypsinogen, MW23981.0, Sigma T1143. The deconvolution of ESI mass spectra was performed using a MaxEnt1 algorithm of in MassLynx software from Waters.

Limited proteolysis using pepsin: Pepsin digestion of human IgG2 was performed in a manner similar to that described in (Turner and Bennich, 1968, Biochem. J., v. 107, p. 171-178), but at lower pH and shorter time. The anti IL-1R IgG2 antibody and several other IgG2 antibodies were subjected to limited proteolysis using pepsin was performed for 1 hour at pH 2.5, in 100 mM ammonium acetate buffer, pH 2.5 at room temperature with a single addition of pepsin. The digestion was performed without denaturation with enzyme to protein ratio (w:w) of 1:50.

Reduction, oxidation, and tryptic digestion: Reduction and alkylation was performed using IgG under denaturing conditions to produce the free heavy and light chains for further analytical characterization. Antibody was diluted to 2 mg/mL with 7.5 M guanidine hydrochloride (Mallinckrodt, #7716), 0.1 M Tris-HCl (Fluka), 1 mM ethylenediaminetetraacetic acid (EDTA, Sigma #6281-92-6) pH 7.5 to a volume of 0.5 mL. A 5-μL aliquot of a 0.5M dithiothreitol (DTT, from Sigma D5545) stock solution was added to obtain 5 mM DTT concentration and the reaction mixture was placed at 37° C. for 30 minutes. Protein solution was then cooled to room temperature and a 13-μL aliquot of a 0.5M iodoacetamide (IAM, Sigma # 11149) stock solution was added to reach 13 mM IAM. The alkylation was performed at room temperature for 40 minutes while being protected from light. The 0.5 mL volume of the reduced and alkylated material was exchanged with a 1 mL of 10 mM sodium acetate (J T BAKER, Phillipsburg, N.J., #9526-03) pH 5.0 to a final concentration of 1 mg/mL of protein. Buffer exchange was performed using a NAP-5 gel filtration column packed with Sephadex G-26 medium (Pharmacia Biotech). The digestion with sequencing grade trypsin was performed using the reduced and alkylated IgG from the previous paragraph. Lyophilized trypsin (Worthington #3744) was suspended in water to a final concentration of 0.50 mg/mL. The reducing buffer was exchanged by a digestion buffer including 0.1 M TRIS, 1 M urea, 20 mM hydroxylamine (Sigma # H9876), pH 7.5. One M urea and 20 mM hydroxylamine were added to increase solubility of the light and heavy chains and to protect protein from carbamylation (Cohen, 1968, Ann. Review Biochem., v. 37, p. 695-726), correspondently. Tryptic digestion was performed overnight (15 hours) at 37° C. using an enzyme:protein ratio of 1:50. The digest was quenched with the addition of a small aliquot of 20% formic acid to a final concentration of 0.2% formic acid. The digest was either placed in the autosampler maintained at 4° C. for the RP LC/MS analysis or frozen for future analysis. Smaller amounts of antibody were reduced, alkylated and digested using similar procedure in smaller volumes with the same molar ratios of the components.

HPLC of tryptic peptides: Tryptic peptides were separated by reversed phase HPLC using an Agilent 1100 HPLC unit equipped with a U detector; autosampler, micro flow cell and temperature controlled column: compartment. A Polaris Ether column, 250×2 mm, packed with 3 μm particle size, 300 Å pore size C18 resin (Varian, Torrance, Calif., USA) was use for the peptide map separation. The solvents were: A=0.1% TFA trifluoroacetic acid in water, and B=90:9.015:0.085 of ACN: water: TFA. The procedure was as follows. Tryptic peptides were injected into the RP HPLC column, which was then equilibrated with 100% A. A linear gradient from 0 to 50% B was run over 205 minutes. The column was eluted with 200 μL/min flow and its temperature was maintained at 50° C. A total of 20 μg total protein digest was injected onto the column for the mass spectrometry analysis. The flow from the column was analyzed by the UV detector and then directed to an on-line ion trap mass spectrometer.

Ion-trap mass spectrometry: A Thermo Finnigan Ion Trap mass spectrometer LCQ DECA was used on-line with the HPLC system to identify the digestion products. Masses of peptides and their fragments were obtained using a triple play method including full scan, followed by zoom and MS/MS scans. A standard off axis-ESI source was used as atmosphere-vacuum interface. Instrument was tuned using the doubly charged ions of a synthetic peptide (m/z 842). Both, Sequest algorithm of Thermo Finnigan BioWorks 3.1 software and a Mass Analyzer software were used for peptide identification.

Binding assay: Biotin-coated fluorescent microspheres (Beadlyte beads (Upstate Biotechnology Inc.)) were coated with an avidin-IL-1R fusion protein. The beads were washed to remove unbound protein and aliquoted to 96-well filter-bottom plates (Millipore Corp). Titered amounts of the test antibodies (diluted from 1 nM to 61 μM) were then added to the beads. Antibody binding to the bead-captured avidin-IL-1RI fusion protein was detected using pPhycoerythrin-conjugated goat anti-human (Fab')2 (Southern Biotechnology). The binding reactions were analyzed using a Luminex 100 instrument (Luminex Corp.). The amount of antibody binding to the bead-bound protein was proportional to the mean fluorescence intensity (MFI) measured by the instrument. The binding curves and associated EC50 values (the concentration of antibody which generated a half-maximal response) were derived using PRISM™ software.

Biological activity (Chondrocyte assay): The anti IL-1R IgG2 antibody, Refold1-form1 and Refold2-form3 were serially diluted from 40 nM to 0.0256 pM in assay media. 50 μl of the diluted test antibodies were added to the wells 96-well plates seeded with human chondrocytes at a density of 10 000 cells/well in a 100 ul volume. The final antibody concentration ranged from 10 nM to 0.0064 pM. After a 30 min incubation, 50 μl of recombinant human. IL-1 beta was added to a final concentration of 10 pM. After incubation overnight, the antibody activities were analyzed using IL-6 and MMP-13 ELISAs. The inhibition of IL-6 or MMP-13 production was calculated as a percentage of maximum IL-1 beta activity. The inhibition response curve for each test antibody was established and the corresponding IC50 values (the concentration of antibody which reduces the signal by 50%) were derived using GraphPad PRISMa software.

Biological activity (Antibody-mediated lysis): For the antibody-mediated cell lysis assay, antibody was added to whole blood (1 mg/mL), incubated for 48 hours (37° C., 5% CO2), process for fluorescence activated cell sorting (FACS) analysis (label T/B cells and lyse red blood cells), and then analyzed. The depletion of B/T cells was monitored by flow cytometry.

Results

Figure 2B:
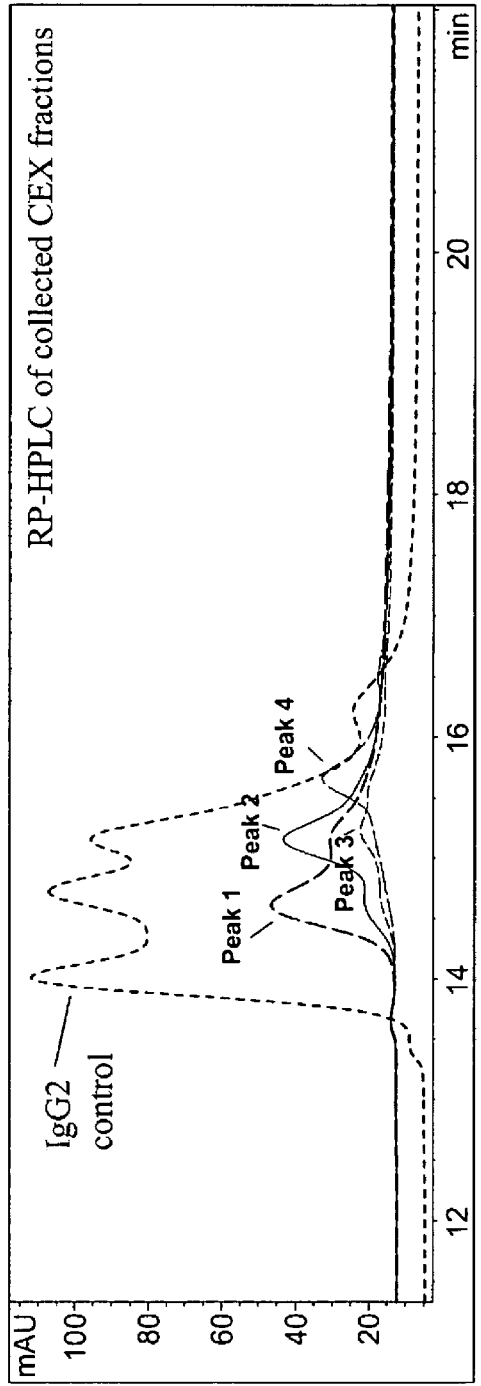

Both cation exchange (CEX) and reversed-phase (RP) chromatography of the IgG2 antibody against IL-1R revealed the structural heterogeneity of IgG2 (FIGS. 1 and 2A) even though the two techniques assessed antibody structure under very different conditions. The antibody was in the native conformational state (featuring the anti-parallel beta sheets) in the CEX mobile phase, which is close to physiological in pH, temperature and salt concentration. On the other hand, the antibody was in a molten globular state (Buchner et al., 1991 Biochemistry, v. 30, p. 6922-6929; Ptitsyn et al., 1990 FEBS Lett., v. 262, p. 20-24; Kuwajima, 1989 Proteins, v. 6, p. 87-103) when eluted from the reversed-phase column with high percentage of iso-propanol in aqueous 0.1% TFA (pH 2) at 75° C. Far-UV circular dichroism data indicate that the native globulin beta-sheets Were converted to helical and random-coil molten structures under these RP chromatography conditions. The fact that both the native and molten structures eluted from the CEX and RP columns have similar profiles suggested that the conformational isoforms have different covalent structures, which remain different in both the native and molten states. To correlate the peaks separated by the two different techniques, four CEX fractions were collected and injected on the RP column (named CEX fractions 1, 2, 3 and 4). The re-injected CEX fractions 1, 2, 3 and 4 co-eluted with the RP peaks 1, 2, 3, and 4 proving that there is a correlation between relative abundances and elution order of the peaks (FIG. 2B). This experiment also provided further evidence that RP chromatography itself is not a source of the peak splitting, but rather another useful analytical tool for detecting the covalent variants.

The human IgG2 anti IL-1R monoclonal antibody was cloned and expressed as an IgG1. The IgG1 subtype contained greater than 96% sequence homology with the IgG2. The human IgG1 anti IL-1R mAb was analyzed by CEX and RP HPLC using identical methods as previously described. The CEX and RP analysis of the IgG1 produced chromatograms which displayed a single homogenous peak. The IgG1 antibody elute approximately at the same time as form 3 (RP peak 3) of the IgG2 antibody (FIG. 1).

Figure 45:
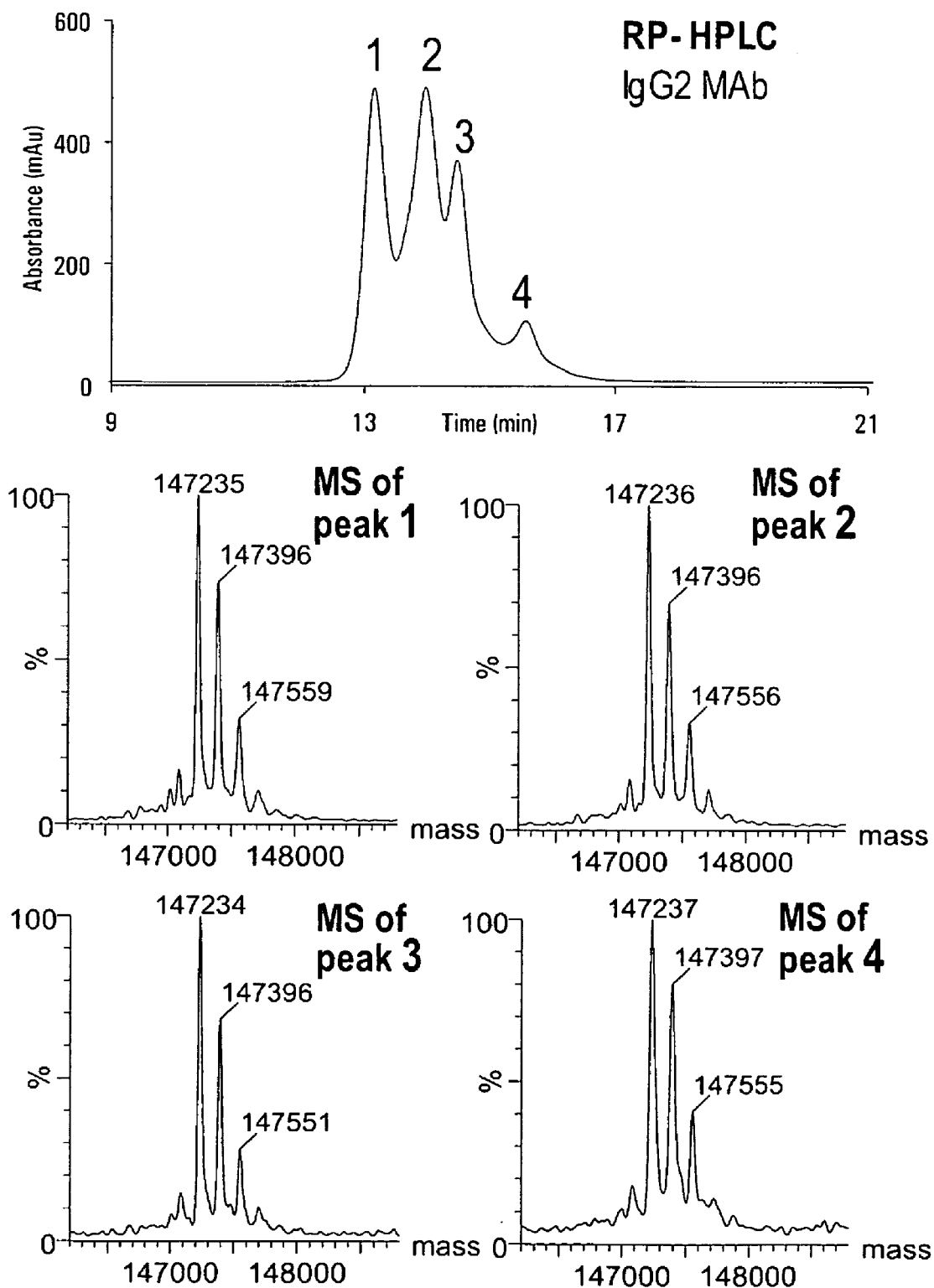
FIG. 45. A) Reversed phase chromatogram of anti IL-1R IgG2 antibody. B) Deconvoluted electrospray ionization mass spectra of the multiple isoforms eluting from the reversed-phase column as peaks 1, 2, 3, and 4. The MW values of the four peaks are: 147,256; 147,253; 147,254; 147,261 Da.

The ESI orthogonal-TOF mass spectrometer described in the Experimental section was connected on-line with the RP HPLC system to identify that the four isoforms of IgG2 have identical molecular weight values within the measurement error of the instrument of ±2 Da (FIG. 45). This eliminated glycosylation differences, lysine variants, and other chemical degradation modifications associated with a large mass change as the source of heterogeneity. Although deconvoluted ESI mass spectra of isoforms revealed identical molecular weight values, the isoforms carried different number of positive charges (protons) on their surfaces. RP chromatography of the intact antibody with UV detection at 215 nm and total ion current (TIC) detection was performed (FIG. 3A). ESI mass spectra containing multiply charged ions of the intact antibodies for the four separated isoforms were also obtained. These data showed that the later eluting forms carry a larger number of, positive charges (FIG. 3B). These is an indication that these variants have larger surface area and possibly better proton accessibility to the basic amino acid residues (Chowdhury and Chait, 1991 Anal. Chem., v. 63, p. 1660-1664; Dobo and Kaltashov, 2001, Anal. Chem., v. 73, p. 4763-4773; Fenn, 1993, J. Am. Soc. Mass Spectrom., v. 4, p. 524-535). When these forms elute from the RP column, form 3 possesses a larger surface area with a larger number of charges, while form 1 has smaller surface area and more "folded" structure. The fact that form 3 has a larger number of charges as compared to form 1 can be also derived from experiments which showed that form 3 also produced a higher total ion current (TIC), but lower UV absorbance as compared to Form 1. It means that a larger number of charges was carried on the form 3 species as compared to the form 1 species. The increase in solvent B concentration across the peak during elution of the peak is less than 0.5%. Therefore the change in organic solvent for electrospray is minor and should not shift the envelope of the m/z peaks. A control experiment using a (structurally homogeneous) IgG1 antibody was carried out to further verify that the difference in charge state is not induced by the minor difference in percentage of organic solvent in eluting mobile phase.

Figure 46A:
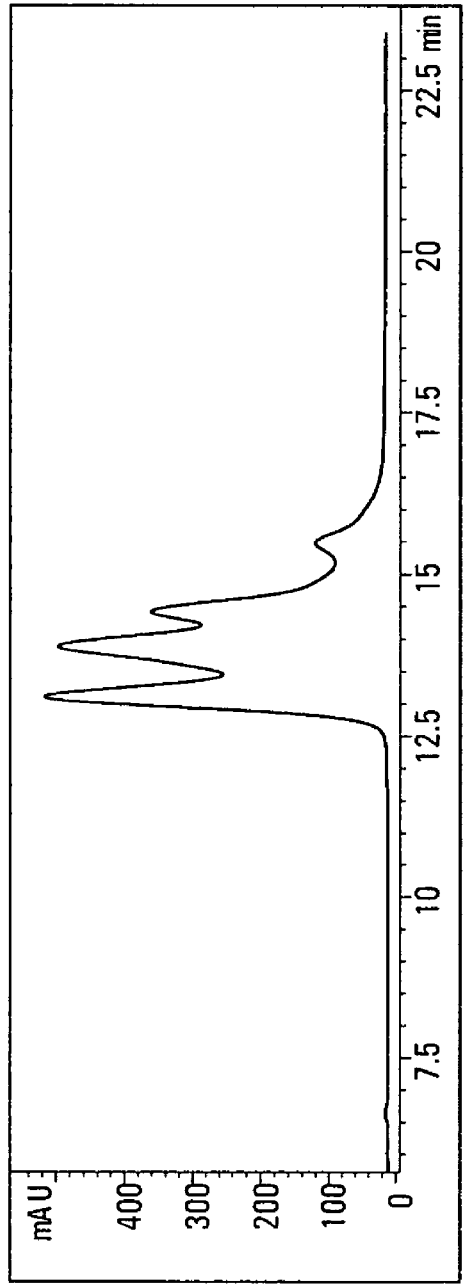
FIG. 46. Reversed phase chromatogram of an IgG2 antibody before A) and after B) reduction and alkylation. The light chain (LC) and heavy chain (HCl eluted as single peaks after the disulfide bonds were reduced.
Figure 46B:
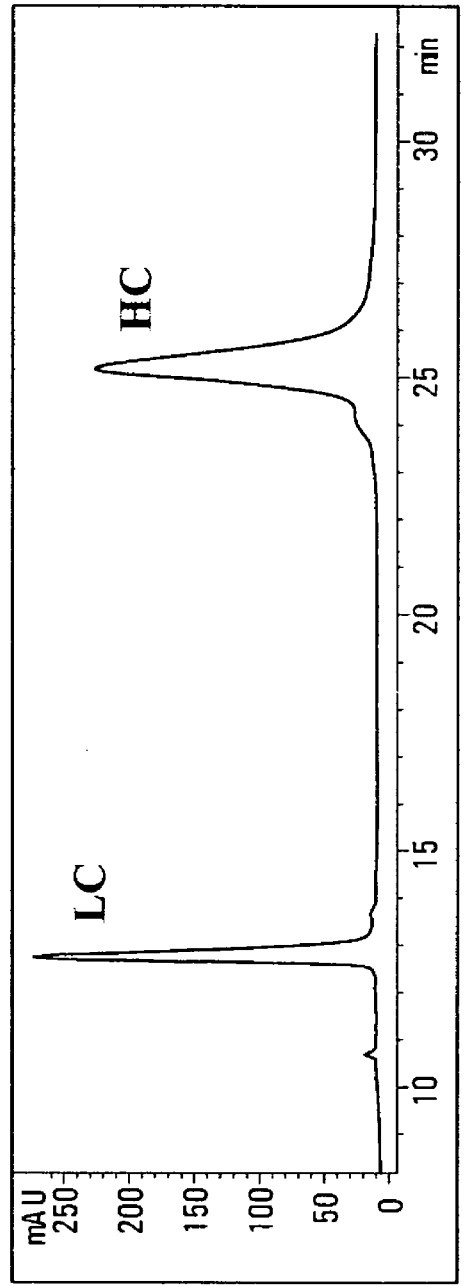

After reduction and alkylation, the heterogeneity disappeared and the RP chromatograms of the IgG2 antibody with reduced disulfide bonds featured only a single narrow peak for the light chain and a single narrow peak for the heavy chain (FIG. 46). These findings again show that the uncovered variants of IgG2 antibody have different disulfide connectivity or opened disulfide bonds. An opened disulfide was a possibility, because one open disulfide bond would increase mass by 2 Da, which was within the error margin of mass measurements for the intact antibody of MW 150 kDa. The structural variants related to disulfide bonds possess different covalent structures that could be separated by both CEX under the native condition and by RP chromatography under the denaturing conditions.

Figure 44:
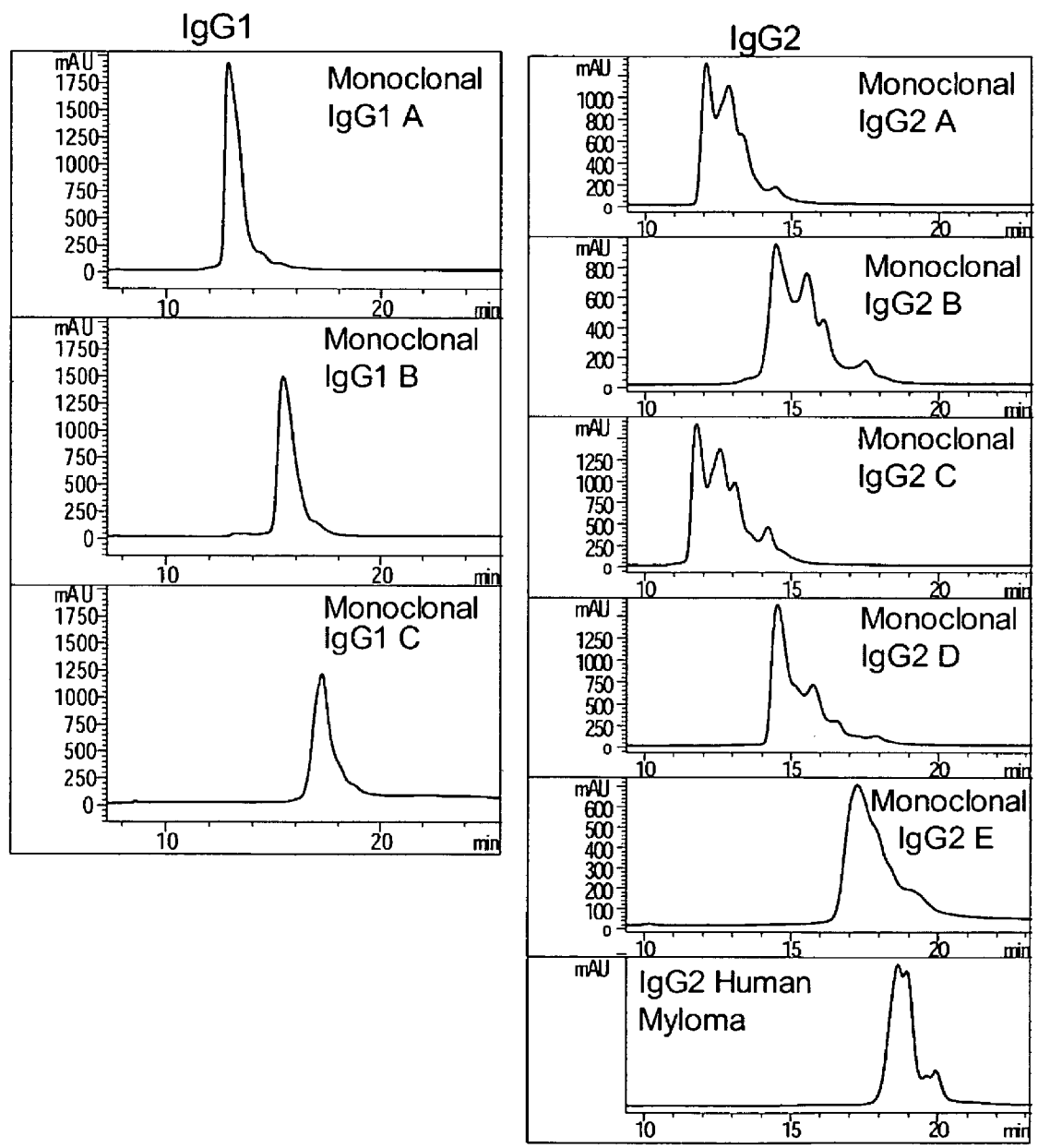
FIG. 44. RP-HPLC profiles of Intact IgG antibodies. The two subclasses of IgG's display significantly different profiles by this method. Human purified IgG2, purchased form Sigma, displayed the same heterogeneous profile as all Amgen IgG2's.

Reversed-phase chromatograms of several IgG2 and IgG1 antibodies used in this study were compared. While all IgG1 antibodies eluted as a single peaks, all IgG2 antibodies, including myeloma IgG2 antibody from human plasma serum, were separated on multiple variants under the same chromatographic conditions (FIG. 44). This result suggests that heterogeneity is a feature of entire IgG2 subclass of the immunoglobulin gamma molecules, including IgG2 molecules from human serum.

In IgG2 heavy chains, the CH1 peptide PLAPCSR was identified as a part of light-heavy interchain bond residues 127-133 (EU), and residue C131 from this peptide was connected to light chain. A similar peptide PLAPS131SL occupies a position from residue 127 to 133 (EU) in the human IgG1 heavy chain.

Figure 49:
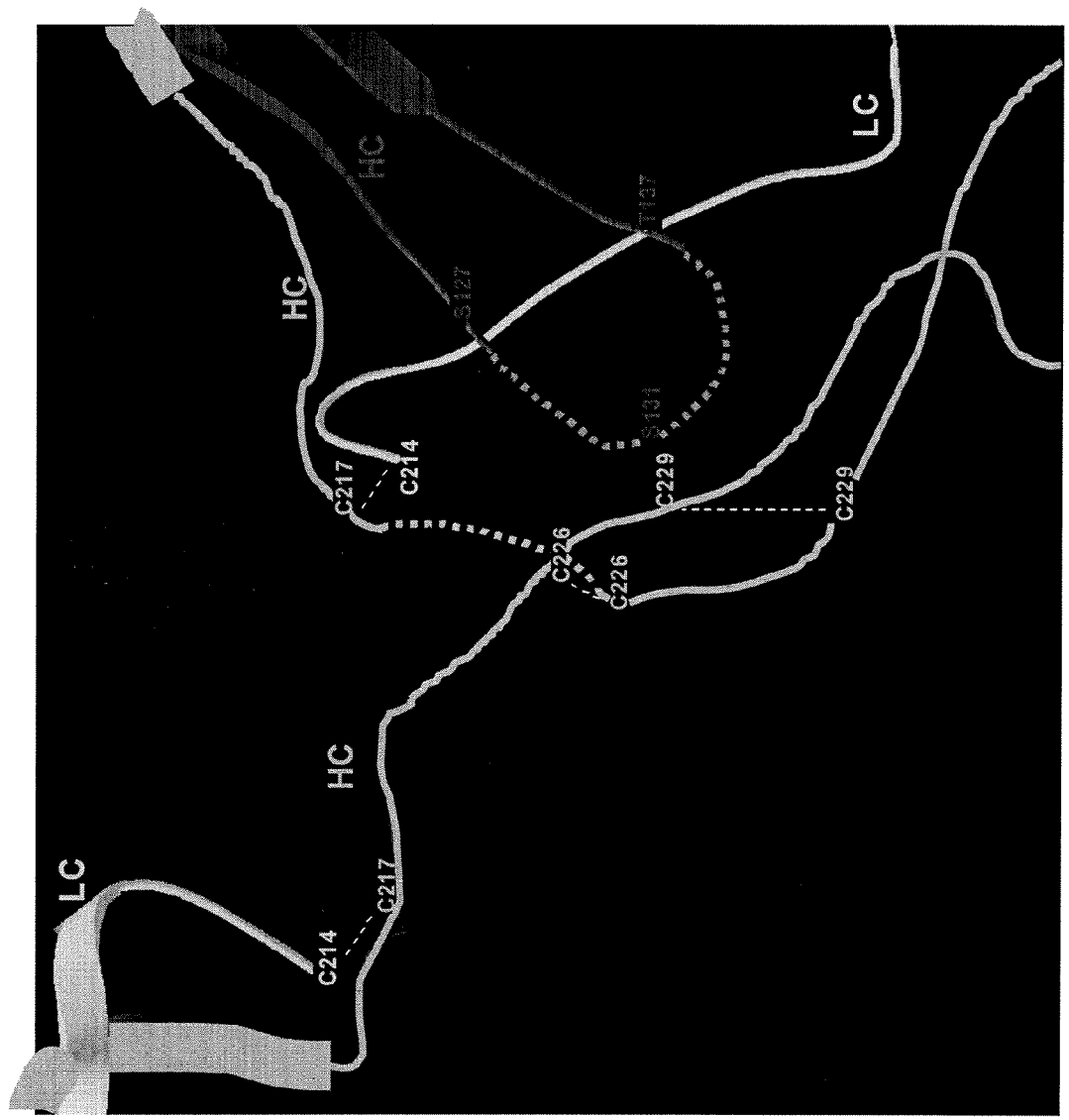
FIG. 49. Crystal structure of hinge region of human monoclonal IgG1 antibody plotted using PDB coordinates of entry 1HZH. Legend: light gray HC are heavy chains (HC) at the hinge; the dark gray line is heavy chain loop including residue S131; light gray LC are light chains (LC). Dotted lines were added to approximate positions of two flexible regions, coordinates of which were not determined by crystallography due to their flexibility: a loop of HC between S127 and T137 containing residue S131 (thick dark gray dotted line) and a section of the HC at the hinge between C217 and C226 (thick light gray dotted line).

Although the crystal structures of IgG2 antibodies have not been published, the close resemblance between primary sequences of IgG1 and IgG2 antibodies suggested that position of S131 in IgG1 heavy chain can be used to approximate position of C131 of IgG2 heavy chain with respect to cysteine residues 214 of light chain and 226 and 229 (hinge region) of the heavy chain. In a fragment of crystal structure of human IgG1 antibody near the hinge, downloaded from the RCSB Protein Data Bank under accession number 1HZN (Saphire et al., 2002, J. Mol. Biol., v. 319, p. 9-18), the position of serine S131 was used as approximate location of cysteine C131 in human IgG2 (FIG. 49). The crystal structure does show that three residues, LC C214, HC S131, HC C226, are in close proximity with respect to each other (within 6 Å). This proximity may allow them to crosslink generating several covalent structural variants with different disulfide bond structure in the hinge-area.

Figure 50:
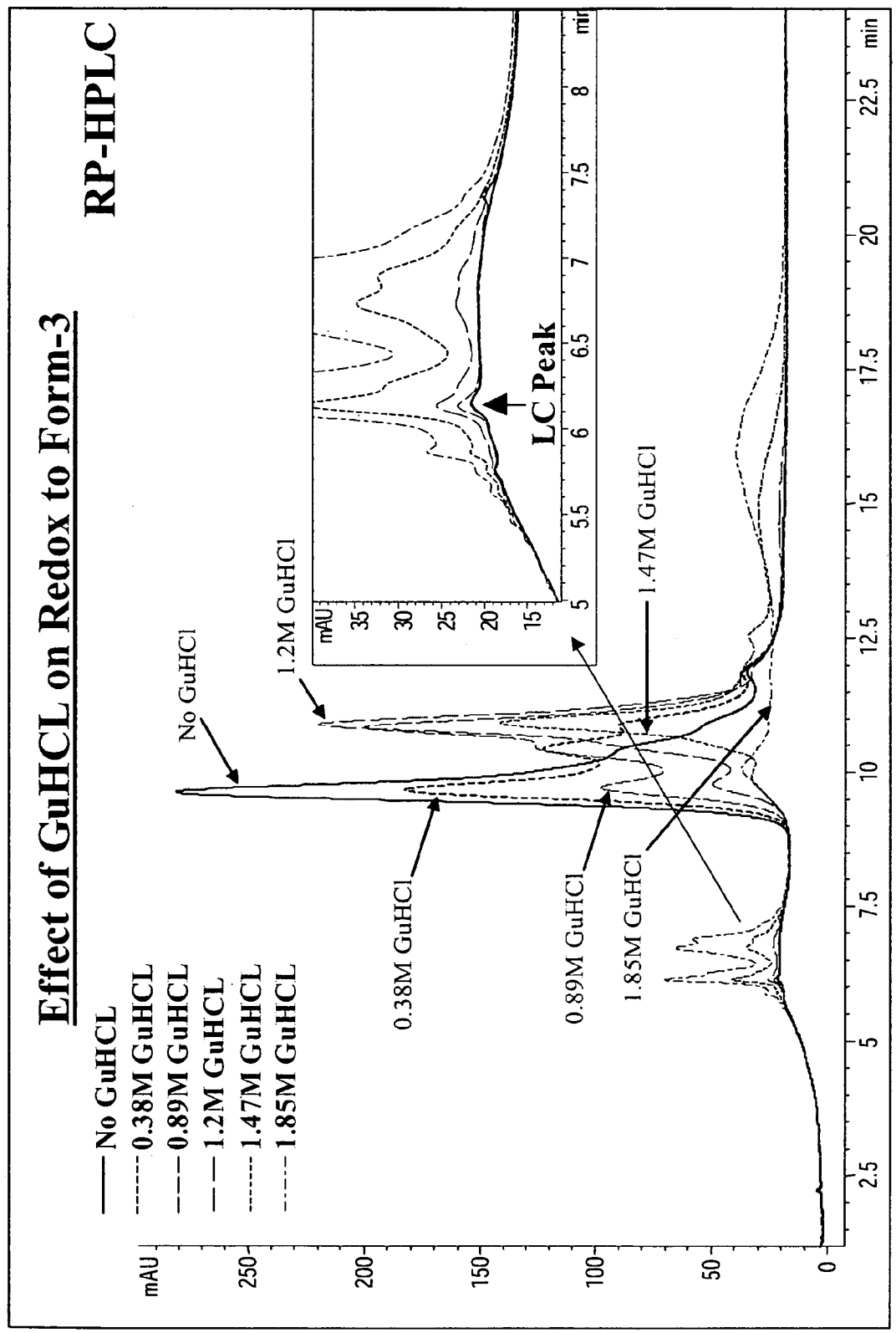
FIG. 50. Reversed phase chromatograms displaying the effect of redox treatment on an IgG2 (anti IL-1R) antibody in the presence of varying levels of GuHCl.
Figure 51:
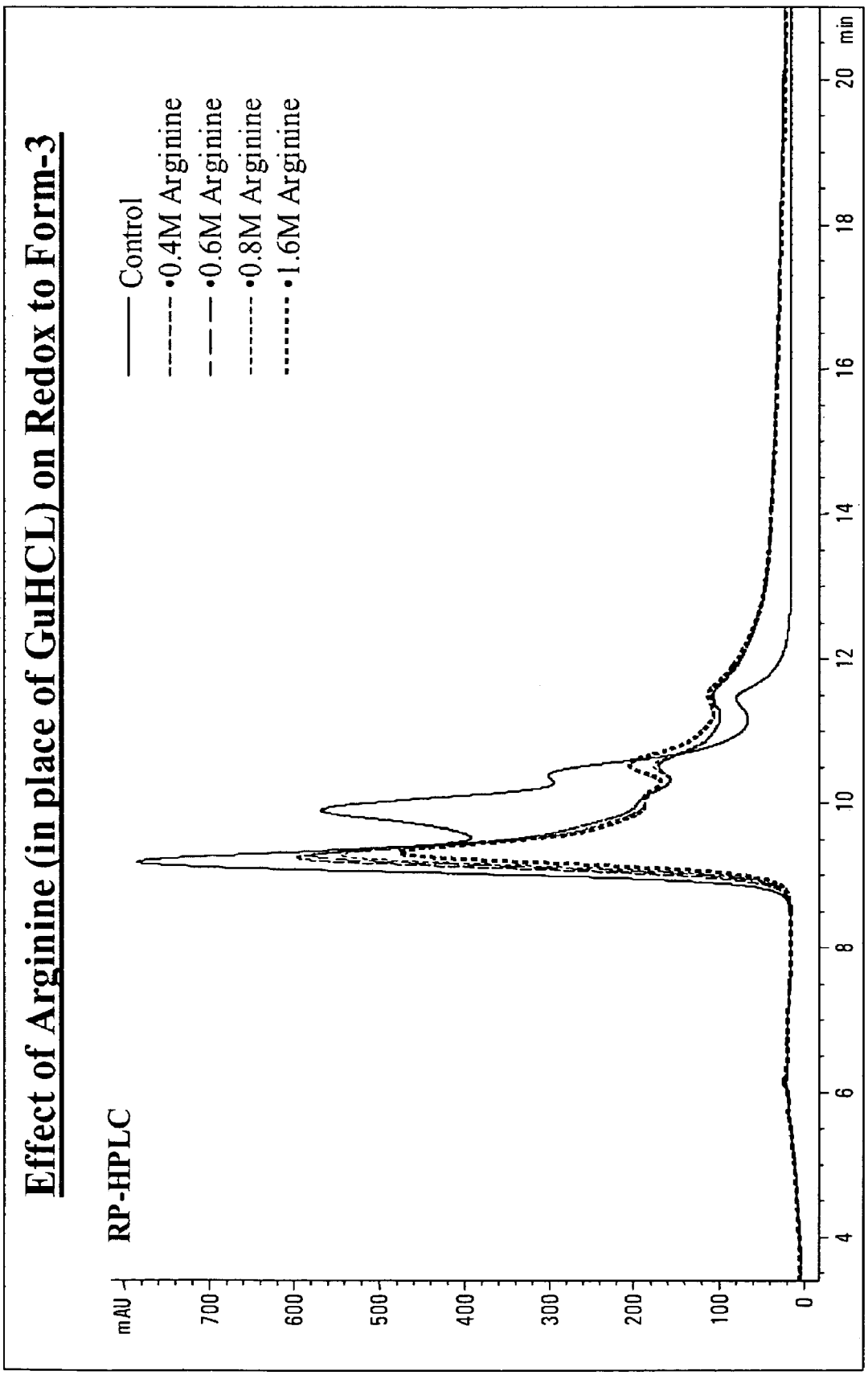
FIG. 51. Reversed phase chromatograms displaying the effect of redox treatment on an IgG2 (anti IL-1R) antibody in the presence of varying levels of arginine HCl.

The inventors have generated significant data to show that the different structural forms can be enriched by treating the IgG2 solution with redox agents (cysteine/cystine) in the presence and absence of a chaotropic agent (GuHCl). The working hypothesis was that the chaotropic agent in a relatively small amount may slightly perturb the structure and reposition the cysteine residues in the hinge in favor of one of the forms. To verify this hypothesis, several aliquots of the IgG2 antibody were treated with the mixture of cysteine and cystine according to the protocol described in the experimental section. The amount of added GuHCl was varied from 0 M to 1.4 M. The output of the refolding was monitored by the reversed-phase chromatography (FIG. 50), which showed that form 1 and form 3 were preferentially populated within 48 hours. Using reversed-phase chromatography comparisons of the original (untreated) humanized IgG2 antibody produced in mammalian (CHO) cells, the antibody refolded without any GuHCl and the antibody refolded with 1.0 M GuHCl, it was seen that form 1 was better populated in the absence of GuHCl. The addition of the chaotropic agent facilitated population of form 3. The enrichment of form 3 was fastest in the presence of 1.0 M GuHCl. Similar results were seen upon refolding the other IgG2 antibodies. The effect of using Arginine HCl as a denaturant was also assessed and is shown in Figure (FIG. 51). The arginine-HCl was identified as a weaker chaotropic agent as compared to GuHCl.

Although receptor binding and bridging assays showed no significant differences between the untreated and refolded materials, the cell based bioassays indicated that the isoforms displayed different biological activity. The bioassays were repeated over several days monitoring both IL-6 and MMP-13 levels with consistent results (FIG. 47). Form 3 was on average. 3.5 times more active as compared to the untreated material, while form 1 possessed only a fraction (0.7) of the bioactivity of the untreated material. Hence, form 3 was seven times more active than form 1. According to the reversed-phase chromatograms, although the refolding without GuHCl significantly enriched form 1, a small population of forms 2 and 3 remained in the sample.

The refolded material was also tested for differences in physical properties using DSC, CD, and fluorescence. The most dramatic difference between the forms was seen by DSC, where form-3 had only one major Tm at higher temperatures as compared to the control and form-1.

Example 4

Demonstration that an IgG1 Immunoreactive to IL-15 Contains Free Cysteine Residues in the Heavy Chain that is Partially Cysteinylated This example is directed to characterization of a human monoclonal IgG1 antibody that is immunoreactive with IL-15, specifically, 146B7. The 146B7 IgG1 antibody was characterized using reversed-phase LC/MS analysis for both intact antibody and after limited proteolysis with Lys-C protease. This IgG2 has a free cysteine residue in position 104 (C104) of the CDR3 heavy chain. Several modifications were identified with the most prominent being cysteinylation of the Fab fragment (+119 Da) probably at C104. Approximately 60% of the Fab fragments were cysteinylated. In addition, it was seen that the C-terminal lysine variance caused by partial cleavage of the terminal lysine residue. This type of variance is typical in hybridoma-produced IgG molecules. Approximately 70% of the IgG1 sample had no lysine on either of the heavy chains, 20% had a lysine on one of the heavy chains and 10% had lysine on both the heavy chains. Significant oxidation (approximately 10%) was also detected in the FAB region possibly at one of the methionine residues in the CDR region. No significant amounts of covalent dimers were detected even in samples that were stressed. The C104 residue was not readily labeled with IAA indicating that the free cysteine 104 was not readily accessible.

The IgG1 antibody investigated has a free cysteine in position 104 of the CDR3 heavy chain. This free cysteine can be a source of covalent dimerization and lead to stability issues during formulation or storage. The goal of the present example was to establish the redox status and evaluate accessibility of the free cysteine to an alkylating agent such as IAA, identify possible covalent dimers in heat stressed samples and characterize known posttranslational modifications such as lysine variance, glycoform variance (G0, G1, G2) and other possible modifications.

Reversed Phase LC-MS Analysis of Intact IgG1

Figure 9:
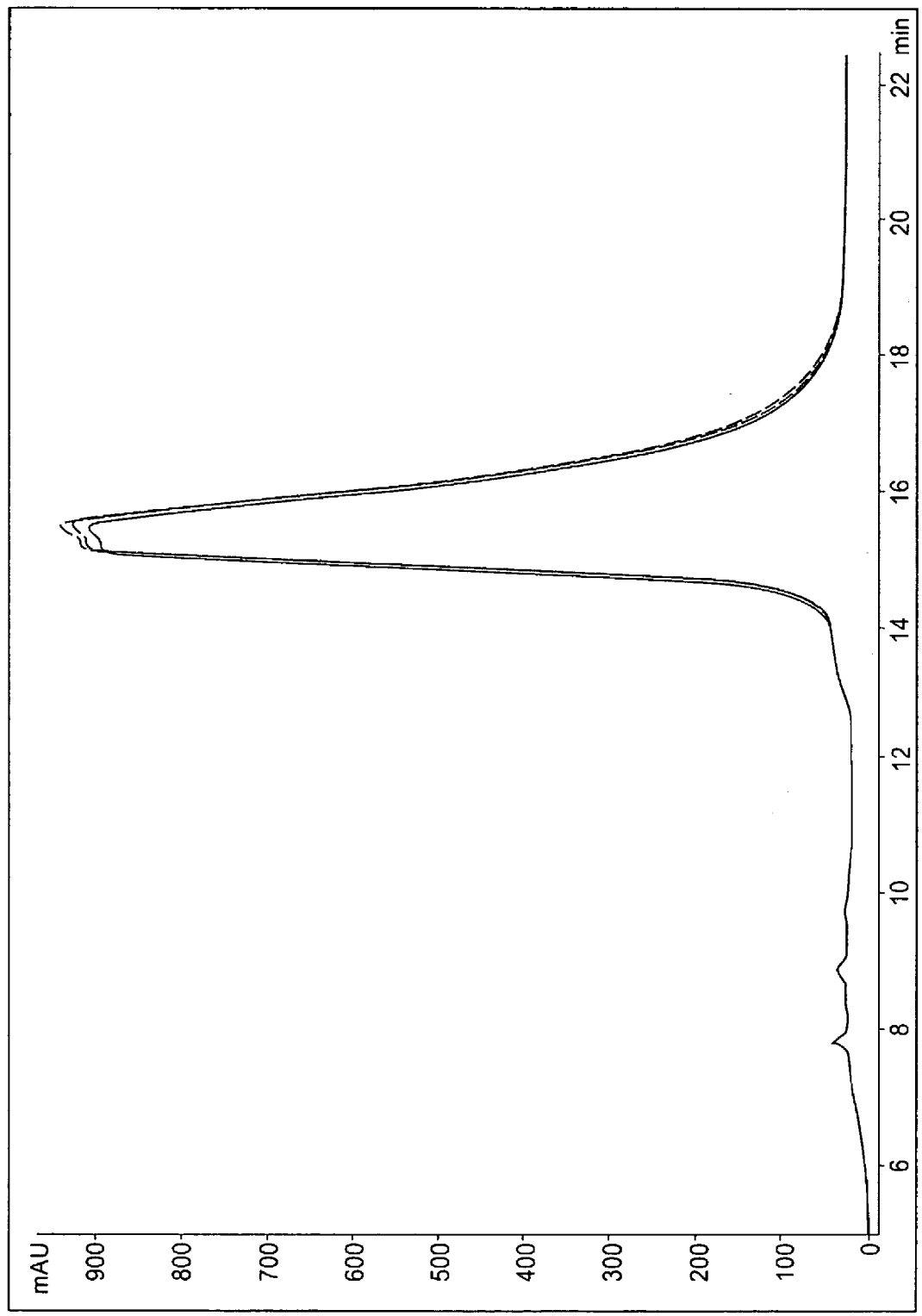
FIG. 9. RP chromatogram of the intact IgG1 of Example 9.

The RP chromatogram of the IgG1 is shown in FIG. 9 was similar to that of other IgG1 molecules. The major peak (peak 3) is comprised of the IgG molecule. There is a peak splitting on the top of peak 3, which may be due to the heterogeneity uncovered in this study. Two other minor peaks (peaks 1 and 2) can also be observed in the chromatogram. Using accurate mass measurements we have identified these peaks as the light chain fragment, E1-G93/S94, and a cysteinylated form of the light chain, respectively. Small amounts of free light chain have been observed in other IgG molecules.

The free light chain (peak 2 in FIG. 8) found in the IgG2 exists in cysteinylated form. The cysteinylation occurs on the free C214 residue of the light chain. This residue is involved in disulfide linkage between light and the heavy chain. Hence cysteinylation of C214 prevents the association between the light and heavy chains. However small amounts of non-cysteinylated light chain have also been observed in other molecules. The levels of light chain contaminants in this antibody sample can be readily monitored by the described RP LC/MS method. Cysteinylation is found in physiological proteins, which contain free cysteine. In recombinant antibodies it is introduced during the production stage possible due to the addition of cysteine, together with several other amino acids to feed the CHO cells. Varying degree of cysteinylation in the free light chain in different recombinant antibodies indicates that certain production parameters influence the degree of cysteinylation. This observation might be of note in understanding cysteinylation of C104 in the heavy chain of the IgG1.

Figure 10:
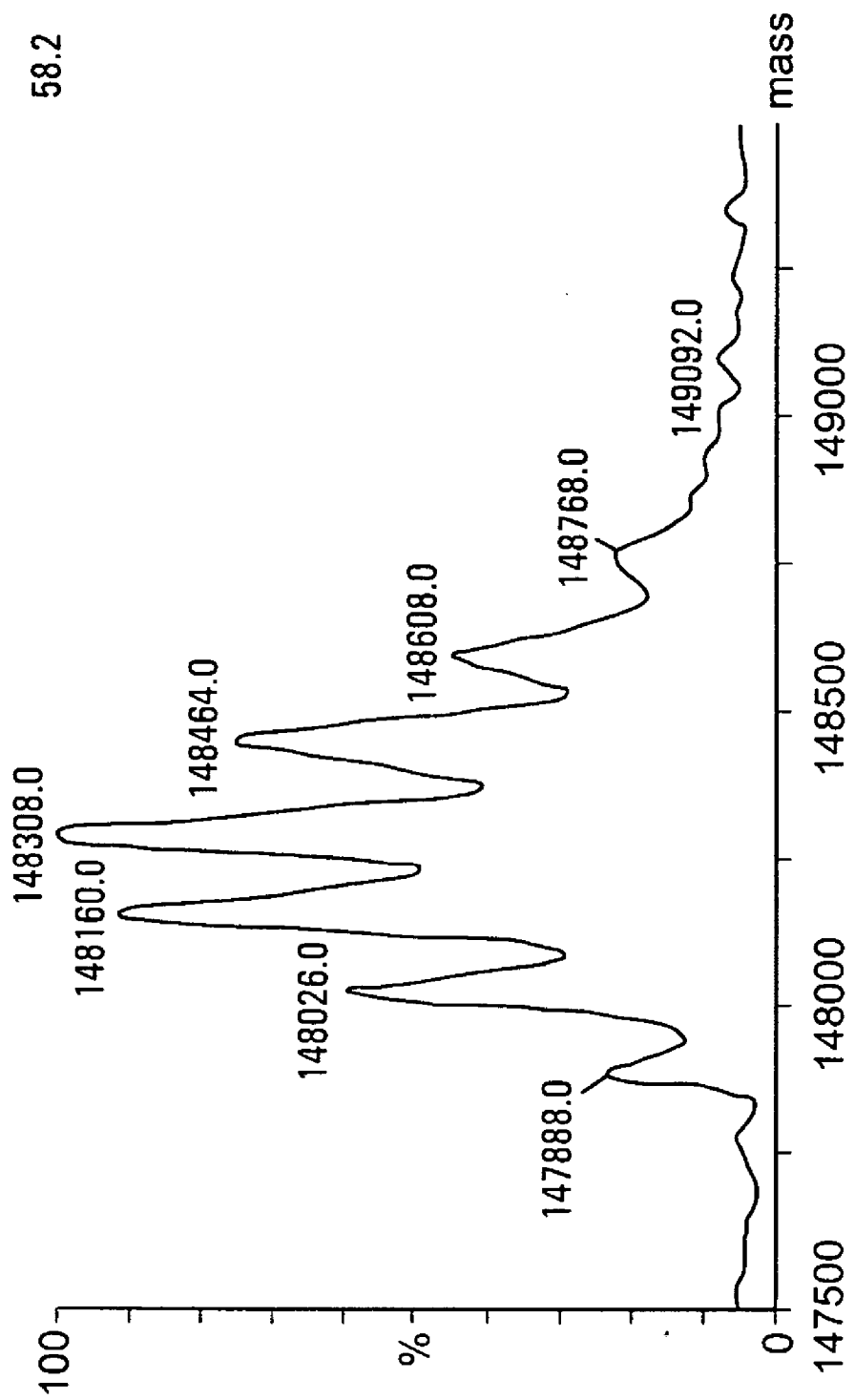
FIG. 10. Deconvoluted electrospray ionization mass spectrum of intact IgG1 of Example 4.

FIG. 10 shows the deconvoluted mass spectrum of the main peak. Typically in IgG1 molecules several galactose variants (G0 G1 and G2) are observed which are caused by the loss of 1 or both galactose residues from the biantennary sugar. These variants can be identified by a characteristic mass difference of 162 Da corresponding to the molecular weight of galactose. It can be seen from FIG. 10 that this typical pattern was not observed in the IgG1 of the present example. Instead, several peaks could be observed which differ by 140 to 150 Daltons. This data indicates that other sources of heterogeneity are present in IgG1 and the mass difference observed in the deconvoluted spectrum is a sum effect of these additional modifications along with the various glycosylation forms. The additional heterogeneity may be caused by modifications such as lysine variants, cysteinylation and oxidation.

Reversed Phase LC-MS Analysis of IgG1 after Limited Proteolysis with Lys-C

Figure 11:
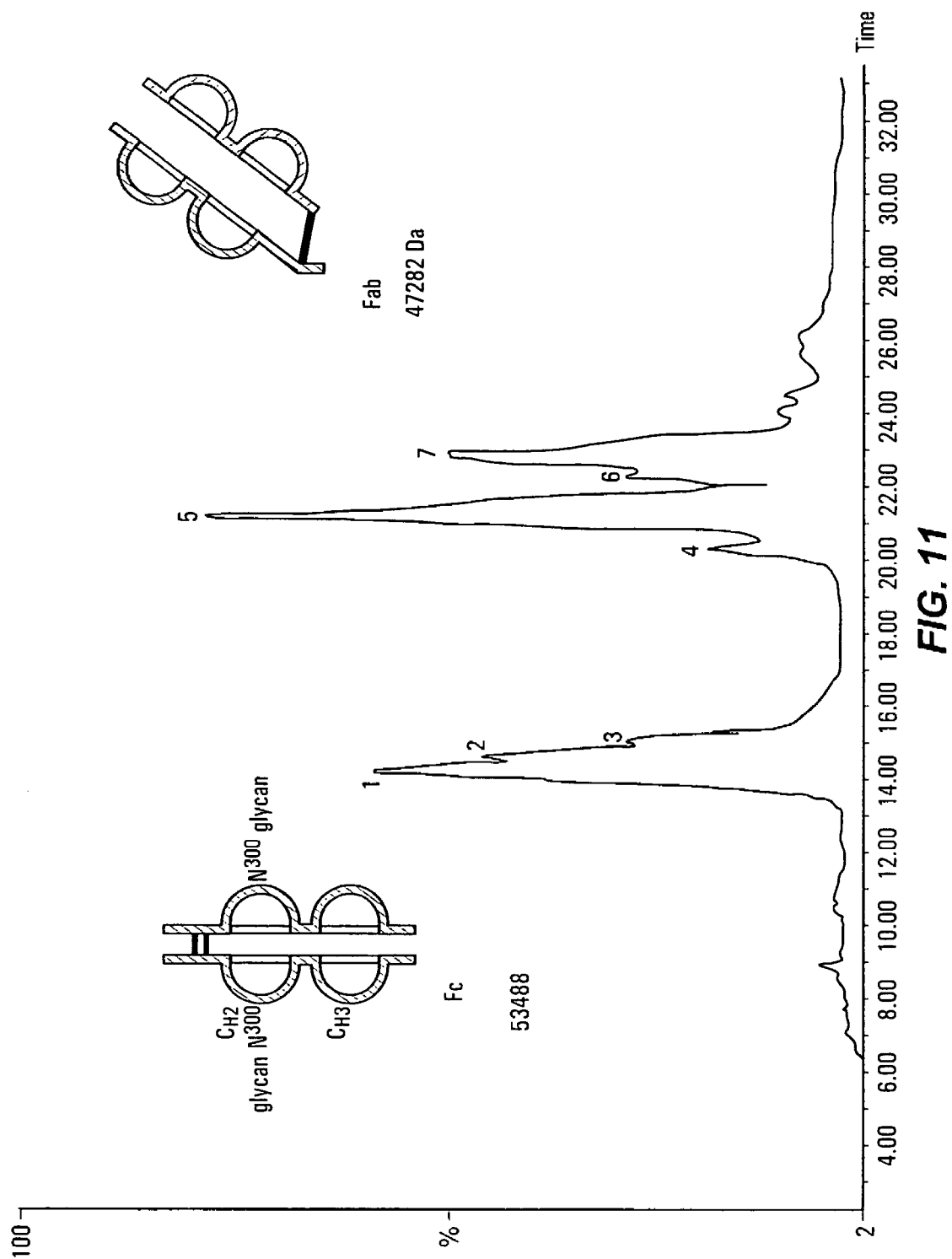
FIG. 11: RP chromatogram of the IgG1 of Example 1 after limited proteolysis with Lys-C.
Figure 12:
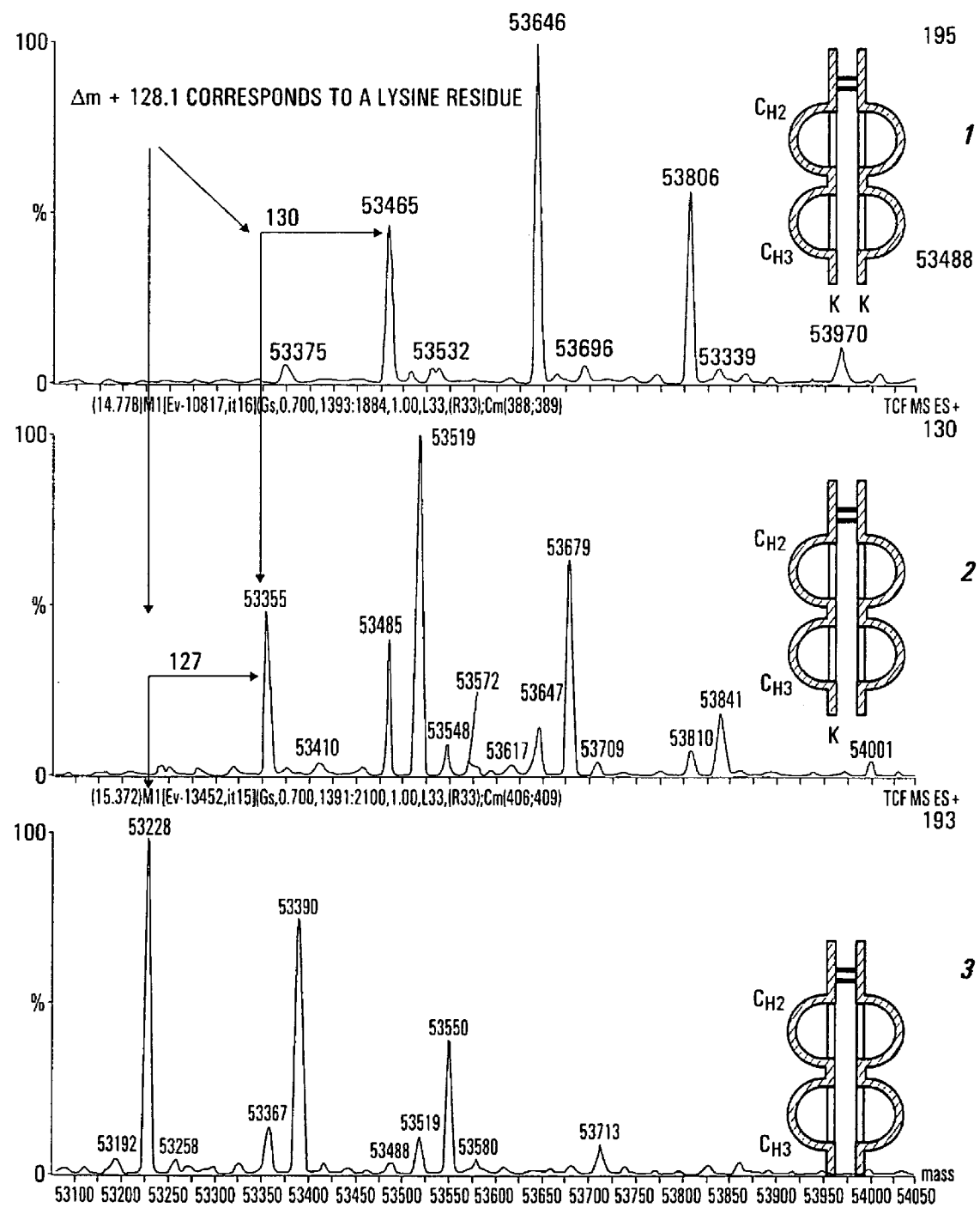
FIG. 12. Deconvoluted ESI mass spectra of peaks 1, 2 and 3 from FIG. 11.

To further characterize the sample, limited proteolysis with Lys-C protease was performed. Lys-C when used in low concentrations preferentially cleaves at the heavy chain lysine (residue 223) in the hinge region of IgG1 type molecules, generating Fab and Fc fragments. Limited proteolysis enhances. LC/MS analysis by isolating modifications from different regions and improves resolution because of the smaller size of the fragments as compared to the intact IgG. A reversed phase chromatogram of Lys-C-treated IgG1 of this Example is shown in FIG. 11. In a typical IgG1 sample, two major peaks corresponding to the Fab and Fc fragments are observed. However, several peaks were observed in the IgG1 of the present example, which are attributed to additional modifications seen in this sample. The deconvoluted electrospray ionization (ESI) mass spectra of peaks 1, 2, and 3 are shown in FIG. 12. The mass of these peaks corresponds with that of Fc fragment.

The mass difference between Fc molecules eluting in chromatographic peaks 1, 2 and 3 is approximately 128 Daltons, which corresponds well to the mass of lysine (128.2 Daltons). The lysine variance is commonly associated with IgG produced in hybridoma cell lines and associated with carboxypeptidase B activity. 146B7 is also produced in hybridoma cell lines and hence peaks 1, 2 and 3 are due to lysine variants. From the mass difference, it can be confirmed that peak 1 has lysine residues on C termini of both heavy chains. Peak 2 has a lysine on only one of the heavy chain and peak 3 has no-C-terminal lysines. Apart from lysine variance, peaks that differ by 162 Daltons are also seen. These peaks correspond to the sugar heterogeneity in which one or both galactose molecules at the end of the biantennary sugar moiety are lost. Such heterogeneity is very typical of the Fc fragment of both IgG1 and IgG2 molecules. No other atypical sugar modifications such as loss of the bi-antennary sugar moiety were observed.

Figure 13:
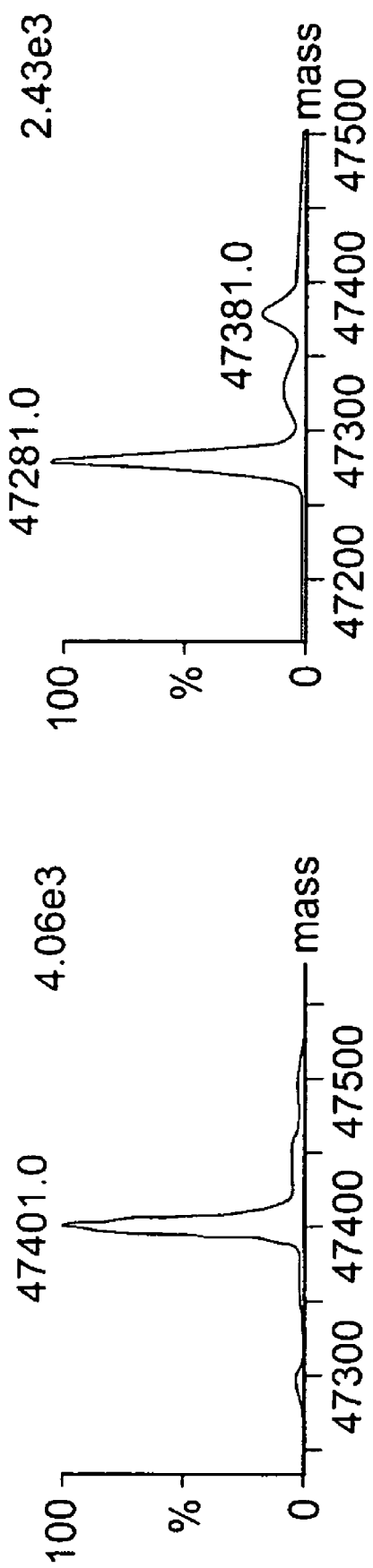
FIG. 13. Deconvoluted ESI mass spectra of peaks 5 and 7 from RP chromatogram in FIG. 11.

The deconvoluted mass spectra of peaks 5 and 7 from FIG. 11 are shown in FIG. 13. The molecular weight of 47281 Da for peak 7 matches with the theoretical molecular weight of Fab (47282). Peak 5 has a molecular weight of 47401, which is approximately 120 Dalton higher than that of peak 7. The mass difference of 120 Daltons corresponds to an additional cysteine residue. Cysteinylation was reported on free cysteines in physiological proteins. The IgG1 of this example has a free cysteine in the CDR 3 of the heavy chain. This free cysteine is cysteinylated probably during production. It can be seen from the peak area measurements that more than 60% of the molecule is present in the cysteinylated form. Peaks 4 and 6 have a mass difference of +16 Daltons from peaks 5 and 7, respectively. This mass difference corresponds to oxidation most likely of a methionine residue. The sites of oxidation may be further identified using peptide mapping experiments.

IAA Labeling Studies

Figure 14:
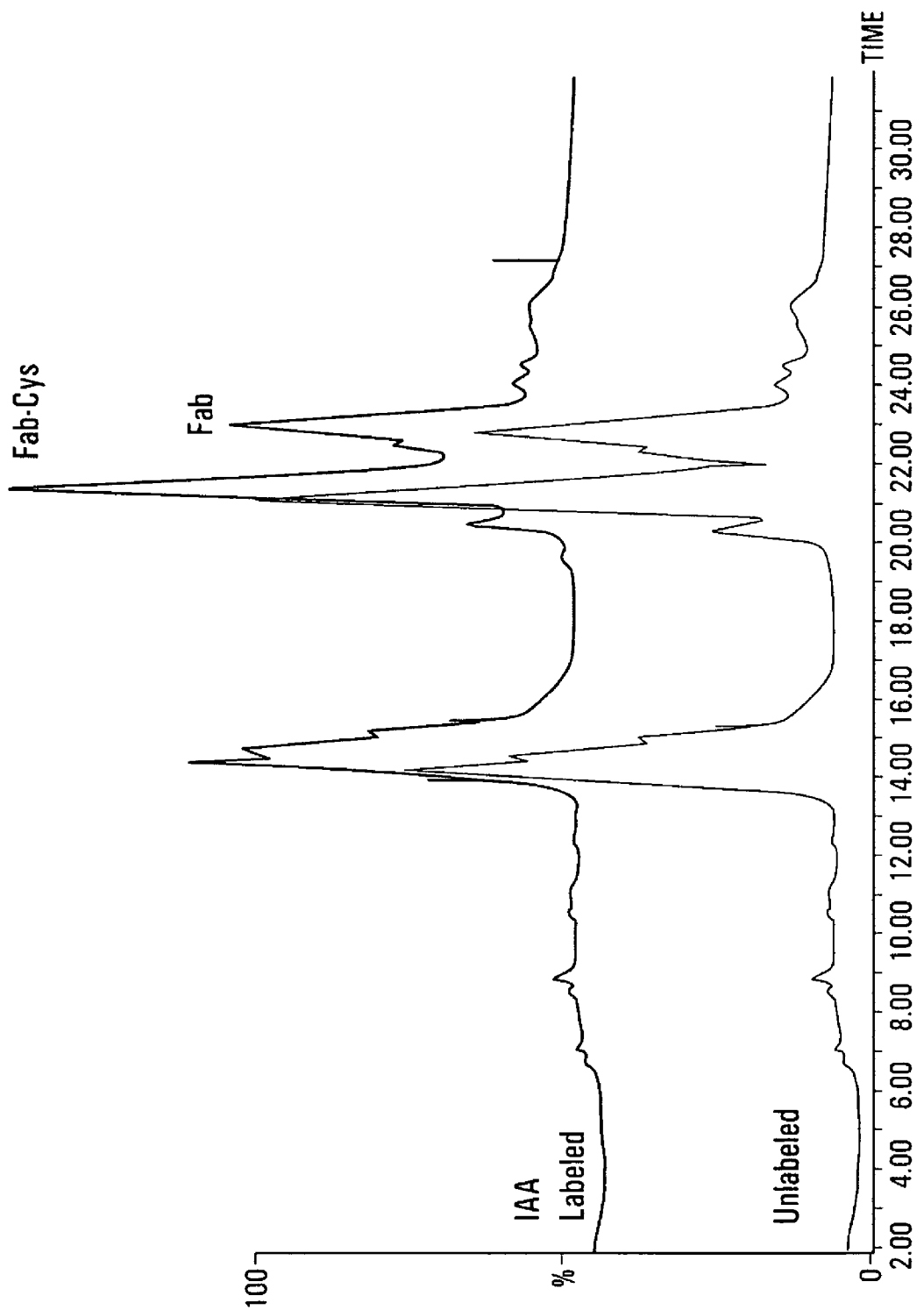
FIG. 14. RP chromatogram of the IgG1 samples of Example 4 after limited proteolysis.

IAA labeling was carried to probe the accessibility of residue C104 of the heavy chain. No differences could be detected in the reversed-phase chromatograms of either intact or Lys-C digested samples before and after IAA labeling. The reversed phase chromatograms of the IgG1, labeled and unlabelled, after limited proteolysis with Lys-C are shown in FIG. 14.

Figure 15:
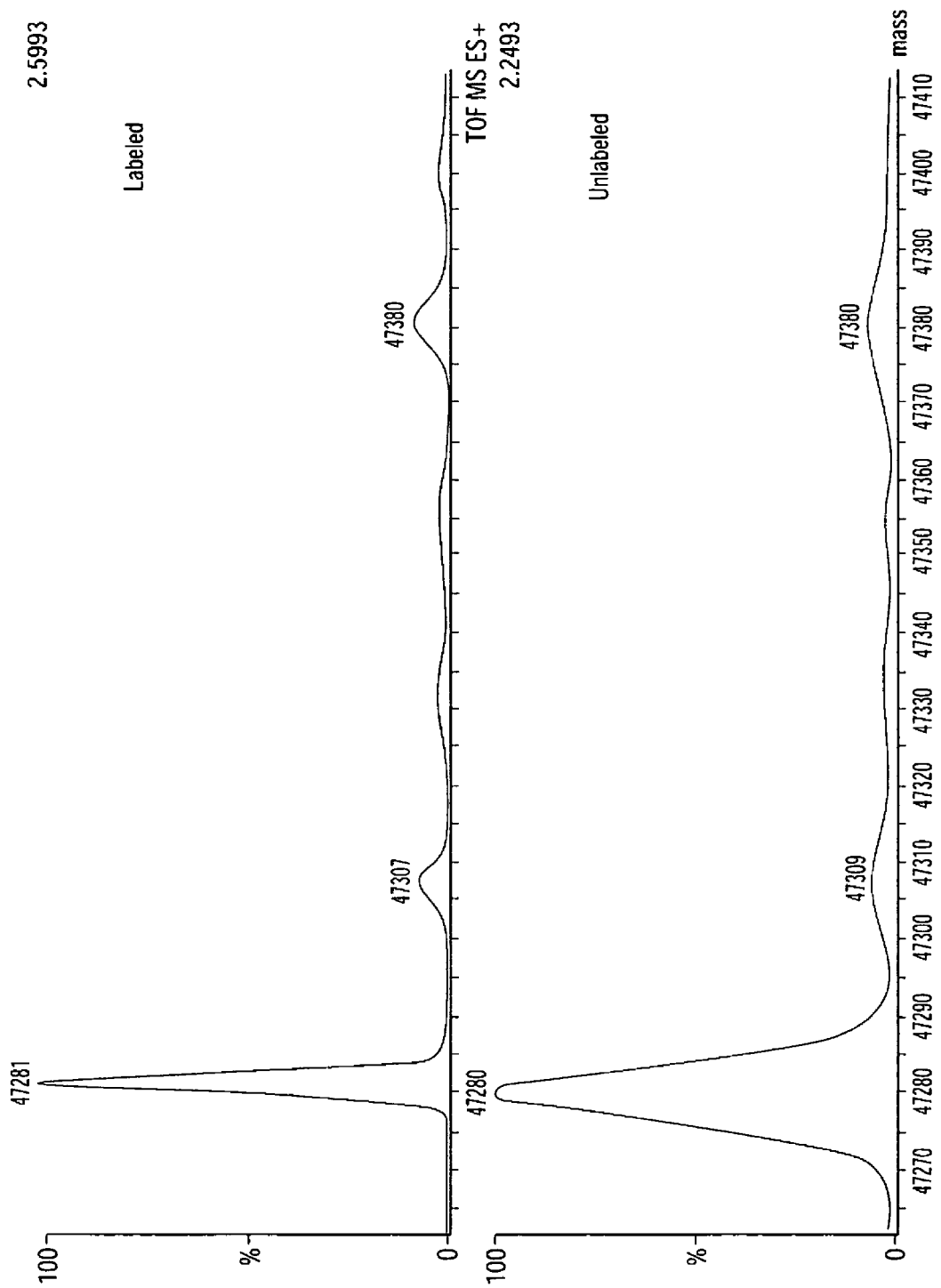
FIG. 15. Deconvoluted mass spectra of the Fab peaks from FIG. 14 for labeled and unlabeled IgG1 of Example 4.

The IAA labeling should result in the addition of 58 Daltons. The inventors have already shown in earlier results that 60% of IgG1 is cysteinylated and only the remaining 40% is prone to labeling. The deconvoluted mass spectrum of peak 5 (which represents the form that has free cysteine) from labeled and unlabelled sample is shown in FIG. 15. No shift in mass was observed after labeling, indicating that the free cysteine was not accessible for labeling.

RP LC/MS Analysis of Heat Stressed IgG1

Figure 16:
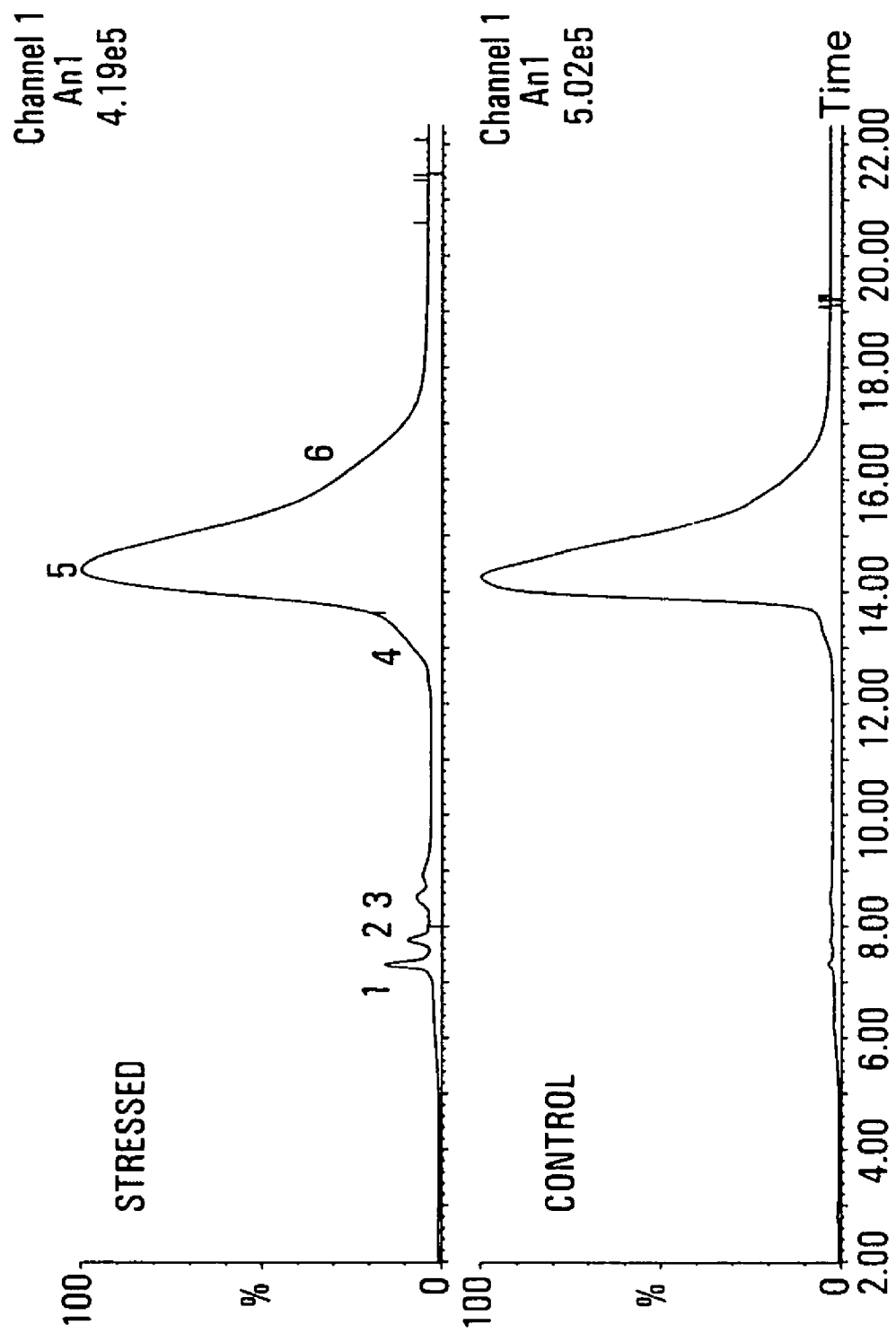
FIG. 16. RP chromatograms of stressed and control intact IgG1 of Example 4.
Figure 17:
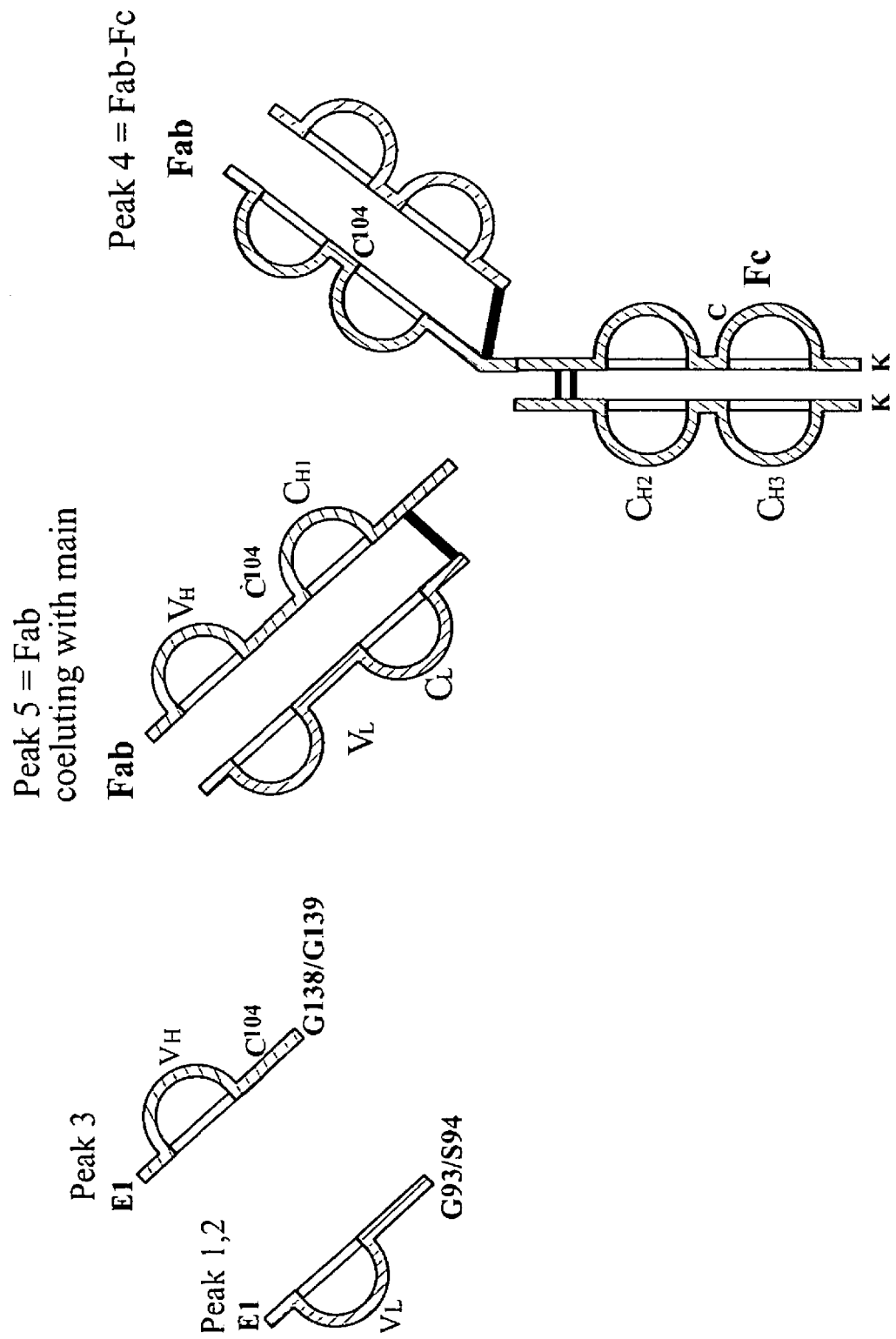
FIG. 17. Schematic of clips found in IgG1 sample incubated in A5S buffer for 1 month at 45° C.

Stressed samples of the IgG1 were incubated in A5S buffer for 1 month at 45° C. The free cysteine at residue 104 can be involved in covalent dimerization through the formation of intermolecular disulfide bonds. Such dimerization can be enhanced during heat-induced stress. Heat stressed samples were analyzed for the possible formation of covalent dimmers. FIG. 16 shows reversed phase chromatograms of 146B7 after stress versus control. FIG. 17 is a schematic of clipping identified in the stressed sample.

Peaks 1 and 2 of the stressed sample are due to the light chain clip E1-G93/S94 (10,125 Da) and the dehydrated light chain clip at 10,107 Da Peak 3 contains a heavy chain N-terminal fragment (E1-G138/G139). A slight fronting can be seen in the main peak of 146B7 IgG1 antibody stressed sample (peak 4). Peak 4 contains the "one armed antibody" Fab-Fc (FIG. 17) and a minor clip of the heavy chain (E1-C221/D222). The "lost arm, (Fab fragment" FIG. 17) co-elutes with the main peak (peak 5). The ESI mass spectrum of peak 5 shows a minor amount of the Fab clip with a typical sequence ladder due to multiple cleavage sites in the hinge region (data are not shown). Peak 6 in FIG. 16 contains a covalent dimer of the antibody. Because of the very low signal intensity we were unable to obtain a good deconvoluted spectrum. However, from the ESI mass spectrum, a small amount of dimer envelope can be seen in both the stressed and control samples. Because of incomplete separation and low intensity we were unable to get absolute quantification. The dimer is present at a very low amount, below 1%, and does not grow significantly after heat stress. The clips identified in 146B7 IgG1 antibody stressed sample are summarized in Table X and in the schematic of antibody clips shown in FIG. 17.

TABLE X

Summary of clips found in stressed samples

| Peak | Chain | Fragment | Mass (Da) |
|---|---|---|---|
| 1 | LC | E1-G93/S94 | 10,125 |
| 2 | LC | E1-G93/S94 (dehydrated) | 10,107 |
| 3 | HC | E1-G138/G139 | 15,122 |
| 4 | HCLC | Fab-Fc | 101,000 |
| 4 | HC | E1-C221/D222 | 23,960 |
| 5 | 2(HC:LC) | IgG | 148,016 |
| 5 | HCLC | E1-D222/K223 (HG) + LC | 47,148 |
| 6 | | IgG dimer | 296,000 |

Figure 18:
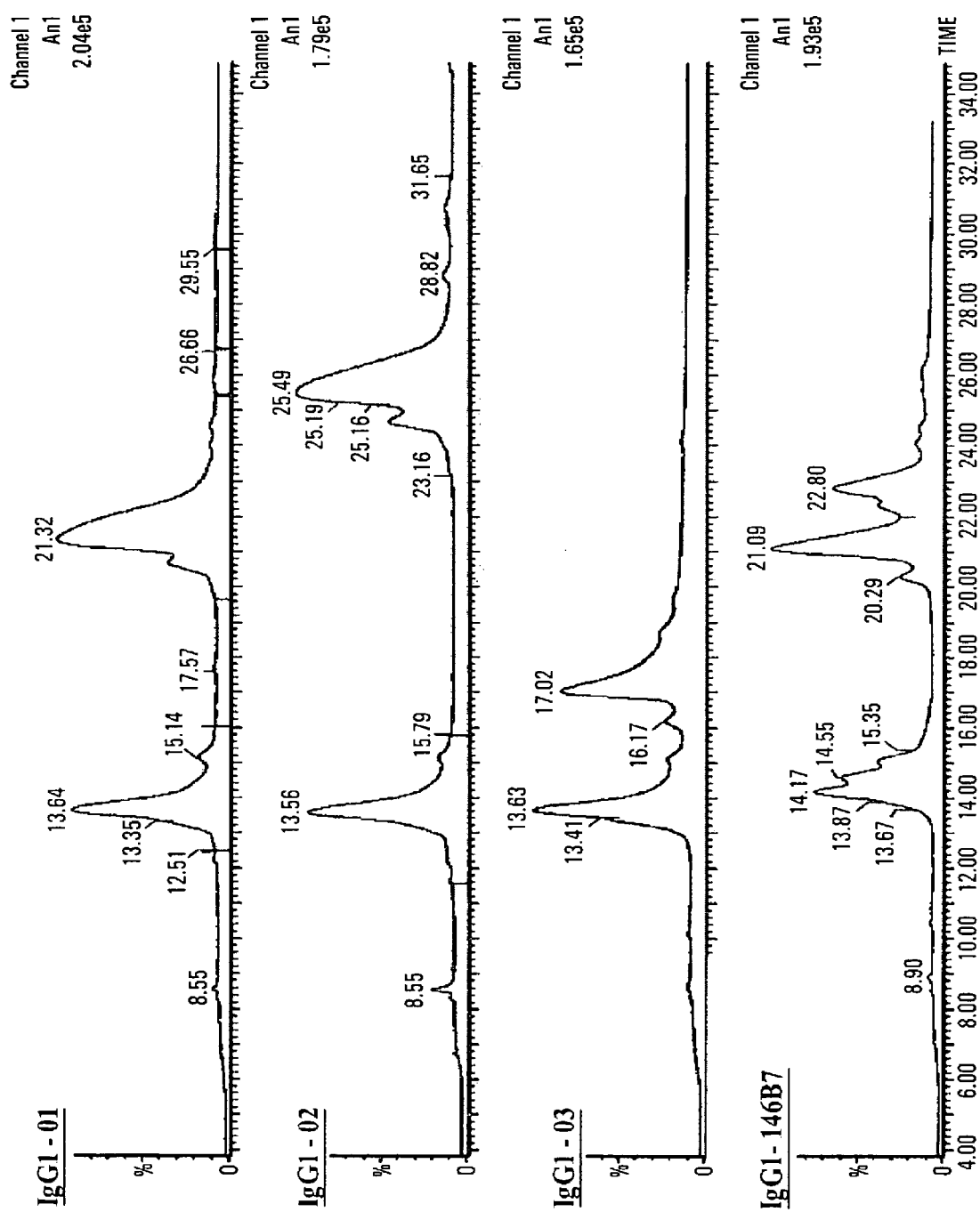
FIG. 18. Comparison of various IgG1 molecules by reversed phase chromatography after limited proteolysis with Lys-C protease.

The heterogeneity found in the Fc and Fab fragments of this IgG1 is unique to this molecule. To confirm that the heterogeneity found in this IgG1 is not method induced, similar studies were carried out on other IgG1 molecules. FIG. 18 shows RP chromatograms of four different IgGs after limited proteolysis. The Fc fragments are highly homologous among the IgGs and elute at approximately 14 minutes. The Fab regions contain the variable regions and elute at different times. It can be seen, from FIG. 19, that the heterogeneity found in the Fc and Fab region of the IgG1 of this Example is unique to this molecule. The data also confirms that the modifications are inherent to the molecule and not induced during the analytical process.

To summarize the results of this Example, it is shown that cysteinylation of C104 is a major concern in the IgG1 of this example. C104 is present in the CDR3 region and modifications on that residue could affect ligand binding. The amount of cysteinylation on C104 could vary in different batches. Significant batch-to-batch variations in the cysteinylation of light chain have been observed for several IgG molecules in formulation. The methods described herein will allow for methods of refolding these antibodies in order to eliminate cysteinylation of free cysteines. Such methods will lead to a reduction of structural heterogeneity, and/or increased biological activity and/or improved stability and shelf life. This will lead to a more uniform product. Cysteinylation of the antigen binding if particularly to be examined and controlled where observed.

Example 5

Redox Refolding of IgG1 CHO Improves Heterogeneity, Removes Cysteinylation and Increases Cell Based Biological Activity as Monitored by Reversed-Phase LC/MS and Other Techniques As discussed herein throughout, the prokaryotic recombinant production of eukaryotic proteins is hindered by the fact that during such recombinant production the proteins often misfold and accumulate as insoluble inclusion bodies. These proteins need to be refolded in the presence of chaotropic agents and reducing thiols in order to gain full biological activity. Until recently, it has been assumed that eukaryotic proteins produced in eukaryotic hosts (for example, human or humanized antibodies produced in CHO cells) are folded uniformly and correctly. As discussed in the examples above, several IgG2 antibodies were refolded to eliminate structural heterogeneity of these molecules and such refolding led to significant increase in activity of the IgG2. In this example, refolding of IgG1 antibody is further demonstrated. This IgG1 contains an un-paired cysteine in position 104. The process of refolding was monitored and refolded species were characterized by a recently developed reversed-phase LC/MS method for intact antibodies and their Fab and Fc fragments obtained after limited proteolysis with Lys-C protease.

Example 4 provides detailed characterization of the IgG1 antibody that is refolded in the present Example. This antibody has been characterized as having approximately 60% of the molecule modified by cysteinylation. The modification was determined, by limited proteolysis, to be in the Fab region of the antibody. It was also shown that there were at least two Fab isoforms present in the intact antibody. The differences were thought to be due to the additional cysteinylation and/or misfold(s) caused by the unique cysteine in position 104 of the heavy chain. In addition, bioactivity and bridging assays had been run using the same material, which displayed uncharacteristic results. The inventors suggest that cysteinylation in the Fab could be the cause of the unexpected properties. The present example provides further characterization data from experiments using oxidative refolding to further elucidate this effect and to assess whether such processing will lead to improvements of the pharmaceutical properties of IgG1.

Refolding Procedure

The IgG1 was incubated at 3 mg/mL in two buffers 1) 200 mM Tris buffer at pH 8.0 (native refold); 2) 200 mM Tris buffer at pH 8.0 with 0.9M GuHCl (GuHCl refold). A combination of cysteine: cystine was added at the approximate molar ratio of 6 mM:1 mM, respectively. The samples were placed at 2-8° C. for 48 hours. Aliquots were taken at 24 and 48 hours for analysis.

Analysis

Before and after refolding, the sample was analyzed by the following techniques: 1) cation exchange (CEX) chromatography; 2) reversed-phase LC/MS analysis of intact molecule; 3) limited proteolysis with Lys-C protease followed by reversed-phase LC/MS analysis of generated Fab and Fc fragments; 4) peptide mapping of the 146B7-IgG1 antibody bulk and refold material; 5) biological activity, 6) size exclusion chromatography (SEC); 7) fluorescence and circular dichroism spectroscopy. These techniques are generally discussed above in the some embodiments and specific parameters are provided below. CEX analysis of intact antibodies.

The CEX analysis was performed using a sodium phosphate and sodium chloride buffer at pH 7.2.

For the reversed-phase LC/MS analysis of intact antibodies, the samples were analyzed using a Zorbax 300SB C8 1×50 mm reversed-phase column packed with 3 μm particles and operated at 50 ml/min flow rate and 75° C. The optimized method used a mobile phase consisting of a mixture of isopropyl alcohol and acetonitrile. An Agilent 1100 Capillary HPLC system was connected on-line to a Micromass Q-TOF Micro mass spectrometer equipped with an electrospray ionization (ESI) source. The ESI-Q-TOF mass spectrometer was set to run in positive ion mode with a capillary voltage of 3400 V, sample cone voltage of 70-100 V, m/z range of 1000-6000, and mass resolution of 5000. The instrument was tuned and calibrated using multiply charged ions of bovine typsinogen, MW23981.0, Sigma T1143. The deconvolution of ESI mass spectra was performed using a MaxEnt1 algorithm, in MassLynx software.

The above-described conditions were also used for RP LC/MS analysis of Fab and Fc fragments.

The IgG1 was subjected to limited proteolysis using endoproteinase Lys-C (Roche, Cat # 1 420 429) for 30 minutes in pH 7.5, 100 mM TRIS buffer at 37° C. The digestion was performed without denaturation with enzyme to protein ratio (w:w) of 1:400. Using these conditions, we were able to create Fab and Fc fragments without further clipping.

Peptide mapping of the IgG1 was performed using Glu-C protease before after refolding. The digestion with Glu-C protease was performed at pH 5 ammonium acetate buffer without reduction and alkylation. At pH 5, the Glu-C protease cleaves largely at the C-terminus of every glutamic acid (E). The LC/MS/MS analysis was performed on an Agilent HP1100 connected on-line to a Thermo Finnigan LCQ ion trap mass spectrometer equipped with an ESI source.

For biological activity determinations, cell based biological activity assays were performed by monitoring IgG1 dose response with 200 pg/mL and 50 pg/mL IL-15 and by measuring biological potency.

Separation using SEC chromatography was performed on IgG1 CHO bulk, GuHCl refold, and hybridoma material. 10 ug of each of these compositions was injected (in separate runs) onto a Phenomenex TSK Gel super SW3000 column (4.6 mm×30 cm 4 u particle size). The running buffer was 100 mM Na Phosphate, 150 mM NaCl, pH 6.9 and the flow rate 0.25 ml/min.

For CD and Fluorescence spectroscopy, IgG1 CHO bulk, GuHCl refold, and hybridoma samples were diluted to final concentrations of 0.5 mg/mL in A5S buffer. CD spectra were collected at 25° C. from 250-200 nm on an AVIV model 202-01 circular dichroism spectrophotometer using a pathlength of 0.2 cm for all samples. Fluorescence spectra were collected at 25 degrees C. on an AVIV ATF105 spectrofluorometer exciting at 290 nm and monitoring emission from 500 to 300 nm.

The above techniques were performed and the following results and data are exemplary of the results that were obtained through such experiments.

CEX of intact 146B7 Oxidative Refolded Material

Figure 19:
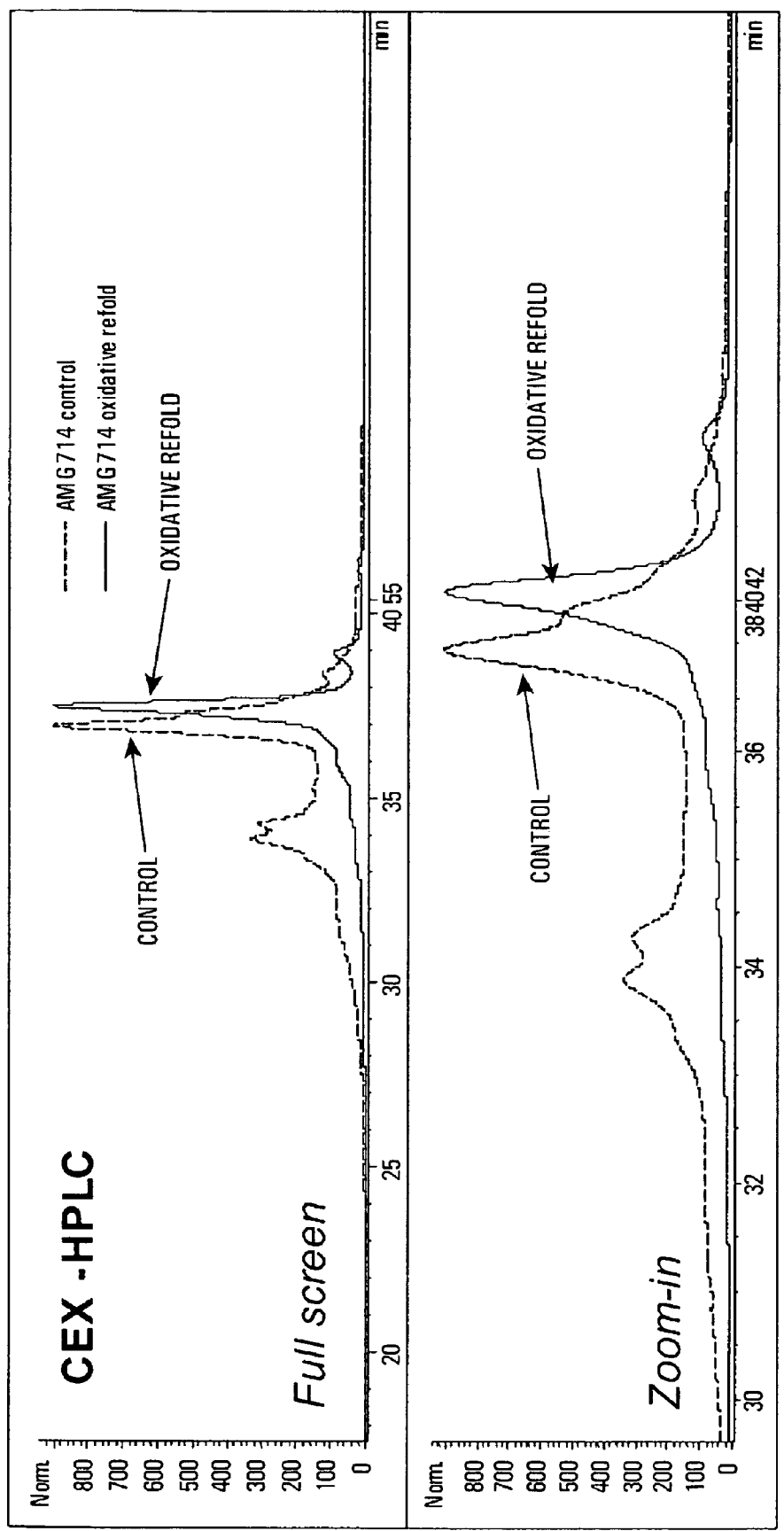
FIG. 19. CEX chromatogram of intact IgG1 control and native refold after 24 hour refolding.

FIG. 19 shows cation exchange chromatogram of IgG1 CHO bulk and GuHCl refold. The chromatograms indicate that the earlier eluting (acidic) peak disappears after refolding.

Figure 20:
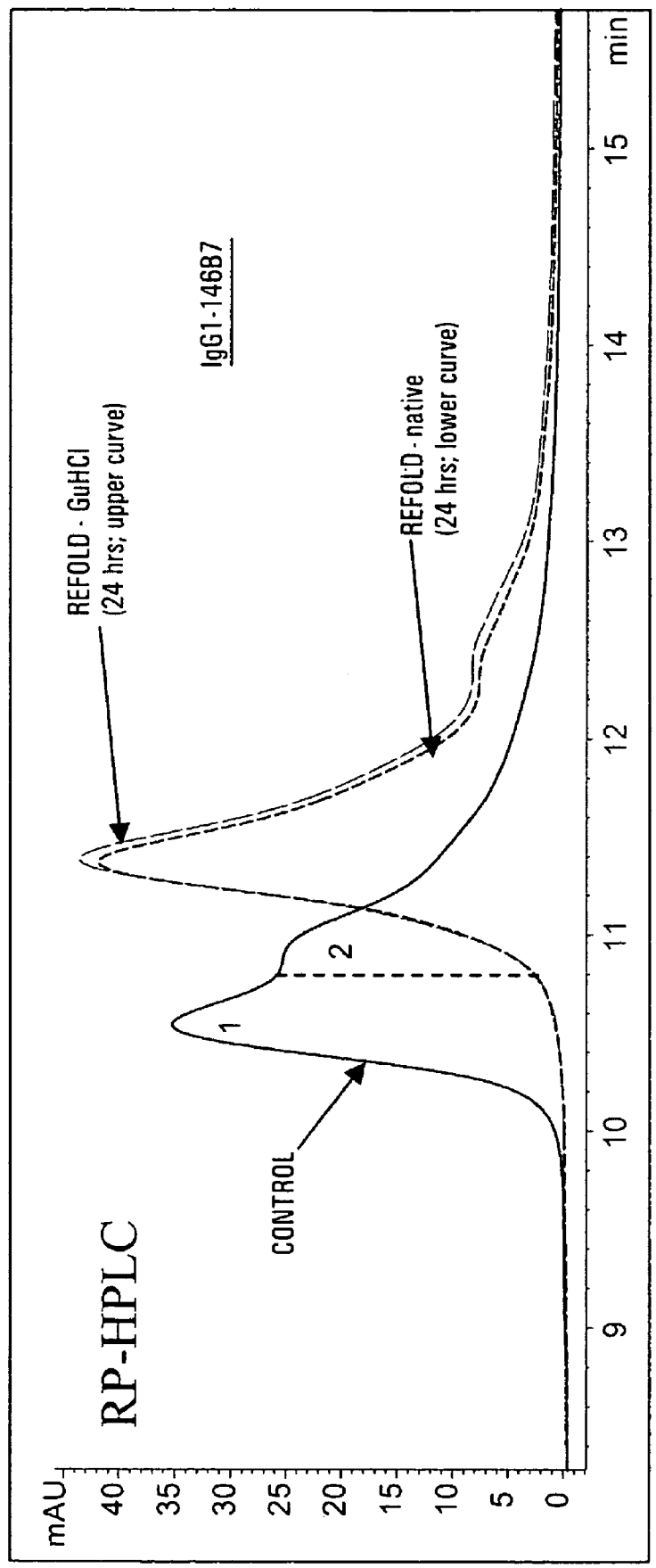
FIG. 20. RP chromatogram of intact IgG1 CHO control, native refold, and GuHCl refold samples after 24 hr incubation.
Figure 21A:
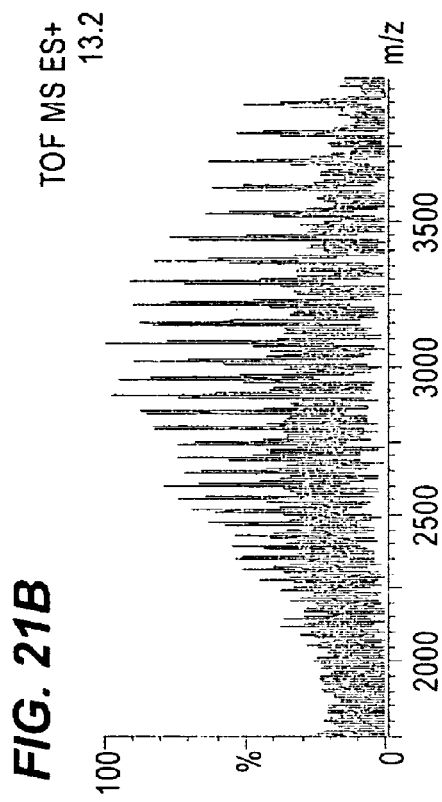
FIG. 21. ESI mass spectra of peak 1 (A) and peak 2 (B) separated on the RP chromatogram of IgG1 bulk. Deconvoluted ESI mass spectra of peak 1 (C) and peak 2 (D).
Figure 21B:
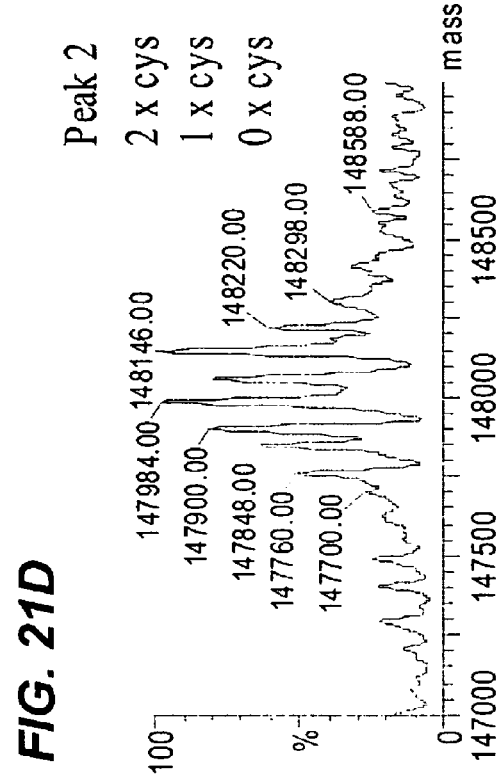
Figure 21C:
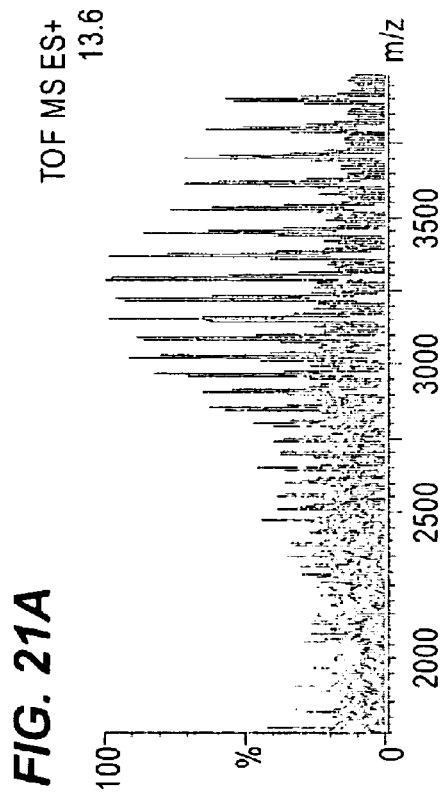
Figure 21D:
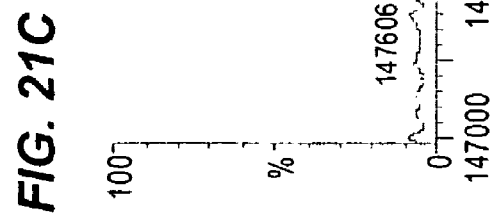

The reversed phase LC/MS analyses of intact IgG1 oxidative refolded material is shown in the chromatogram in FIG. 20, which shows IgG1 CHO before and after oxidative refolding. The control sample displayed two major peaks with a smaller post-peak shoulder. The refolded materials eluted mostly as a single species in FIG. 20, which aligned with the small post-peak seen in the control. The IgG1 CHO samples refolded both with and without GuHCl showed similar RP chromatographic profiles. Similarity of RP chromatographic profiles suggests that with 0M or 0.9M GuHCl, refolded species have the same structure and refolding rates are approximately the same. The accurate mass measurement of the species eluting as the RP chromatographic peak 1 from 10.0 to 10.5 minutes showed that these antibody molecules possessed MW values approximately 240 Da higher as compared to calculated molecular weight of the IgG2 that is discussed in U.S. Provisional Application 60/621,295 (see also FIG. 21). This and later described analyses identified this mass addition as due to the cysteinylation of two non-paired cysteine residues. Peak 2 eluting between 11 and 13 minutes is an overlap of doubly-, singly- and non-cysteinylated antibody molecules.

Figure 22A:
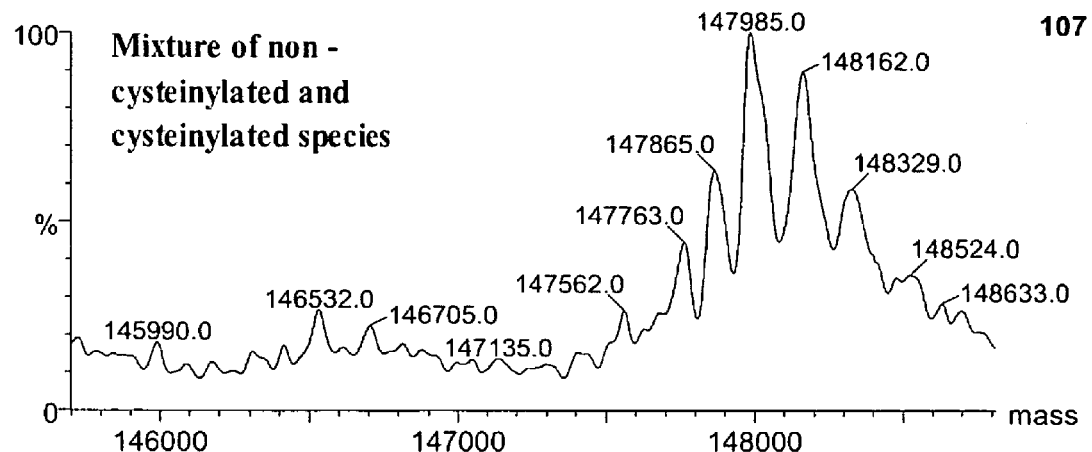
FIG. 22. Deconvoluted ESI mass spectra of IgG1 CHO bulk material (A), GuHCl refold (B) and native refold (with oxidation/reduction coupling reagents only) (C).
Figure 22B:
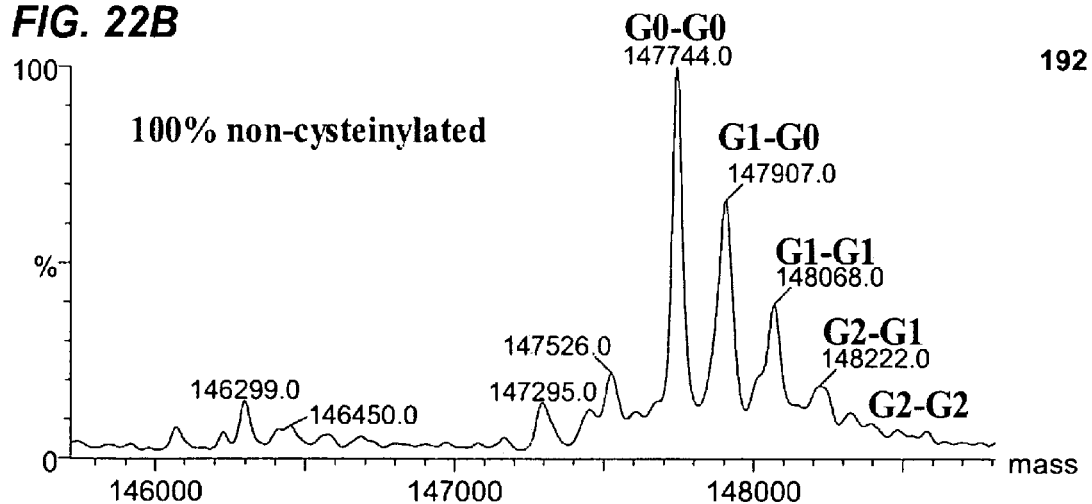
Figure 22C:
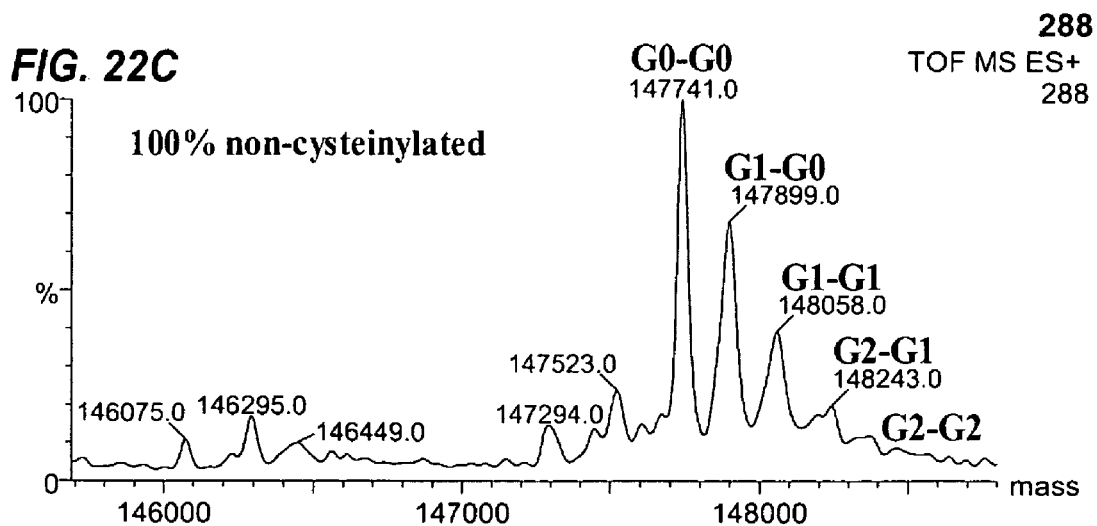
Figure 23:
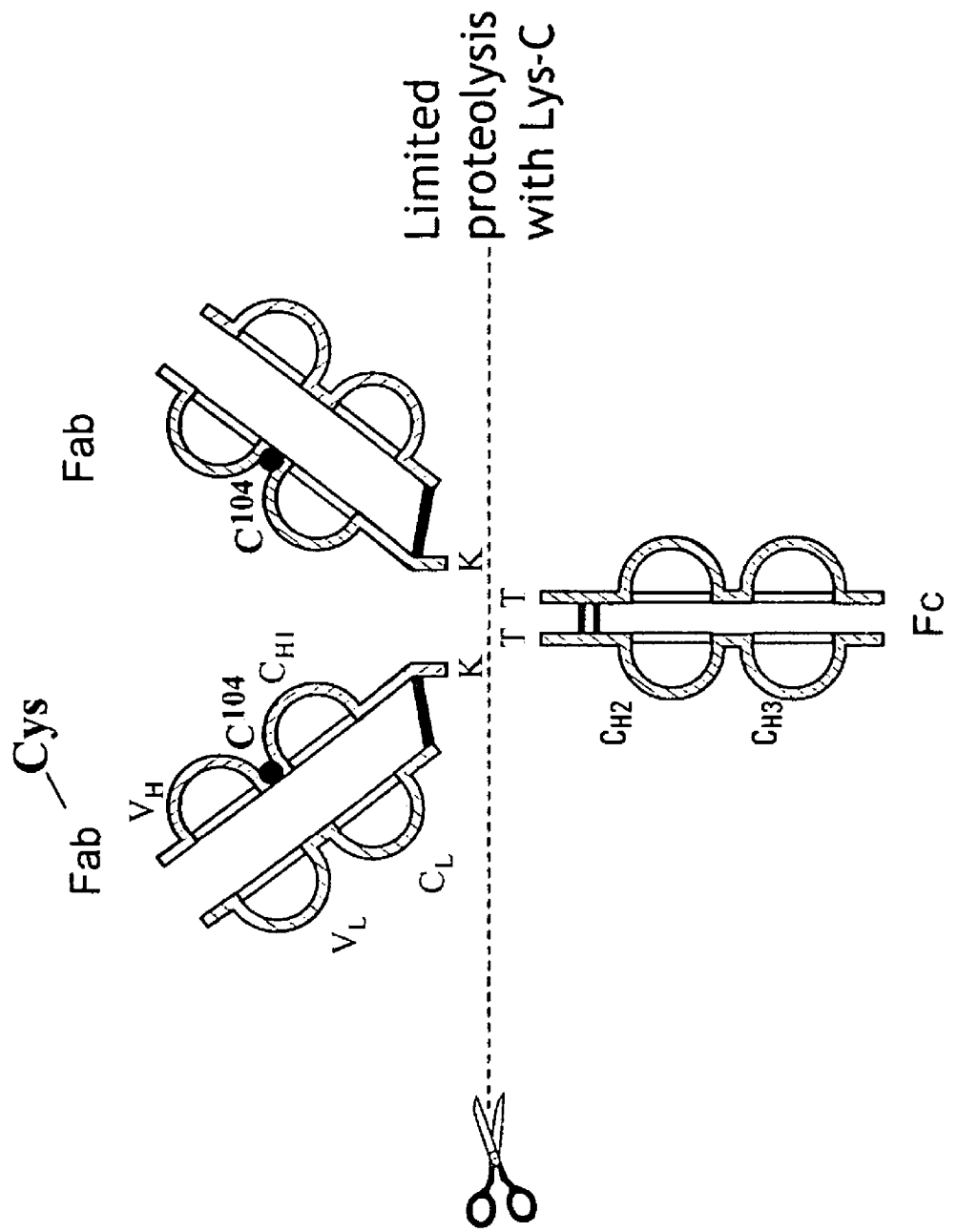
FIG. 23. Schematic of limited proteolysis using Lys-C protease produced one Fc fragment, MW=53488 Da and two Fab fragments, MW47282 each.

FIG. 22 shows deconvoluted electrospray ionization (ESI) mass spectra of IgG1 CHO control (A), GuHCl refold (B) and native refold (C). After refolding, the MW values of the samples were the same and equal to the calculated MW value within the precision of the Q-TOF mass spectrometer of +/−3 Da. (A+14-Da correction was introduced by using an additional external calibration. This correction adjusted the measured MW value of the refolded forms shown in FIG. 22B,C (147743 Da) to 147757 Da, which is within the +/−3 Da error margin from the calculated MW value of 147759 Da Anti IL-1R antibody was used as the external calibrant.) The ESI mass spectra show several peaks separated by the galactose residues (162 Da), which are the terminal residues of the two sugar moieties attached to the Fc fragment of the antibody. The peaks labeled in FIG. 22 as G0-G0, G0-G1, G1-G1, G2-G1, and G2-G2 correspond to glycosylation structure with 0, 1, 2, 3, and 4 total galactose residues per molecule of antibody. FIG. 23 shows a structure of IgG1 including the structure of the glycans (G2-G2). The different number of galactose residues is a common source of heterogeneity among all antibodies and is easily resolved by the Q-TOF mass spectrometer. FIG. 22A shows an ESI mass spectrum of the entire IgG1 CHO bulk material eluting between 10 and 13 minutes. The mass spectrum in FIG. 22A shows several additional moieties with higher molecular weight values coeluting with the galactose variants. Identification of the higher MW species was complicated while using the intact antibody molecules.

Figure 25:
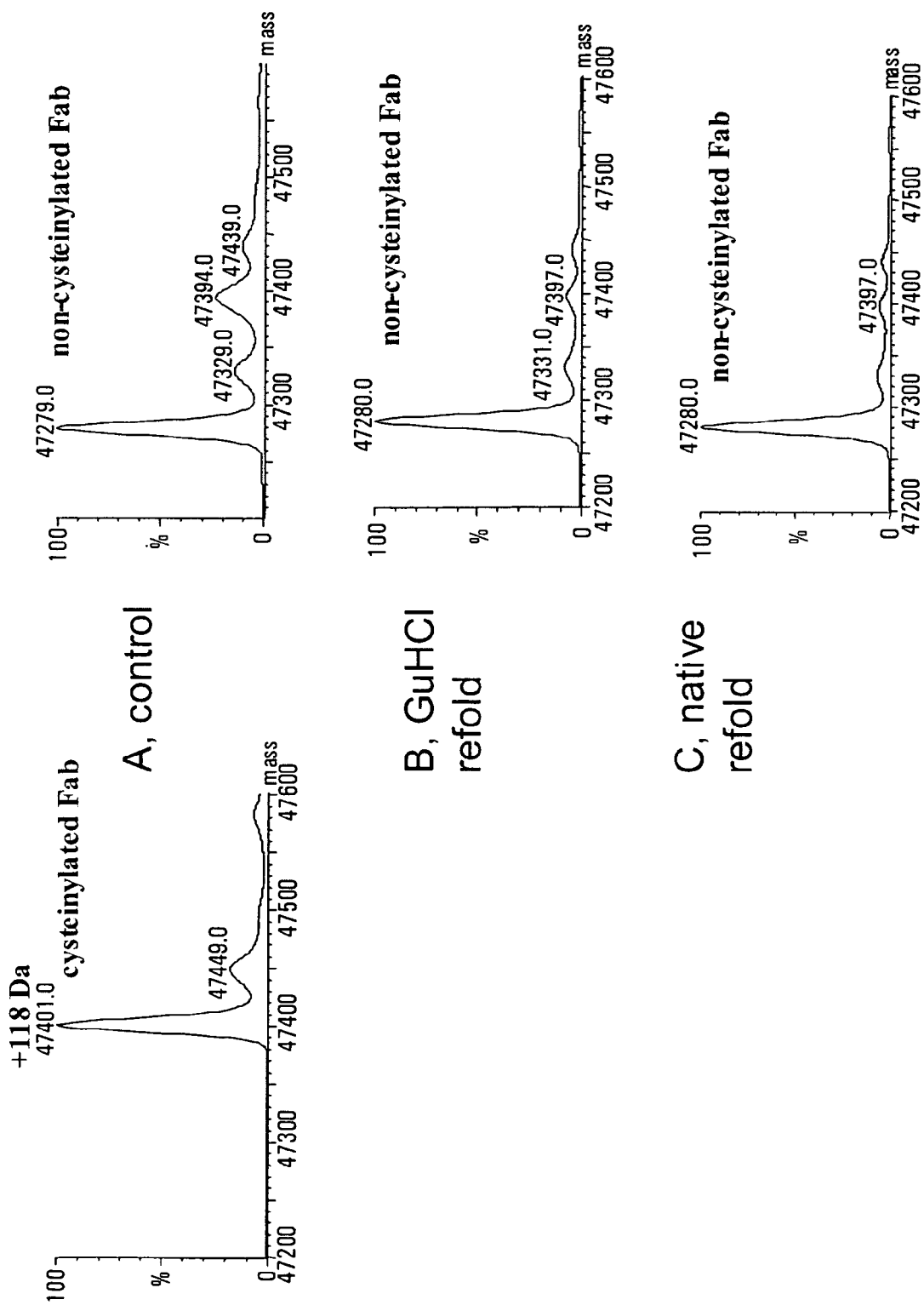
FIG. 25. Deconvoluted ESI mass spectra of Fab fragments of IgG1 CHO samples after limited proteolysis with Lys-C: A) control (bulk) material; B) GuHCl refold and C) native refold.

To further characterize the sample, limited proteolysis with Lys-C protease was performed. Lys-C when used in low concentrations preferentially cleaves at the heavy chain lysine in the hinge region of IgG1 subclass, generating Fab and Fc fragments. The IgG1 antibody was cleaved with Lys-C to produce one Fc fragment, $MW_{calculated}=53488$ Da, and two Fab fragments, $MW_{calculated}=47282$ each (FIG. 23). Limited proteolysis enhances LC/MS analysis by isolating modifications from different regions and improves resolution because of the smaller size of the fragments as compared to the intact IgG. A reversed phase chromatogram of Lys-C-treated IgG1 is shown in FIG. 23. In a typical IgG1 sample, two major peaks corresponding to the Fab and Fc fragments are observed. However, two Fab peaks were observed in IgG1 bulk material, which are attributed to additional modifications seen in this sample. The Fab fragment of refolded materials eluted mostly as a single peak, which aligned with the post-peak seen in the bulk control. FIG. 25 contains deconvoluted ESI mass spectra of Fab fragment of IgG1 before and after refolding. The measured mass of Fab fragments of refolded samples agrees well with the calculated mass and with the mass of the Fab peak 1 of the IgG1 control (FIG. 25). The Fab peak 1 of the control sample has a MW value of 118 Da higher than the calculated value, confirming cysteinylation in the Fab fragment.

Figure 24:
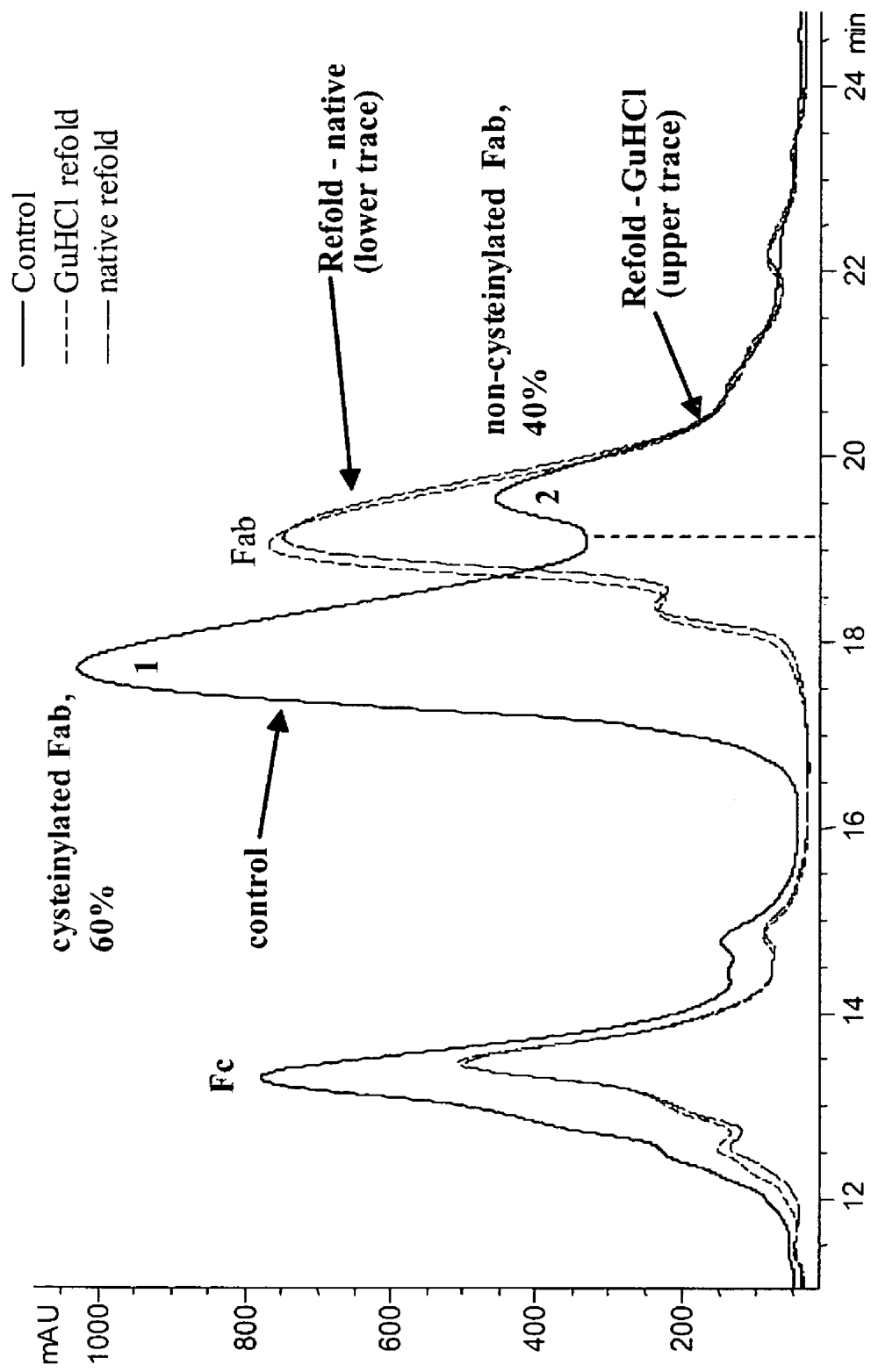
FIG. 24. RP chromatograms of IgG1 CHO after limited proteolysis with Lys-C: control (bulk) material; GuHCl refold and native refold.

Cysteinylation has been reported on proteins with free cysteines in circulation and also observed on minor impurities of light chains detected in monoclonal IgGs. In recombinant antibodies the cysteinylation is introduced during the production stage possibly due to the addition of cysteine, together with other amino acids to feed the CHO cells. The two Fab fragments eluting as peak 1 and peak 2 in FIG. 24 exhibited great chromatographic separation, which should be caused by greater structural differences than just cysteinylation. For example, cysteinylated and non-cysteinylated light chain impurities co-elute on the RP chromatograms. The drastic difference in elution times of Fab fragments was the other clue suggesting that disulfide scrambling may be involved.

Figure 26:
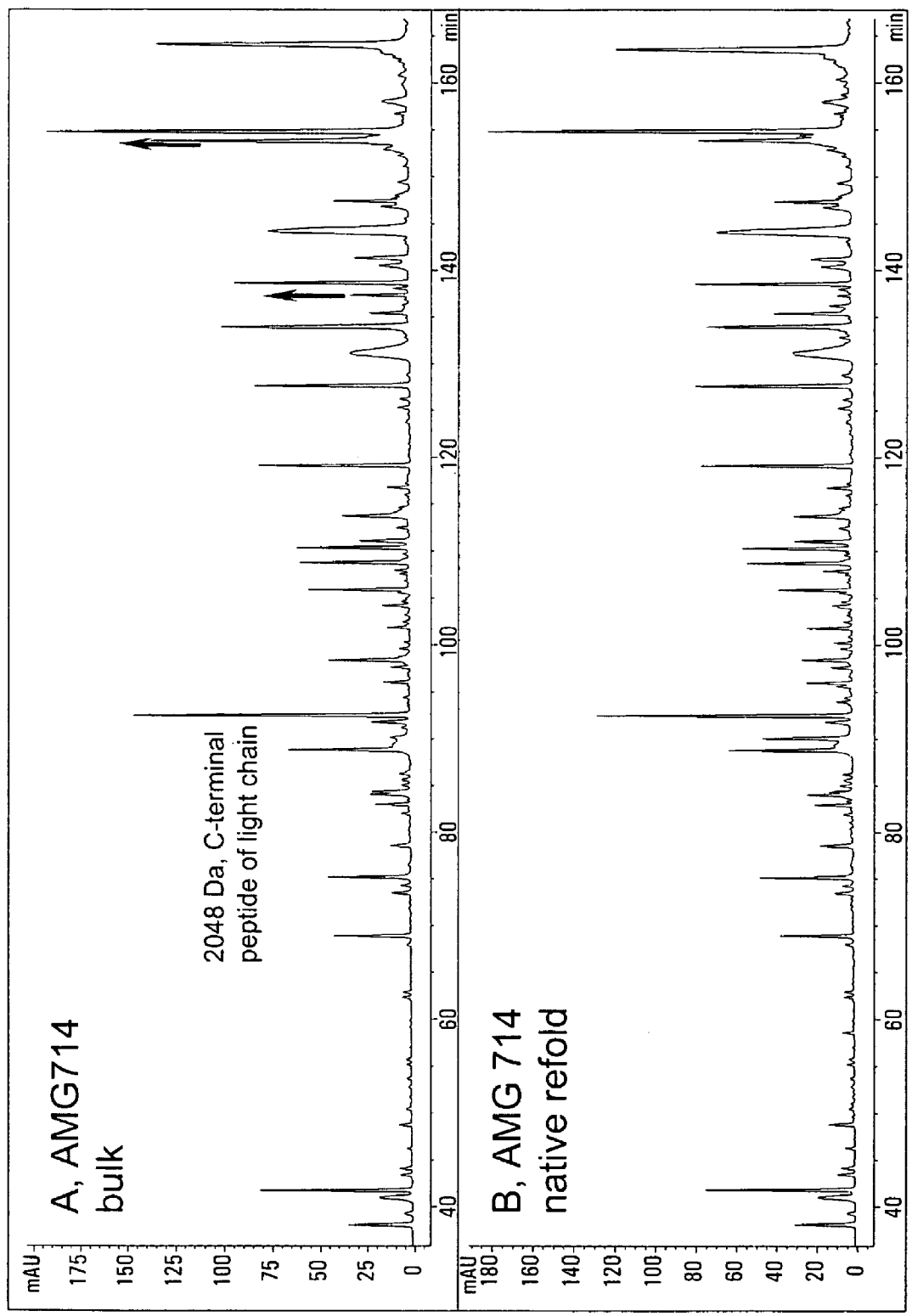

FIG. 26 shows non-reduced Glu-C peptide maps of IgG1 control (bulk) and native refold. Although the two peptide maps are almost perfectly aligned, there are differences in intensities of at least three peptides marked with red arrows in FIG. 25. Further identification and assignment of the disulfides may now be performed.

Tables Y contain results of the cell based biological activity assays performed by monitoring IgG1 dose response with 200 pg/mL and 50 pg/mL IL-15. Table Z contains results of the cell based biological potency measurements. Both assays show that cell based biological activity doubled after the refolding by using either the native refolding or GuHCl refolding.

TABLE Y

Bioassay results for 146B7 controls, GuHCl refold, and native refold. Assay performed by Nicholas Yeager.

| Curve Midpoints | 200 pg/mL IL-15 | 50 pg/mL IL-15 |
|---|---|---|
| 146B7-CI | 15.73 | 1.544 |
| Native Refold | 9.09 | 1.162 |
| 146B7-GuHCl | 7.635 | 1.021 |
| 146B7-Pharm. | 22.438 | 2.488 |

TABLE Z

Bioassay results for 146B7 controls, GuHCl refold, and native refold.

| 146B7 | Expected Protein Conc. (mg/mL) | Biol. Active Protein Conc. (mg/mL) | Relative Potency (n = 3) Mean (%) | CV (%) |
|---|---|---|---|---|
| Assay Control | 63.00 | 67.51 | 107 | 8 |
| Hybridoma-derived | 20.00 | 27.99 | 140 | 6 |
| CHO-derived, GdnHCl-treated Refold | 2.49 | 5.85 | 235 | 6 |
| CHO-derived, Native Refold | 2.66 | 5.60 | 211 | 4 |
| CHO-derived, A5S Control | 5.47 | 6.41 | 117 | 5 |

Figure 27:
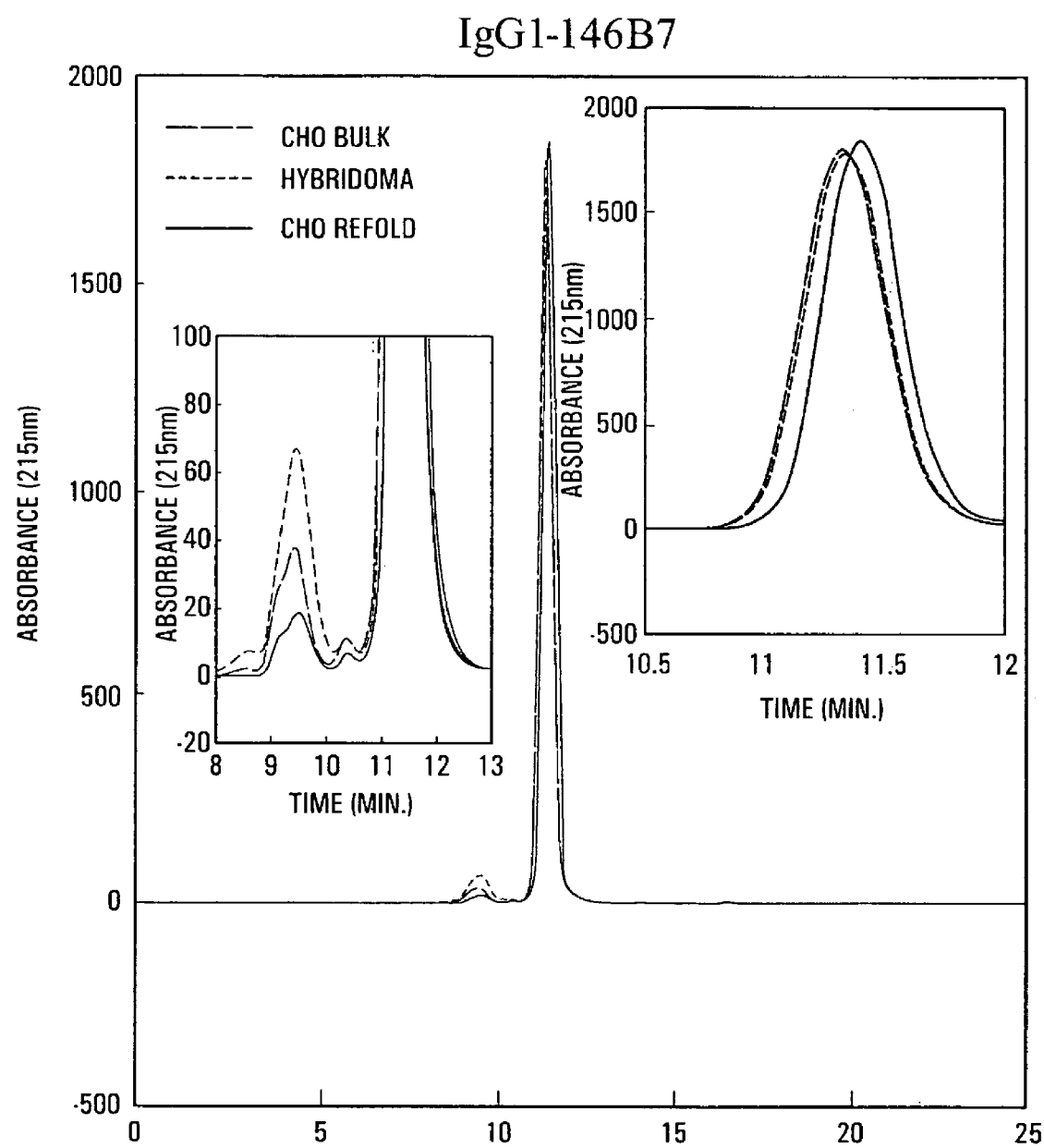
FIG. 27. Size exclusion chromatograms of IgG1: CHO bulk, hybridoma bulk, and CHO refold.

FIG. 27 shows SEC chromatograms of IgG1 CHO bulk, GuHCl refold, and hybridoma material. The chromatograms indicate an increase in retention time of the refolded material suggesting a change in conformation relative to the bulk and hybridoma proteins. A decrease in the aggregate peak of refolded material was also observed.

Figure 28B:
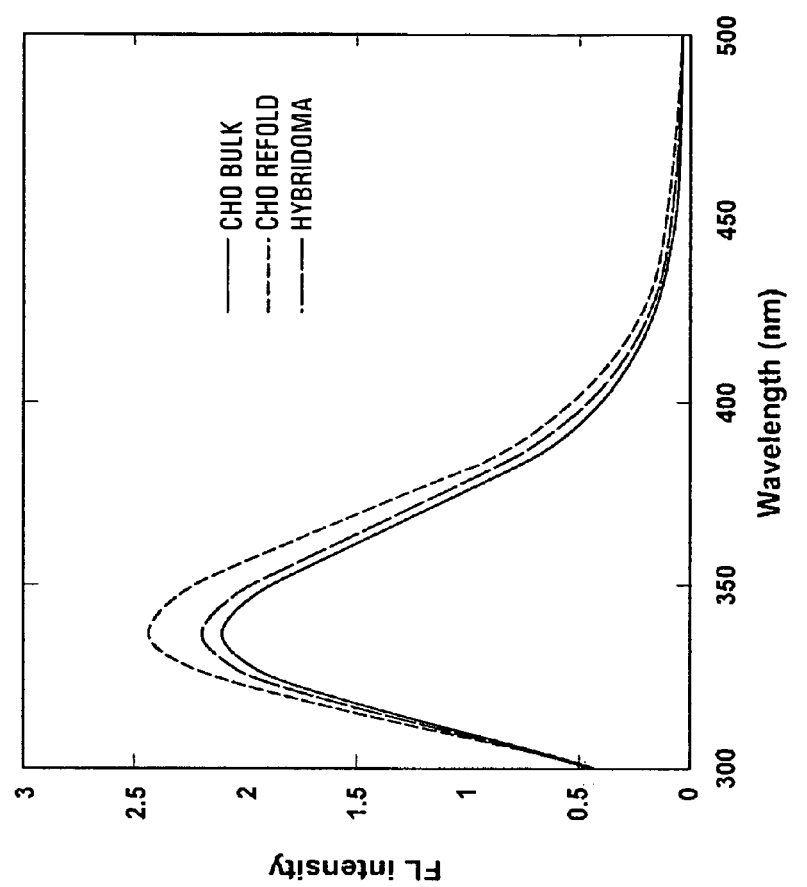
FIG. 28. CD and fluorescence measurements of IgG1: CHO bulk, hybridoma bulk, and CHO refold.
Figure 28A:
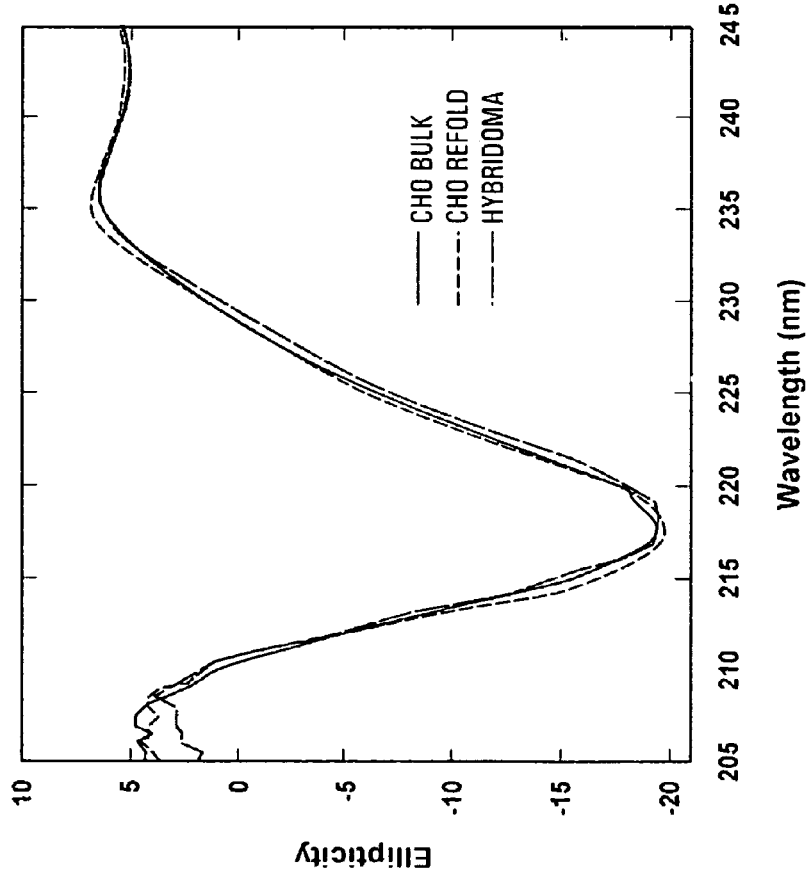

CD and fluorescence spectroscopy analyses are shown in FIG. 28. Panel A indicates that there is no change in secondary structure of IgG1 after the refolding. Panel B shows an increase in the fluorescence intensity after refolding relative to both the CHO bulk and hybridoma material. This may be due to structural changes in the microenvironment(s) of the fluorescing tryptophan residues after refolding. The fluorescence intensity of the hybridoma derived protein is greater than the CHO bulk protein. This may correlate with the greater bioactivity data for the hybridoma material relative to the CHO bulk material. The hybridoma derived protein was stored in PBS pH 7.4 prior to being diluted, a pH is more conducive to disulfide exchange reactions than the A5S storage conditions used for the CHO bulk protein. There is no appreciable change in the emission maximum wavelength between samples suggesting that the polarity of the tryptophan environment remains the same.

Summarizing the above studies, during the course of gathering the above data it was learned that IgG1 CHO bulk material is structurally heterogeneous and includes molecules with cysteinylated cysteine in Fab fragment. Approximately 60% of all Fab fragments were cysteinylated. Because of the great difference in elution of cysteinylated and non-cysteinylated Fab fragments and because of the presence of the unique non-paired cysteine in the anti-IL-15 IgG1, the inventors proposed that cysteinylation is associated with disulfide bond scrambling. The IgG1 bulk material was refolded with and without chaotropic agent (0.9 M GuHCl and no GuHCl). Both refolds produced a homogeneous non-cysteinylated 146B7 molecule according to accurate mass measurements by a Q-TOF mass spectrometer. After 24 hours most of the 146B7 bulk was refolded into the later eluting homogeneous species. After 48 hours the refold was almost complete. Cell based biological activity was performed and revealed that the refolded samples were two-fold more active as compared to the IgG1 CHO bulk material that had not been refolded.

The data in this example show that the cysteinylated species elute earlier from the RP column as identified by mass spectrometric measurements and are eliminated after refolding. The RP LC/MS technique employed in this study was especially effective, because of the apparent association between the misfolding and cysteinylation.

The above-presented data show that the refolded the IgG1 molecules are more homogeneous and more active after the refolding. Further optimization and characterization may now be performed based on the studies and techniques taught herein.

Example 6

Methods for Refolding of Recombinant Antibodies that Bind Interleukin-15

The present Example provides a comparison of different lots of 146B7 using limited proteolysis followed by RP LC/MS analysis. In the data presented in this Example, different lots of 146B7 were compared for the levels of cysteinylation on C104 in heavy chain using limited proteolysis followed by RP LC/MS. Levels of oxidation, succinimide and galactose content for different lots were also calculated. The site of cysteinylation and oxidations were identified using peptide mapping.

The levels, for cysteinylation, oxidation, galactose content and succinimide varied in different lots. There was significant variability between CHO and hybridoma derived material. Refolding of CHO derived 146B7 leads to the loss of cysteinylation. Refolding does not cause any other modifications and the two materials look comparable by peptide mapping. For hybridoma, CHO PD, and CHO PD refold materials, bioactivity increases with decreasing amount of cysteinylation.

| Lot # | Hex I | % Ox | % Succinimide | % Cys (free) | Bioactivity (Anal. Sci.) |
|---|---|---|---|---|---|
| Hybridoma | 1.1 | 13 | 13 | 54 (46) | 135 |
| CHO PD (1) | 0.8 | 7 | 18 | 74 (26) | 105 |
| CHO PD (1) refold | 0.9 | 7 | 15 | 0 (100) | 211 |
| C104S | 0.5 | 4 | 18 | 0 (100) | |
| CHO ProSci (1) | 1.3 | 4 | 11 | 74 (26) | 168 |
| CHO ProSci (2) | 1 | 6 | 11 | 50 (50) | 201 |

The levels (percentages of the three modifications were calculated independently and do not add to 100% in the above table. For example, 13% of cysteinylated molecules of hybridoma are also oxidized, while the other 87% of cysteinylated molecules are not oxidized.

Hex I is the average number of Hexose (Galactose) molecules per molecule of IgG and identification of cysteinylation and refolding of the IgG1 are described above in other examples.

Figure 29:
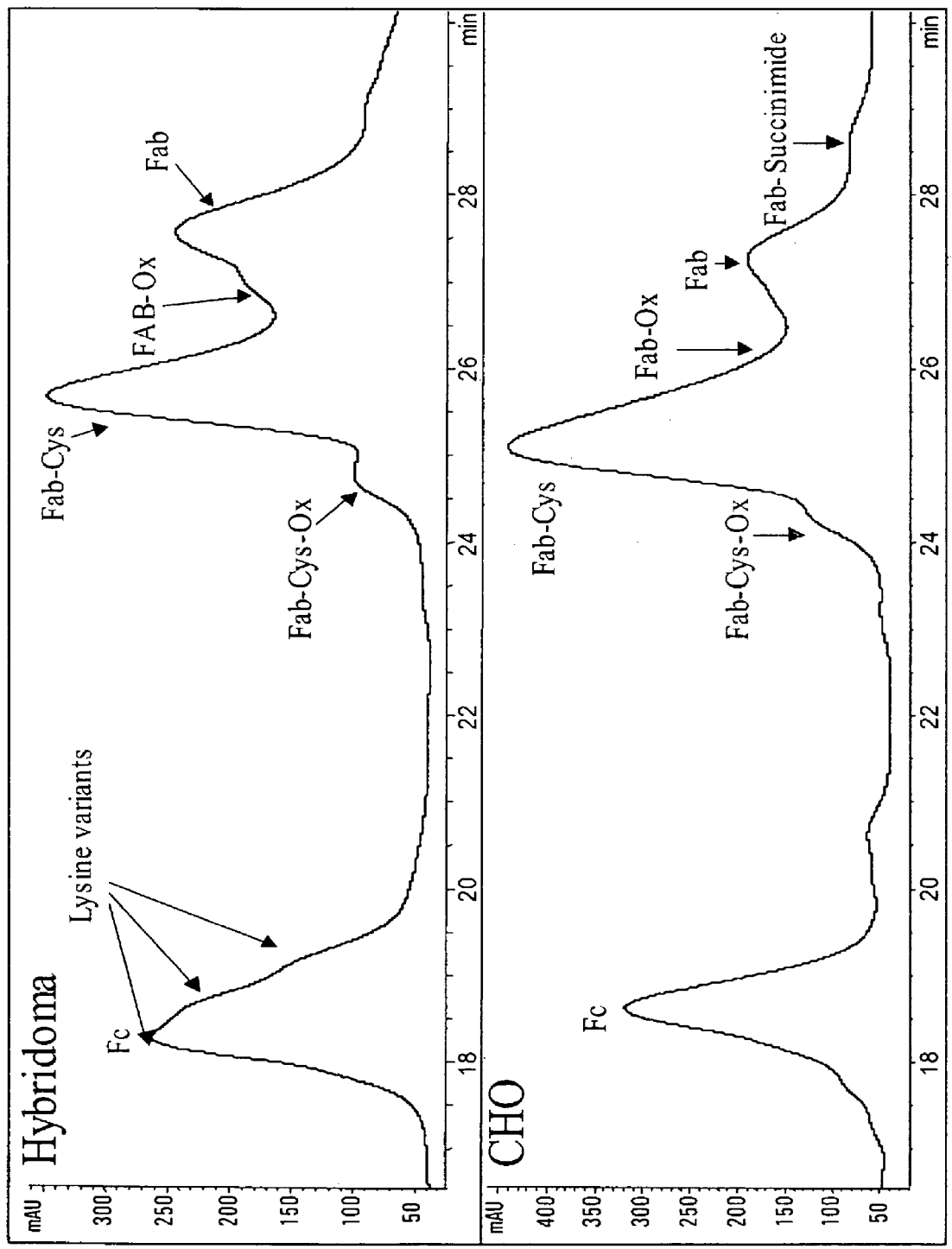
FIG. 29. Reversed phase chromatograms of IgG1 hybridoma and CHO after limited proteolysis. Cysteinylated (Fab-Cys) and non-cysteinylated (Fab) fragments are separated and quantified.
Figure 30:
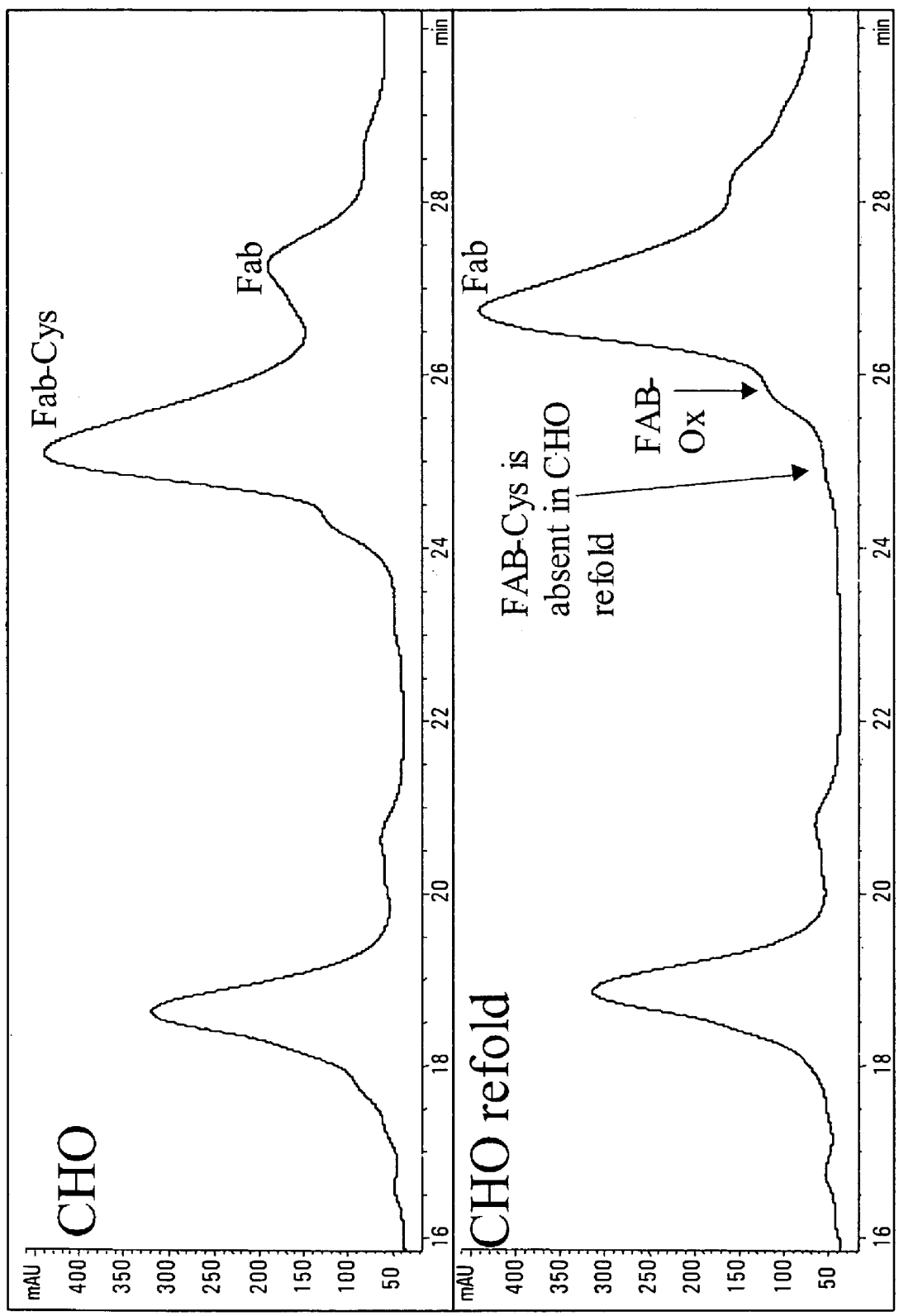
FIG. 30. Reversed-phase chromatograms of IgG1 before and after refolding after limited proteolysis. Cysteinylated (Fab-Cys) and non-cysteinylated (Fab) fragments are separated and quantified.
Figure 31:
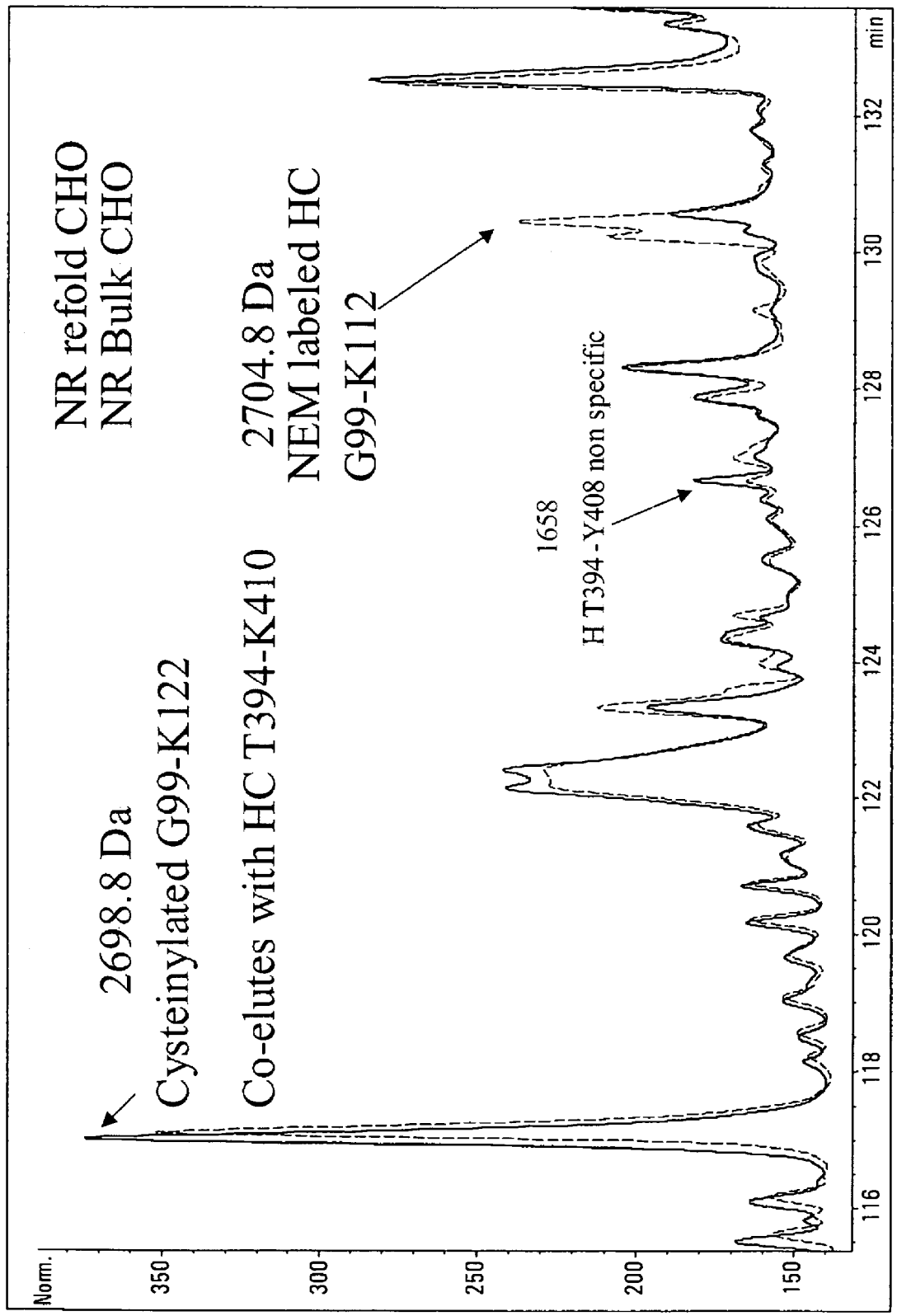
FIG. 31. Non-reduced peptide mapping of IgG1 using trypsin after labeling of free cysteines with NEM at pH5. Location of cysteinylation was identified in position C104 of heavy chain.
Figure 32:
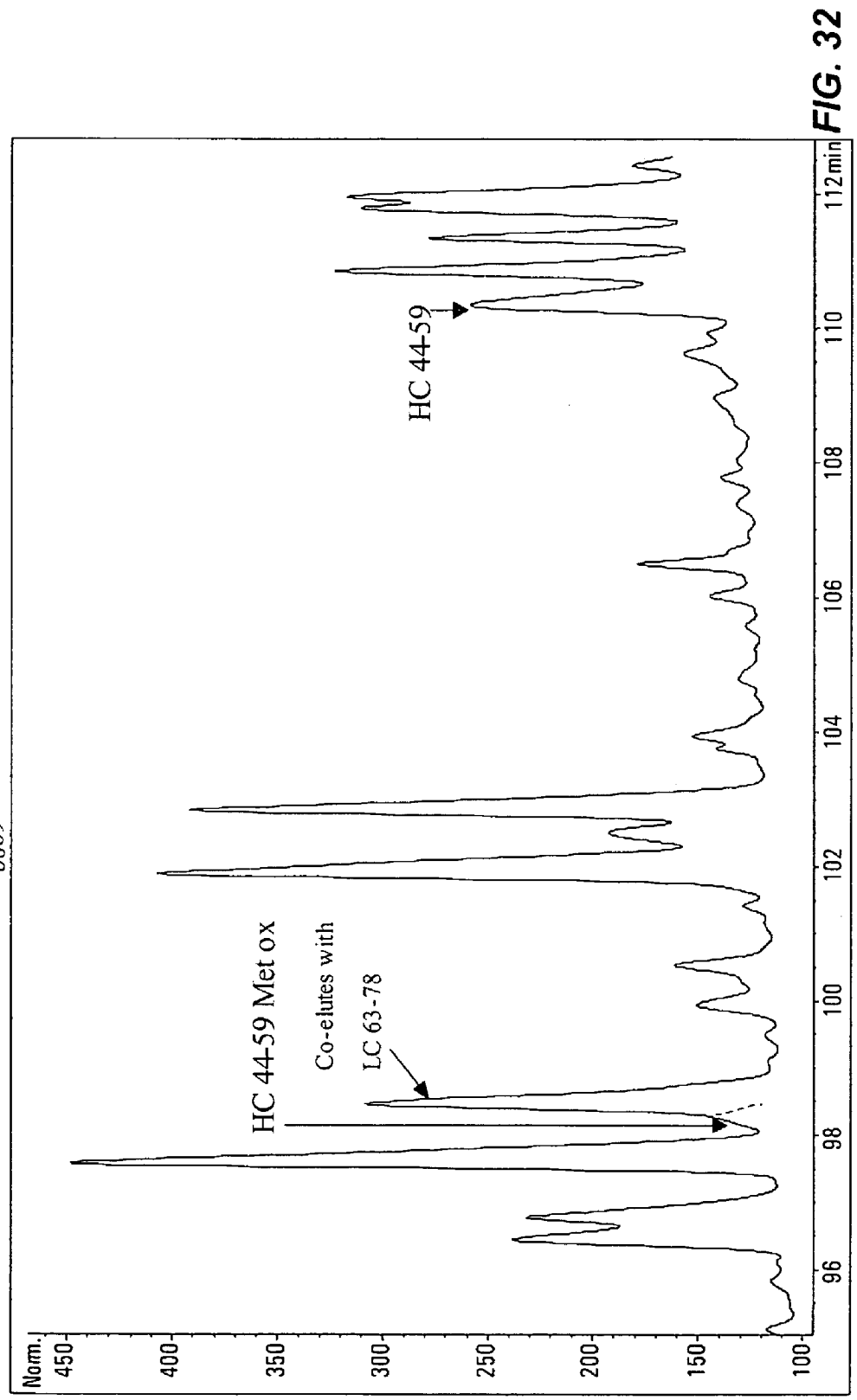
FIG. 32. Identification of methionine 48 oxidation in HC CDR2 region. A small percentage of M48 in HC CDR2 was oxidized according to the non-reduced peptide map.
Figure 33:
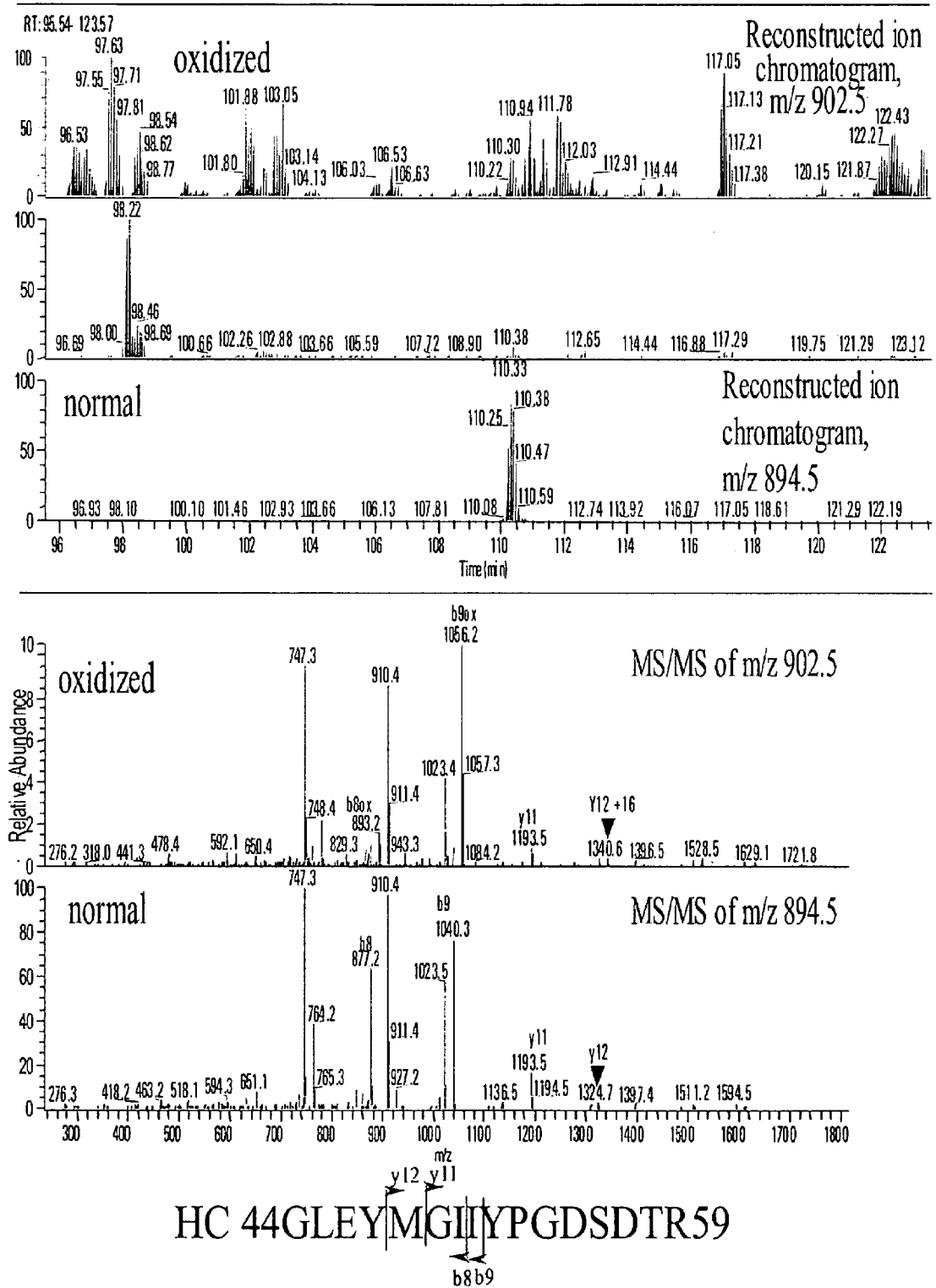
FIG. 33. Reconstructed ion chromatograms (top) and fragmentation mass spectra (bottom) from IgG1 non-reduced peptide map showing identification of methionine 48 oxidation in HC CDR2 region using MS/MS analysis. Approximately 10% of the methionine 48 is oxidized. The oxidized peptide elutes at 98 minutes, non-oxidized at 110 minutes.

The data from these experiments are consistent with those shown in Examples 4 and 5. In FIG. 29, there is shown another RP chromatograph of the IgG1 hybridoma and CHO after limited proteolysis. The cysteinylated and non-cysteinylated fragments may readily be separated and quantified. In FIG. 30 RP chromatograms of IgG1 before and after refolding are shown showing the absence of Fab-Cys in the refolded preparation. In the non-reduced peptide map of the IgG1 after labeling of the free cysteines with NEM, the CHO material before and after refold looks comparable by peptide mapping. IgG1 bulk material contains a large abundance of the tryptic peptide G99-K122 with cysteinylated C104 eluting at 117 minutes. After refolding, the abundance of cysteinylated peptide decreased and abundance of the non-cysteinylated peptide increased. The non-cysteinylated peptide was labeled with NEM to prevent it from scrambling with other cysteine residues during reduction, alkylation and digestion. FIG. 30 depict the non-peptide mapping of the IgG1 using trypsin after labeling of free cysteines with NEM at pH5. The cysteinylation location was identified as being at position C104 of the heavy chain. Methionine 48 oxidation in the heavy chain CDR2 region also was identified (FIG. 32). According to the non-reduced peptide map, a small percentage of the M48 in the heavy chain CDR2 was oxidized. Oxidized peptide elutes at 98 minutes and non-oxidized peptide elutes at 110 minutes. As can be seen from FIG. 32, the reconstructed ion chromatograms and fragmentation mass spectra show that approximately 10% of M48 is oxidized.

Example 7

Refolding of Recombinant Antibodies on Protein A Column for Scale-up Process The data present throughout the present application show that in general for purified IgG 2, three peaks are observed in RP HPLC methods described herein. Further, the three peaks can be converted into either peak 1 or peak 3 by using reduction/oxidation reagents with GuHCl or without GuHCl. The heterogeneity of an antibody population is due to di-sulfide bonds scrambling. This heterogeneity can be resolved refolding as described herein. From certain bioassay data it seems that the antibody population eluting from peak 1 on the chromatogram is more stable and that eluting from peak 3 is the most active with a relative stability after reduction-oxidation.

In the present Example, data are provided to show an on-column refolding of the IgG molecules. More particularly, the a protein A affinity column is designed for IgG red-ox or refolding carrier. The column resin can handle 1-2M GuHCl, as well as reducing agents such as cysteine/cystine. The resin is run at pH 7.2 or high, a pH well suited for reduction-oxidation processing of the IgGs being separated.

| 1. Redox or Refolding in Solution | | | | | | |
|---|---|---|---|---|---|---|
| Run ID | IgG2 (mg/mL) | Cysteine (mM) | Cystine (mM) | Temp (° C.) | 1M Guanidine | Incubation Time |
| 1 | 3 | 0 | 0 | No redox | No redox | 48 hrs |
| 2 | 3 | 6 | 0.6 | 4 | Yes | 48 hrs |
| 3 | 5 | 6 | 0.6 | 4 | Yes | 48 hrs |
| 4 | 10 | 6 | 0.6 | 4 | Yes | 48 hrs |
| 5 | 10 | 10 | 0.6 | RT | Yes | 48 hrs |
| 6 | 3 | 6 | 0.6 | RT | Yes | 48 hrs |
| 7 | 3 | 6 | 0.6 | 4 | no | 48 hrs |
| 8 | 5 | 6 | 0.6 | 4 | no | 48 hrs |
| 9 | 10 | 6 | 0.6 | 4 | no | 48 hrs |
| 10 | 10 | 10 | 0.6 | RT | no | 48 hrs |
| 11 | 3 | 6 | 0.6 | RT | no | 48 hrs |

The above table provides exemplary components of a refolding reaction mixture that can be used for refolding IgGs in solution. Adapting the above technique for on-column processing, the following Table provides that parameters for redox processing of an IgG2 on a Protein A affinity column.

| 2. IgG2 Redox on Protein A Affinity Column | |
|---|---|
| Process Condition: | |
| Parameter | Condition |
| Equilibration | 3-5 CV-100 mM NaCl, 20 mM Tris, pH 7.4 at 300 cm/hr |
| Load | Target load of 10 or 20 mg/ml at 300 cm/hr |
| Wash 1 | 3 CV-200 mM Tris pH 8.0 at 300 cm/hr |
| Wash 2 Redox | 2, 6 and 12 hr with or without GuHCl at 50 cm/hr pH 8.0 |
| Wash 3 | 5 CV-100 mM NaCl, 20 mM Tris, pH 7.4 at 300 cm/hr |
| Elution | 5 CV-50 mM NaAOc pH 3.4 at 200 cm/hr |

| Run ID | IgG2 (mg/mL) | Cysteine (mM) | Cystine (mM) | Temp (° C.) | 1.2M Guanidine | Redox Time |
|---|---|---|---|---|---|---|
| 1 | 20 | 20 | 0.6 | 4 | Yes | 2 hrs |
| 2 | 20 | 20 | 0.6 | 4 | Yes | 6 hrs |
| 3 | 20 | 20 | 0.6 | 4 | Yes | 12 hrs |
| 4 | 10 | 10 | 0.6 | 4 | Yes | 2 hrs |
| 5 | 10 | 10 | 0.6 | 4 | Yes | 12 hrs |
| 6 | 20 | 20 | 0.6 | 4 | no | 2 hrs |
| 7 | 20 | 20 | 0.6 | 4 | no | 6 hrs |
| 8 | 20 | 20 | 0.6 | 4 | no | 12 hrs |
| 9 | 10 | 10 | 0.6 | 4 | no | 2 hrs |
| 10 | 10 | 10 | 0.6 | 4 | no | 12 hrs |

Purified IgG1 samples were treated with redox pairs of varied concentrations and at both pH 7 and 8 and for varying amounts of time. In some exemplary studies treatment lasted about 24 hours at 2-8° C. The reaction was stopped by lowering the pH of the samples to about pH 5. The bioassay activities were presented as a percentage of activity of the untreated IgG1 (see table below). Redox conditions including room temperature, shorter duration (e.g. 3 hours) have also been carried out and found to improve the bioassay activity of 146B7.

TABLE

| Cell-Based Bioassay Activity or Potency after Redox-Treatment | | | | | |
|---|---|---|---|---|---|
| # | pH | Cysteine (mM) | Cystanine (mM) | Cystine (mM) | Ratio | Potency |
| 1 | 7 | 6 | 0.3 | | 20 | 184 |
| 2 | 8 | 6 | 0.3 | | 20 | — |
| 3 | 7 | 6 | 0.6 | | 10 | 197 |
| 4 | 7 | 3 | 0.3 | | 10 | — |
| 5 | 8 | 3 | 0.6 | | 5 | — |
| 6 | 7 | 3 | 0.6 | | 5 | 189 |
| 7 | 8 | 6 | 0.6 | | 10 | 211 |
| 8 | 8 | 3 | 0.3 | | 10 | — |
| 9 (Crtl) | 8 | 6 | | 0.6 | 10 | 203 |
| 10 | 8 | 1.5 | 0 | | | 212 |

Figure 34:
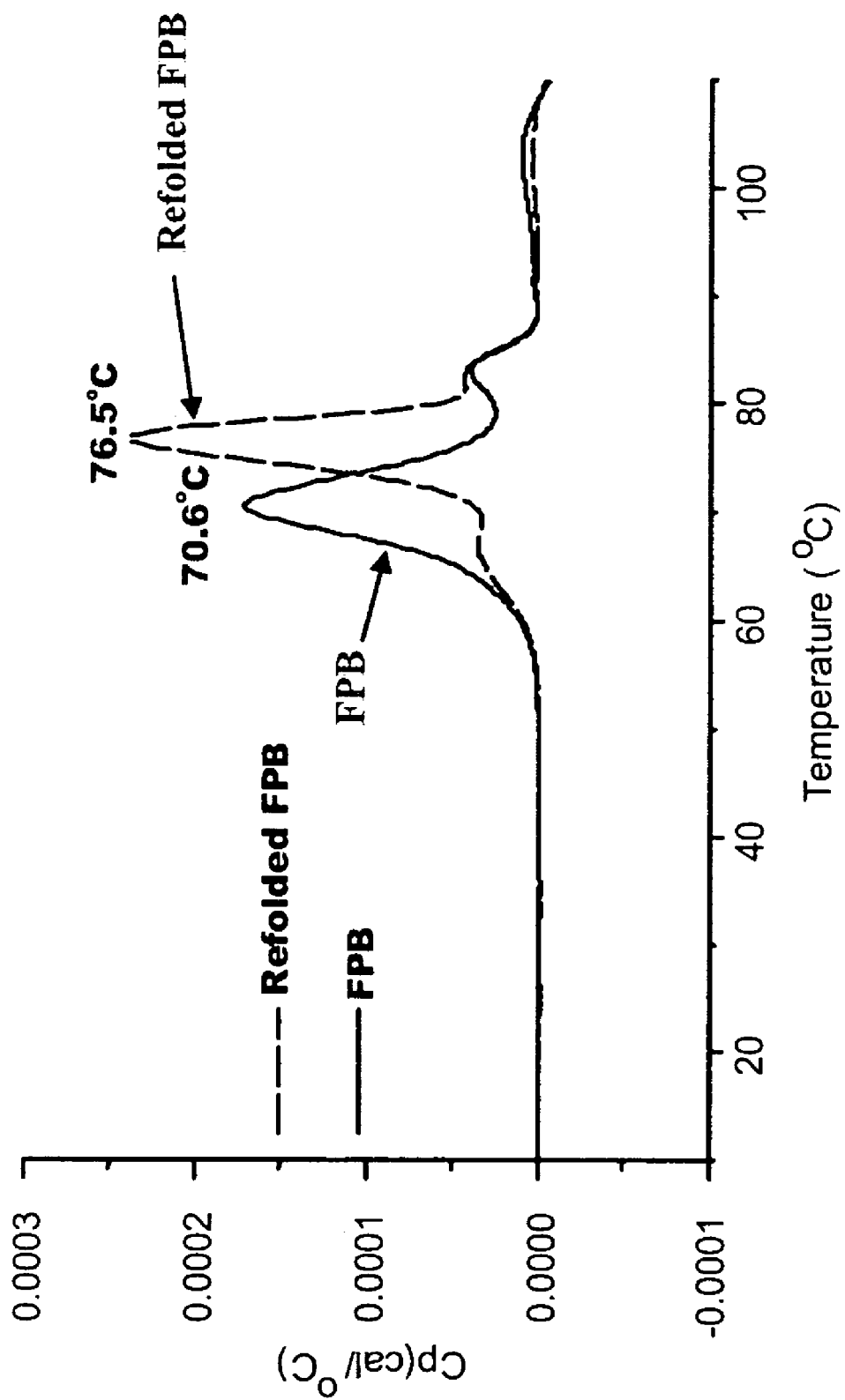
FIG. 34. Differential calorimetry scanning (DSC) measurement of IgG1 before and after redox treatment or refolding.

In FIG. 34, it is seen that the melting point of IgG1 was increased after the redox treatment as measured by DSC, which indicated higher thermostability. To generate these data, IgG1 was treated with 6 mM cysteine, 0.6 mM cystine, pH 8 over night at 2-8° C.

The IgG1 was also treated with reductant alone, without the addition of oxidant, as shown in Experiment #10, in the above Table. In that example, purified IgG1 was incubated with 1.5 mM cysteine overnight at 2-8° C. Its activity was increased by about 2 fold. This will certain embodiments contemplate the use of both reductant and oxidant, it is contemplated that the antibody refolding may be performed using reductant alone.

Figure 35:
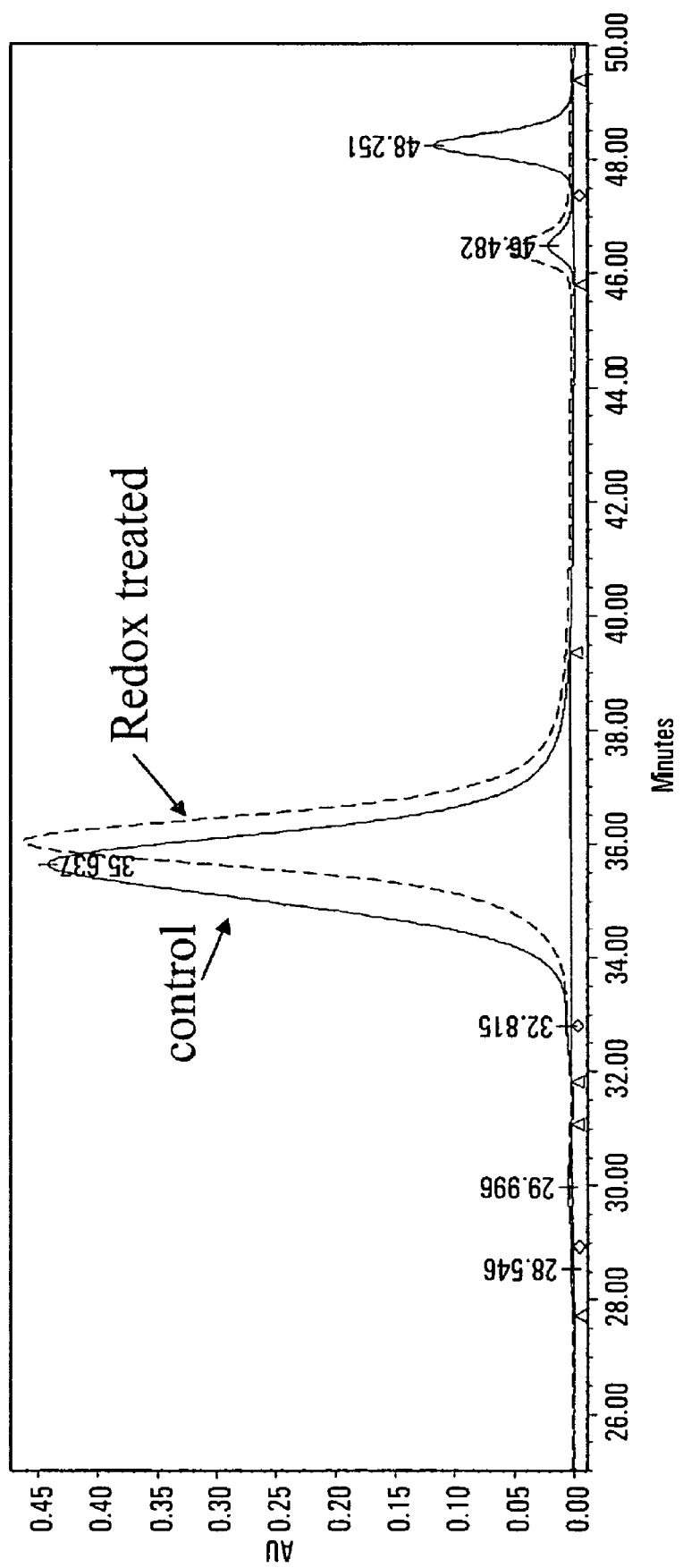
FIG. 35. SEC-HPLC chromatography of Protein A affinity column purified IgG1 from cell culture medium with redox treatment or without redox treatment.

As discussed in the some embodiments, the refolding may be achieved by adding the refolding agent to the cell culture, the antibody alone or even by separating the antibody using a column that contains the redox agents. In certain exemplary embodiments, the IgG1 was refolded in the cell culture medium where it was produced. Clarified cell culture medium was treated with redox pair (6 mM cysteine, 0.6 mM cystine, 2-8° C. overnight). The IgG1 was then purified with Protein A affinity chromatography. In this particular case, the refolding was observed with a shift in its retention time on SEC-HPLC (FIG. 35). Refolded IgG2 consistently showed longer retention time on-SEC-HPLC, and as such the SEC-HPLC method may be used to as refolding-indicating assay method.

During large-scale production of the IgG1 antibody, in some embodiments, it is contemplated that the redox-treatment step could readily be introduced before the cation exchange chromatography step to refold the antibodies in order to eliminate cysteinylation of free cysteines. This produces an antibody population that has a reduction in the structural heterogeneity, and/or increased biological activity and/or improved stability and shelf life.

Example 8

Stability Study of Refolded an anti-IL15 IgG1 Antibody

Denaturation curves may be used to obtain an estimate on the conformational stability of proteins and are well suited for measuring stability differences between proteins differing in chemical or conformational structure (Pace, C. N., Methods in enzymology 1986 vol. 131, 267-280.) In cases where the equilibrium curves may be fit to a particular unfolding mechanism a free energy of unfolding or a measure of how much more stable the native conformation is from the unfolded state may be obtained. Typically what is done is the protein is unfolded and equilibrated at varying concentrations of chemical denaturant and a spectroscopic signal recorded at each of these denaturant concentrations. With knowledge of the signal in the folded region of the curve (native baseline) and the unfolded region (unfolded baseline) an equilibrium constant (and thus change in free energy) may be obtained at each denaturant concentration within the unfolding transition region. The values for the changes in free energy may then be extrapolated back to the absence of denaturant to yield the change in free energy of the protein unfolding in water.

Different spectroscopic methods will report on different unfolding events, for example fluorescence is used to probe tertiary structure unfolding and circular dichroism is used to monitor unfolding of secondary structure. For a more complete description of the method, refer to the Pace text cited above.

For the comparison of anti-IL-15 IgG1 pre and post redox treatment 1 mg/mL protein was equilibrated overnight at the guanidinium hydrochloride concentrations shown in the graph. Samples were then analyzed by exciting at 295 nm and monitoring the fluorescence emission at 360 nm (see FIG. 36). CD data was also recorded by monitoring CD at 218 nm (data not shown). Unfortunately, after normalizing the FL and CD data to the fraction unfolded the signals from the two spectroscopic probes did not overlay suggesting a on-two state unfolding transition that can not at this time be easily fit to yield a free energy difference that may be compared between the redox and non-redox treated samples. The FL graph, however, does show that the midpoint (Cm) of this transition is greater for the redox treated sample than for the non-redox treated bulk material suggesting the stability of the redox-treated 146B7 IgG1 antibody to be greater than the bulk non-redox treated sample. This may be the case and is supported by the shift in Tm seen for thermal denaturation experiments, however, without an adequate fit of the data taking into consideration the apparent differences in m-values one can only say that there are apparent differences in the equilibrium unfolding between the redox and non-redox treated 146B7 IgG1 proteins.

Figure 37B:
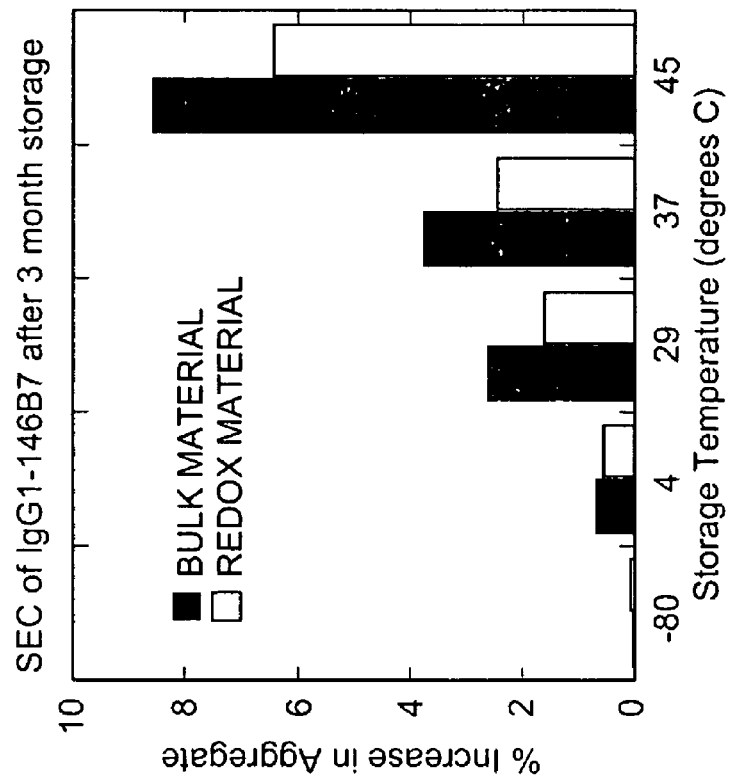
FIG. 37. Size exclusion chromatography (SEC) data for a comparison study of bulk and redox-treated 146B7 IgG1 antibody. Panel A is three month data for the percent decrease in main peak monomer species for storage temperatures of −80, 4, 29, 37, and 45° C. Panel B is three month data for the percent increase in pre-monomer aggregate species for storage temperatures of −80, 4, 29, 37, and 45° C.
Figure 37A:
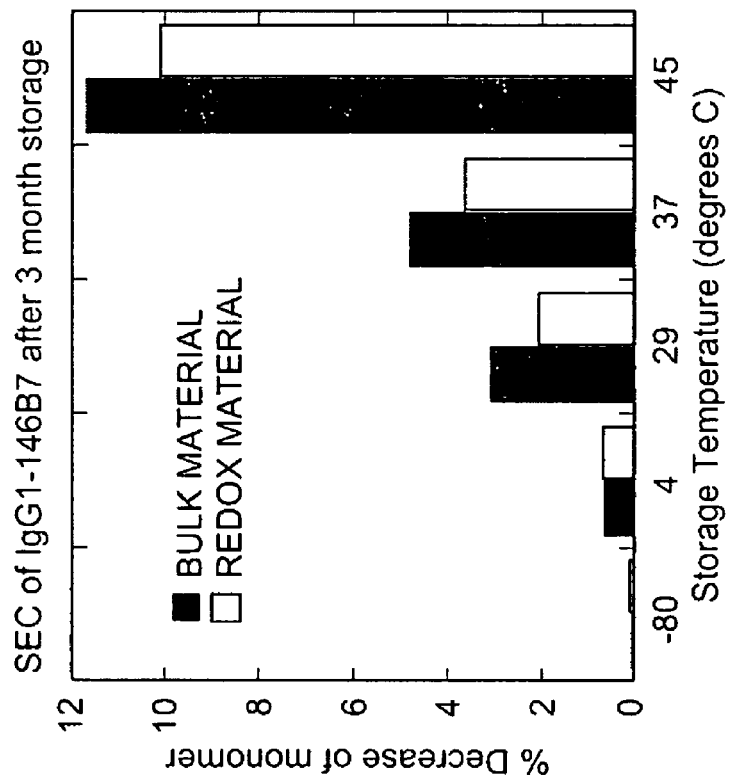

An accelerated stability study was performed comparing the non-redox treated bulk IgG1 and the redox-treated 146B7 IgG1 antibody. Both proteins were formulated at 100 mg/mL in A5S buffer (10 mM sodium acetate, pH 5, 5% sorbitol) and stored at the following temperatures: −80, 4, 29, 37, and 45° C. At various time points samples of both proteins were pulled and analyzed for degradation. The methods employed were size exclusion chromatography (SEC) to monitor high MW aggregates and low MW protein clips, SDS-PAGE, and particle counts to measure insoluble aggregates. Protein concentration as well as pH was also measured at each time point. The graph in FIG. 37 is representative SEC data for the three month time point showing that the non-redox treated sample has a propensity toward aggregation at a faster rate than the redox-treated anti-IL-15 IgG1 at all liquid temperatures. Clipping reaction remained the same for either sample (data not shown).

Example 9

Production of Enriched Population of Intact IgG4

The present Example is directed to producing an enriched population of covalently bound intact monoclonal IgG4 antibodies by refolding the half molecules of IgG4 into covalently bound intact molecules of IgG4. The recombinant monoclonal IgG4 produced in mammalian cells and is a heterogeneous population of IgG4 molecules containing half-molecules and covalently bound intact molecules of IgG4. This heterogeneous population is contacted with reduction-oxidation reagents in the presence of a denaturing reagent to produce intact IgG4 molecules. After performing the redox treatment, the antibody is formulated in a stable buffer (low pH, liquid or frozen) that would prevent further formation of half molecules. The covalently bound intact monoclonal IgG4 antibodies are antibodies that possess two heavy chains and two light chains. IgG4 half molecules possess one heavy chain and one light chain. The half molecules are generated together with the intact molecules during production in mammalian cell and also in circulation. The half molecules is one of the main obstacles on the way of IgG4 subclass to commercial pharmaceuticals.

Human IgG4 antibody is a unique subclass of immunoglobulins gamma, because it possesses several unique features. First, it is unable to precipitate purified antigens [Aalberse and Schuurman, *Immunology* 2002, 105, 9-19; Schuurman et al., *Immunology* 1999, 97, 693-698.] This inability is caused by the inability of IgG4 antibodies to cross-link two antigens and start creating complexes. Human serum IgG4 are called functionally monovalent. Among all subclasses of immunoglobulins gamma, IgG4 reportedly posses only minimal (if any) ability to activate complement, as it can be seen from Table 1 adapted from [Jefferis and Lund, *Immunol. Lett.* 2002, 82, 57-65; Hulett and Hogarth, *Adv. Immunol.* 1994, 57, 1-127]. This unique feature makes IgG4 an attractive antibody candidate for the therapeutic applications, which require only binding to a ligand, and not creation of the complexes, which may lead to an undesirable immune response.

TABLE I

Human IgG-Fc recognition specificity for effector ligands

| IgG isotype | IgG1 | IgG2 | IgG3 | IgG4 |
| --- | --- | --- | --- | --- |
| Fc receptor expression: | | | | |
| FcγRI-monocytes, macrophages | +++ | − | ++++ | ++ |
| FcγRIIa-monocytes, macrophages, neutrophils, eosinophils, platelets | + | −† | ++ | − |
| FcγRIIb-B cells, monocytes, macrophages | ++ | ? | ++ | + |
| FcγRIIIa-macrophages, LGL, NK, γδ T cells | + | − | + | − |
| FcγRIIIb-neutrophils, eosinophils | + | − | + | − |
| FcRn-multiple cell types for catabolism | ++ | ++ | +? | ++ |
| placental cells for transport | +++ | ++ | ++ | ++ |
| Complement activation: | | | | |
| C1q-classical pathway | +++ | + | +++ | − |
| C3-alternate pathway | − | + | − | − |
| MBL-depending on glycosylation status | ++ | ++ | ++ | ++ |
| Products of microorganisms: | | | | |
| SpA-staphylycoccal protein A | ++ | ++ | − | ++ |
| SpG-streptococcal protein G | ++ | ++ | ++ | ++ |
| FcγR-encoded by herpes virus | ++ | ++ | − | ++ |

Updated from Ref. [4]. LGL, large granular lymphocytes; NK, natural killer cells; and †, depending on the allotype of FcγRIIa.

In addition, IgG4 molecules possess the following, second, unique property: IgG4 molecules undergo in vivo exchange of half molecules (HL) among IgG4 molecules [Aalberse and Schuurman, *Immunology* 2002, 105, 9-19]. This exchange is possible, because IgG4 molecules are made up of two non-covalently bound half molecules. In these IgG4 molecules, interchain disulfide bridges between the two heavy chains at the hinge region are shifted to form intrachain bridges. There have been reports that 25-75% fraction of the IgG4 molecules is bound only by the non-covalent interactions between the heavy chains. These IgG4 molecules are very stable under normal physiological conditions in vitro; because of the strong non-covalent interactions between the CH3 domains, and possibly CH1 and CH2 domains. It was suggested Aalberse and Schuurman, *Immunology* 2002, 105, 9-19], that the exchange is catalyzed in vivo by protein disulfide isomerase (PDI) and/or FcRn (the major histocompatibility complex (MHC)-related Fc receptor) during transit of IgG4 in the endosomal pathway in endothelial cells. It was also suggested that the inter-heavy chain disulfide bonds of IgG4 are in equilibrium with intra-chain disulfide bonds [Schuurman et al., *Mol. Immunol.* 2001, 38, 1-8].

This ability of non-covalently bound IgG4 antibodies to exchange halves is biologically relevant in situations in which high IgG4 responses are found against two unrelated antigens that happen to be present in the body at the same time and place Aalberse and Schuurman, *Immunology* 2002, 105, 9-19]. In such circumstances, antibody-antigen complexes can be formed causing an immunogenic response. This has been confirmed experimentally by Schuurman et al., [*Immunology* 1999, 97, 693-698], in studies which showed IgG4 cross-linking with two different antigens in serum from patients with IgG4 antibodies to both house dust mite and grass pollen. It was found that a large fraction of plasma IgG4 molecules had two different antigen-binding sites, resulting in the bispecificity. This feature represents a potential risk of injecting IgG4 molecules into patients, who suffer from allergies caused by house dust mite, grass pollen or bee sting and may have polyclonal or a second monoclonal IgG4. The inventors propose that the observations from [Aalberse and Schuurman, *Immunology* 2002, 105, 9-19; Schuurman et al., *Immunology* 1999, 97, 693-698.] suggest that IgG4 half-molecules are undesirable species for pharmaceutical applications, because they can form bispecific antibodies and have a shorter life-time in circulation [Angal et al., Mol. Immunol. 1993, 30, 105-108]. Indeed in the selection for a therapeutic for clinical development an IgG4 moiety has been considered but thought undesirable because of the possibility of bispecificity, which can be caused by exchange of half molecules of the specific therapeutic IgG4 with other IgG4 half molecules that may be present in circulation.

Angal and coworkers mutated the serine in the hinge motif—CPSC— to a proline (which is found at that position in IgG1 and IgG2) in a mouse/human chimeric heavy chain of IgG4 [Angal et al., Mol. Immunol. 1993, 30, 105-108]. This single residue mutation lead to the production of a homogeneous homodimer IgG4 antibody. The single point mutation led to a significantly extended serum half-life and an improved tissue distribution as, compared to the original chimeric IgG4.

Figure 38:
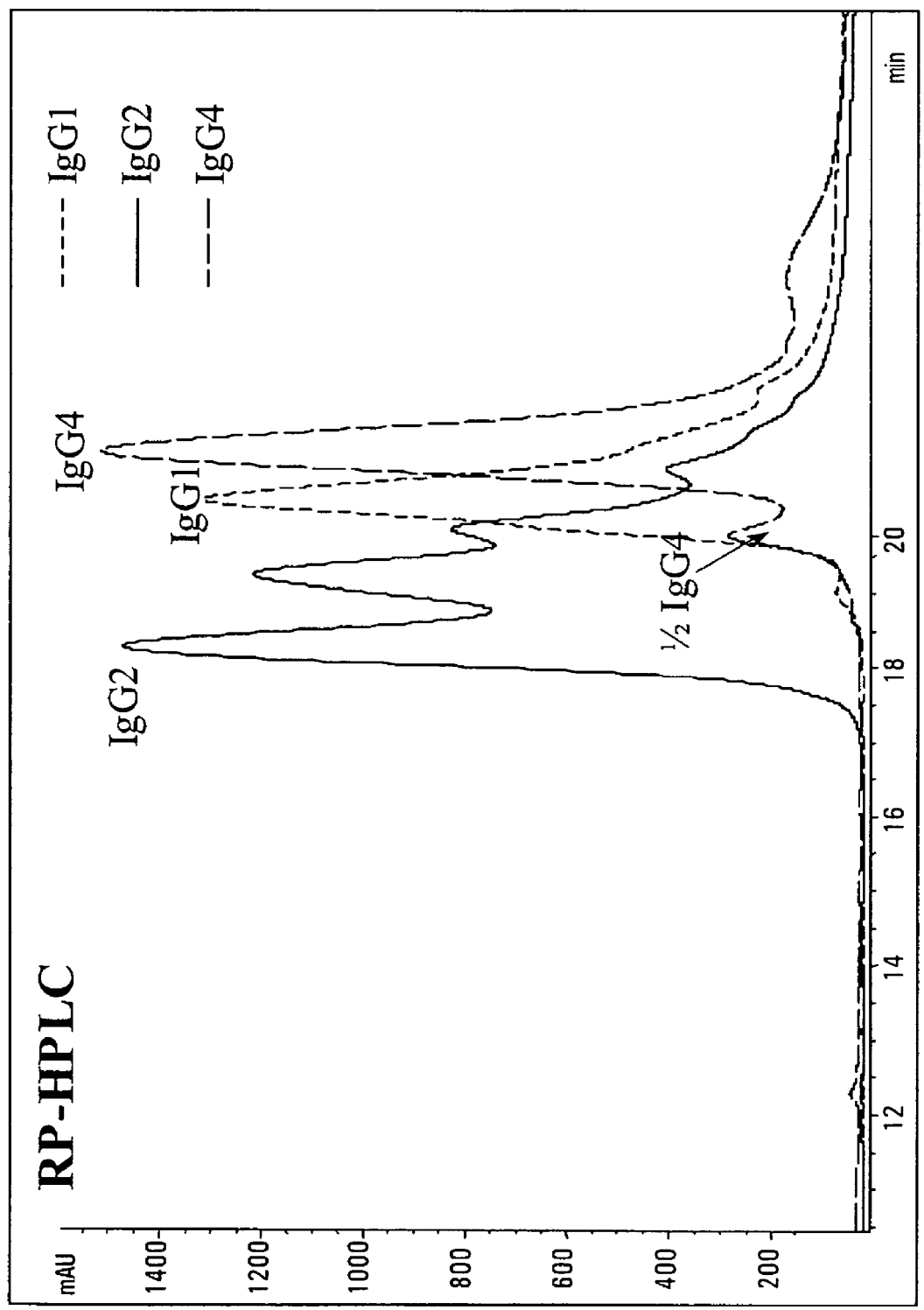
FIG. 38. Reversed-phase (RP) chromatograms of thee antibodies with the same CDRs implemented as IgG1, IgG2 and IgG4 modalities. IgG2 antibody shows multiple peaks due to the previously reported structural heterogeneity. IgG4 is also structurally heterogeneous. Under the denaturing PR conditions, the half molecule (½ IgG4) was separated from the covalently bound IgG4 molecule (IgG4).
Figure 39A:
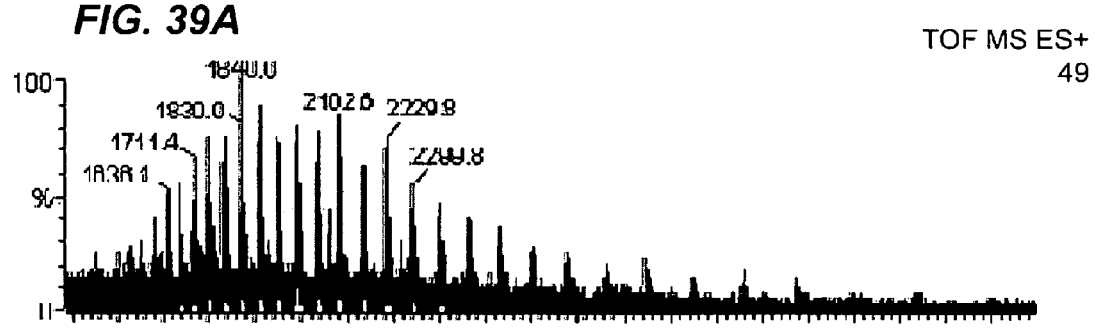
FIG. 39. Electrospray ionization (ESI) mass spectra of half molecule of IgG4 (A) and covalently bound IgG4 (B). Deconvoluted ESI mass spectra of half molecule of IgG4 (C) and covalently bound IgG4 (D). The accurate mass measurements indicate that mass of ½ IgG4 (73,398 Da) is exactly half of IgG4 (146,796 Da), suggesting that disulfide bond shifting lead to the formation of half molecules. The disulfide bond shift from interchain to intrachain should theoretically generate a half molecule with exactly the half mass, which was experimentally observed in this assay.
Figure 39B:
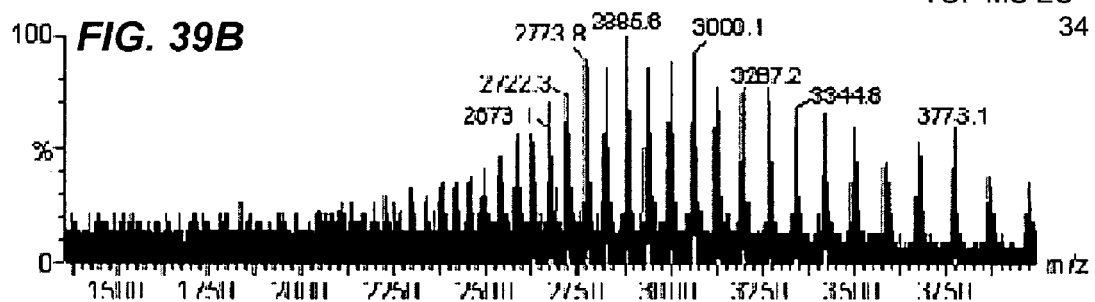
Figure 39C:
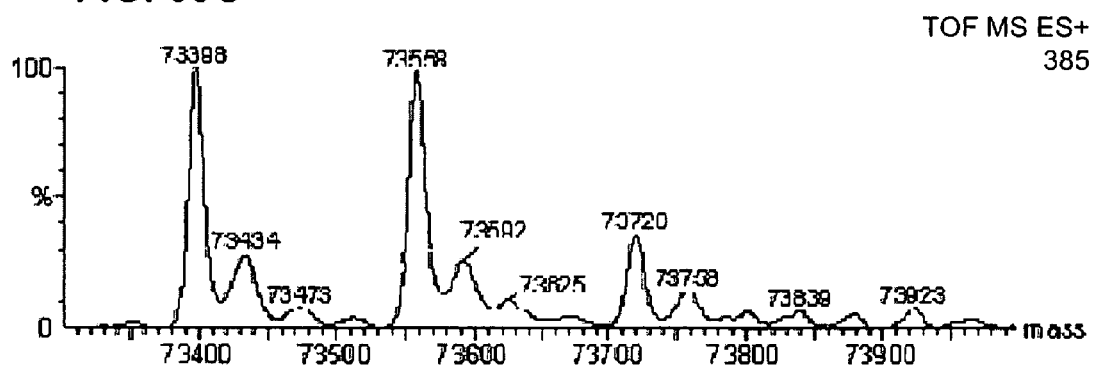
Figure 39D:
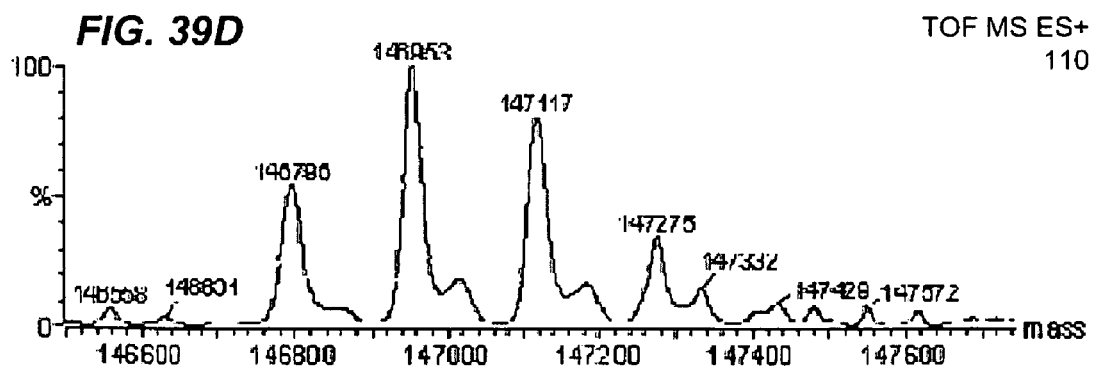

Given the above observations and the teachings of the present invention with respect to refolding of IgG1 and IgG2 molecules, it is proposed that a heterogeneous population IgG4 molecules that contains IgG4 half molecules as well as intact IgG4 molecules can be enriched for covalently bound intact monoclonal IgG4 antibodies by refolding the half molecules into the covalently bound intact molecules IgG4 antibodies. The monoclonal IgG4 produced in mammalian cells and containing half-molecules and covalently bound molecules will be contacted with reduction-oxidation reagents in the presence of a denaturing reagent to produce predominantly IgG4 homodimer molecules. After performing the redox treatment, the antibody should be able to be formulated in a stable buffer (low pH, liquid or frozen) that would prevent further half-mers from forming. FIG. 38 and FIG. 39 below details of a reversed phase LC/MS analysis of an IgG4 antibody, which was used to separate and identify half IgG4 molecules and intact IgG4 molecules.

Given these finding, it is suggested that the refolding experiments described above for IgG1 and IgG2 molecules could be adapted to produce appropriate refolding of IgG4 molecules in like manner to the refolding seen for IgG1 and IgG2.

Example 10

Refolding Antibodies for Improved Crystallization Properties

Another area in which the methods of the present invention are useful is in the area of formation of antibody crystals. The development of antibody crystallization has been limited by the heterogeneity of these large macromolecules with respect to conformation, disulfide connectivity, glycovariants, and charge variants. Crystallization of IgG molecules has been primarily limited to the Fab fragment, Fc fragment, complexation of fragments with the ligand or Fc receptor, intact IgG1, and intact murine IgG2a (not intact human IgG2). Previous patents on intact antibody crystallization describe spherical nanocrystalline composite protein particles and crystalline formulations [Altus WO0272636 (A2, A3) and WO0300014 (A2)] that have been successful only in limited cases of therapeutic IgG1 antibodies, namely Infliximab (Remicade), Rituximab (Rituxan), and Trastuzumab (Herceptin).

Recent analytical advancements in reversed-phase HPLC analysis of high molecular weight proteins have revealed disulfide heterogeneity of IgG2 antibodies [Dillon et al., U.S. Provisional Application 60/621,295 and PCT/US05/001840]. Methods of refold proteins by the addition of reduction/oxidation (redox) agents to facilitate the formation of native-like disulfide bonds, resulting in a structurally homogeneous, active form of the molecule for improved pharmaceutical properties have been described above. In the present Example, data are provided on the application of refolding antibodies for improved crystallization properties.

As described in PCT/US05/001840 and U.S. Provisional Application 60/621,295, one aspect of the invention involves introducing or optimizing components of the fermentation media, including nutrients such as cysteine, cystine, cystamine, glutathione, copper, and/or other oxidizing reagents and different buffer compositions such that the appropriate redox potential is achieved for refolding of the product secreted into the media A second aspect is to introduce a separate processing step for oxidative refolding of the protein, differing from typical microbial refolding of inclusion bodies. A third aspect of the invention is to introduce the redox agents directly into crystallization solutions, such that misfolded protein can refold in solution and attach to the growing crystal, resulting in improved crystallization yields.

Data provided in the present Example demonstrate successful crystallization of refolded intact IgG2. Refolding of IgG1 to remove cysteinylation has also demonstrated improved activity and homogeneity [see Examples above], and crystallization studies are in progress to demonstrate refolding IgG1 results in improved crystallization properties for that subclass. By refolding during the fermentation, in a separate processing step, or within the crystallization solution, it is possible to generate product with improved pharmaceutical and crystallization properties, including improved homogeneity, activity/potency, stability, crystal growth, and crystallization yields.

In the initial screens, crystals were obtained in the following conditions, using refolded anti IL-1R IgG2 antibody at 50 mg/mL. Anti IL-1R IgG2 antibody was refolded in the presence of denaturant to populate form 3, as described above.

1. 50 mM potassium chloride, 20% PEG 3350 pH 2.0
2. 50 mM potassium chloride, 24% PEG 3350 pH 2.0
3. 50 mM MES, 20% PEG 3350 pH 6.0
5.0 mM MES, 24% PEG 3350 pH 6.0
6. 1.13M Na—K phosphate, 0.1M Na cacodylate pH 5.5, 0.69% MEGA-7* (a sugar-based detergent obtained from Anatrace)
7. 2.12M sodium acetate, 0.65% MEGA-7* (a sugar-based detergent obtained from Anatrace).

Figure 40:
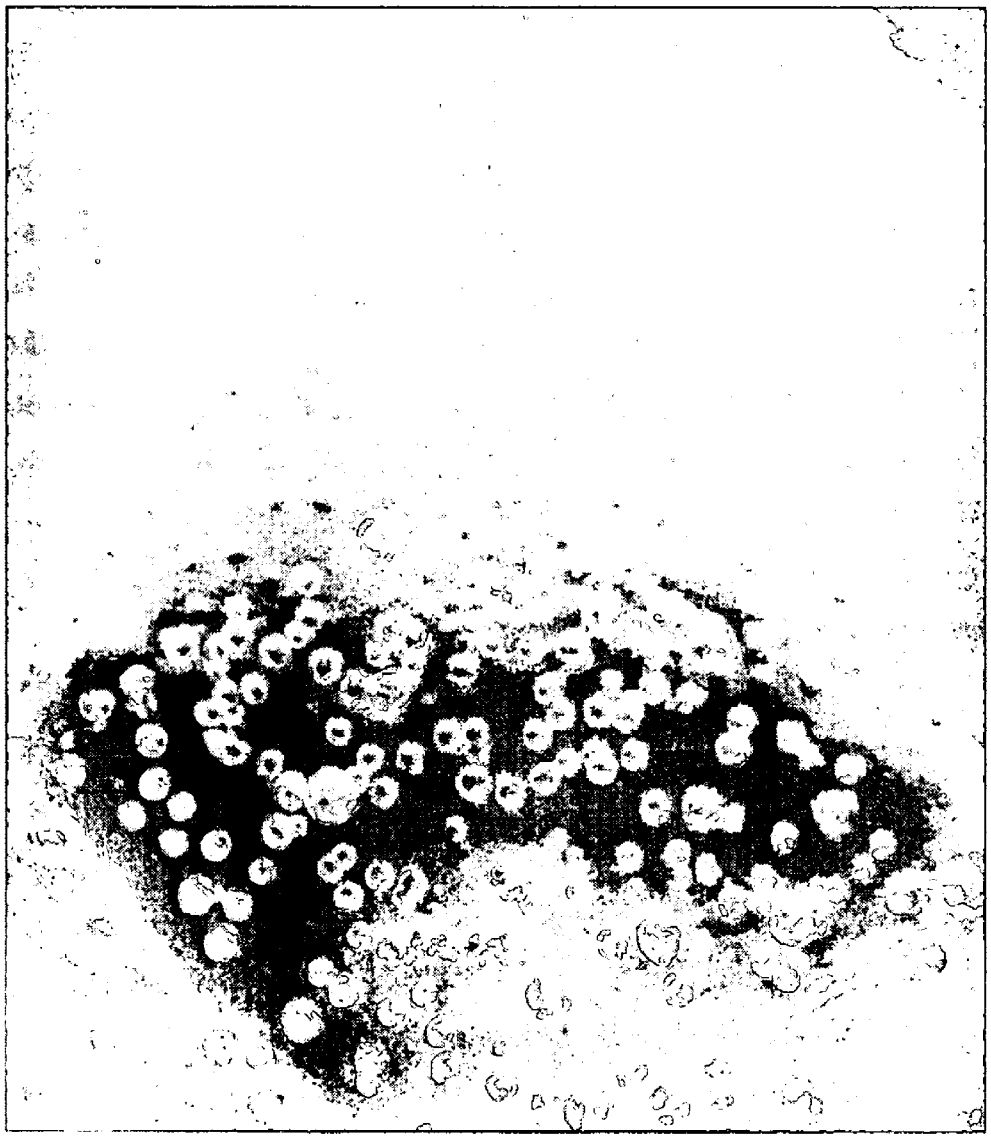
FIG. 40. Photograph of IgG2 crystals formed under conditions of: 50 mg/mL IgG2, 50 mM Potassium Chloride pH 2.0, 20% PEG 3350.
Figure 41:
FIG. 41. Photograph of IgG2 crystals formed under conditions of: 50 mg/mL IgG2, 50 mM Potassium Chloride pH 2.0, 24% PEG 3350.
Figure 42:
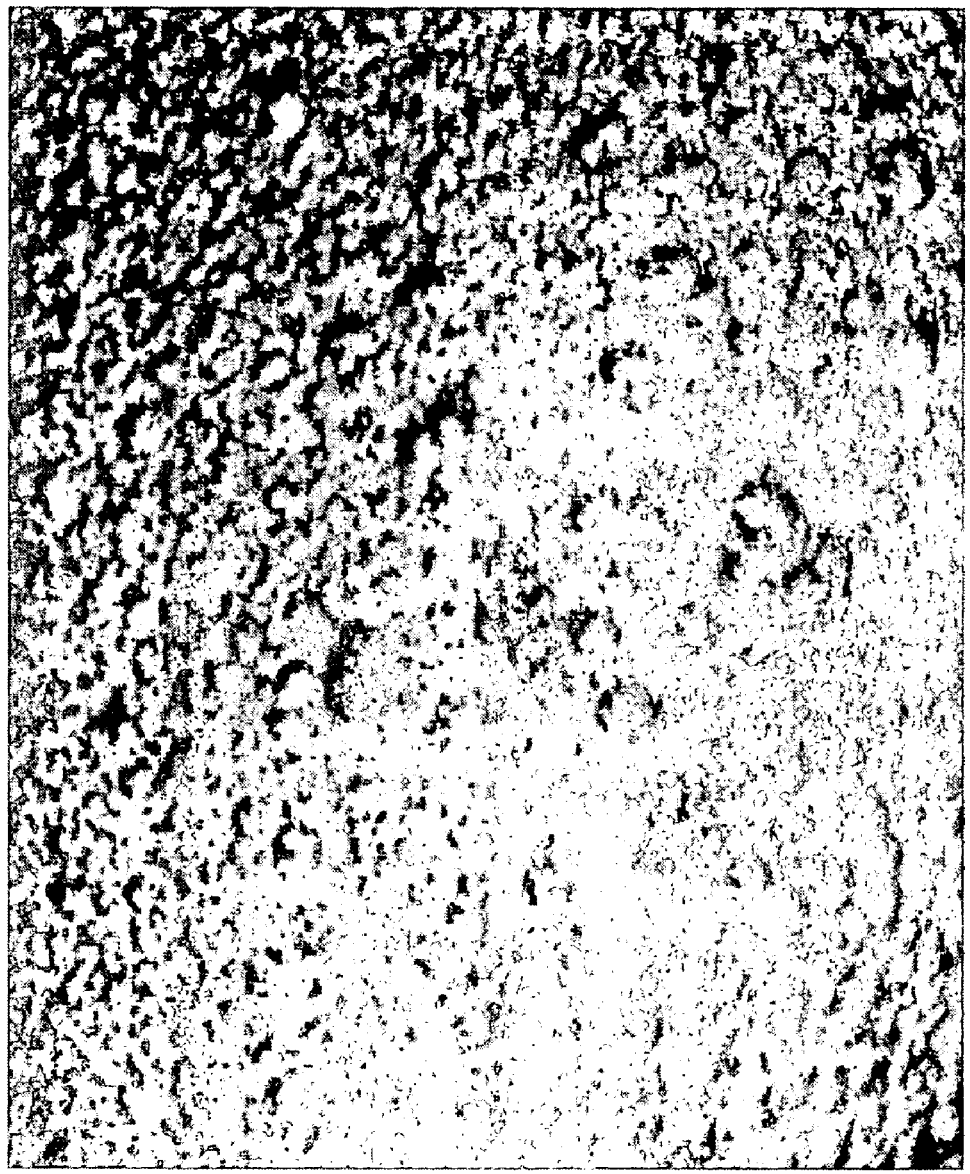
FIG. 42. Photograph of IgG2 crystals formed under conditions of: 50 mg/mL IgG2, 50 mM MES pH 6.0, 20% PEG 3350.

The data, shown in FIGS. 40-42 show that the IgG2 crystals formed under the conditions above were spherical crystals, demonstrating that the methods of the invention provide a homogeneous preparation of the IgG to allow formation of uniform crystals of intact antibodies.

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. A method of producing an IgG2 antibody preparation enriched for one of several IgG2 structural variants which differ by disulfide connectivity in the hinge region, comprising contacting a preparation of an IgG2 antibody that has been recombinantly produced by mammalian cells with a reduction/oxidation coupling reagent at a pH of about 5 to about 11 in the absence of or the presence of a chaotropic agent, wherein (i) said IgG2 antibody to be subjected to the method elutes as several separate forms, corresponding to said several IgG2 structural variants, on RP-HPLC, (ii) said contacting in the absence of a chaotropic agent enriches one of said several IgG2 structural variants, and (iii) said contacting in the presence of a chaotropic agent enriches another of said several IgG2 structural variants.

2. The method of claim 1, wherein the pH of said reduction/oxidation coupling reagent is from about 5 to about 10.

3. The method of claim 1, wherein the pH of said reduction/oxidation coupling reagent is from about 7.6 to about 9.6.

4. The method of claim 1, wherein the pH of said reduction/oxidation coupling reagent is about 8.6.

5. The method of claim 1, wherein the reduction/oxidation coupling reagent-comprises reduced glutathione and oxidized glutathione.

6. The method of claim 5, wherein the ratio of reduced glutathione to oxidized glutathione is about 1:1 to about 100:1.

7. The method of claim 1, wherein the reduction/oxidation coupling reagent comprises cysteine/cystine.

8. The method of claim 7, wherein the cysteine/cystine comprises from about 0.1 mM to about 10 mM cysteine.

9. The method of claim 7, wherein the cysteine/cystine is present in a cysteine:cystine ratio of about 1:1 to about 10:1.

10. The method of claim 7, wherein the cysteine/cystine comprises about 6 mM cysteine and about 1 mM cystine.

11. The method of claim 7, wherein the cysteine/cystine comprises about 6 mM cysteine and about 6 mM cystine.

12. The method of claim 7, wherein the contacting step is performed for at least 30 minutes.

13. The method of claim 12, wherein the contacting step is performed for about 4 to about 48 hours.

14. The method of claim 1, wherein the redox coupling reagent comprises from about 0.1 mM to about 10 mM cystine and no exogenous cysteine is added.

15. The method of claim 1, wherein said recombinant IgG2 antibody is purified prior to said contacting.

16. The method of claim 1, wherein said recombinant IgG2 antibody is partially purified prior to said contacting.

17. The method of claim 1, further comprising contacting the contacted recombinant IgG2 antibody with a further composition comprising a second reduction/oxidation coupling reagent.

18. The method of claim 1, wherein the concentration of the recombinant IgG2 antibody is from about 1 mg/ml to about 50 mg/ml.

19. The method of claim 1, wherein said contacting produces a IgG2 antibody which is more stable in storage than the same IgG2 antibody that is not contacted.

20. The method of claim 1, wherein said contacting produces a IgG2 antibody which is more thermally stable than the same IgG2 antibody that is not contacted.

21. The method of claim 1, wherein said contacting produces a IgG2 antibody which has an improved crystallization property compared to the same IgG2 antibody that is not contacted.

22. The method of claim 1, wherein said contacting produces a IgG2 antibody population which is more homogeneous than the same IgG2 antibody population that is not contacted.

23. The method of claim 1, wherein said contacting occurs in the presence of a chaotropic agent before, after or concurrently with said contacting with said reduction/oxidation coupling reagent.

24. The method of claim 23, wherein said chaotropic agent is selected from the group consisting of urea, arginine, SDS and guanidine hydrochloride.

25. The method of claim 24, wherein said chaotropic agent comprises guanidine hydrochloride.

26. The method of claim 25, wherein the concentration of guanidine hydrochloride is from about 0.1 M to about 1.5 M.

27. The method of claim 25, wherein the concentration of guanidine hydrochloride is from about 0.1 M to about 1 M.

28. The method of claim 25, wherein the concentration of guanidine hydrochloride is about 0.5M.

29. The method of claim 25, wherein the concentration of guanidine hydrochloride is about 0.9M.

30. The method of claim 1, further comprising formulating the IgG2 antibody as produced by said method into a sterile bulk form.

31. The method of claim 1, further comprising formulating the IgG2 antibody as produced by said method into a sterile unit dose form.

32. The method of claim 1, further comprising isolating one of said several IgG2 structural variants.

33. The method of claim 32, wherein the procedure for said isolating is selected from the group consisting of reversed-phase chromatography HPLC, size-exclusion chromatography, ion-exchange chromatography, hydrophobic interaction chromatography, affinity chromatography and electrophoresis.

34. The method of claim 32, wherein the procedure for said isolating is ion-exchange chromatography.

35. The method of claim 1, wherein said recombinant IgG2 antibody is attached to a stationary phase of a chromatographic column and a reduction/oxidation coupling reagent is a part of the mobile phase.

36. The method of claim 1, wherein said reduction/oxidation coupling reagent is an enzyme.

37. The method or claim 1, wherein said reduction/oxidation coupling reagent includes bivalent metal ions and oxygen.

38. The method of claim 1 wherein prior to said method said IgG2 antibody is isolated from the culture medium of mammalian cells in a method comprising:

culturing a mammalian cell that expresses and secretes into culture medium an IgG2 antibody or an IgG2 antibody fragment;

adding a reduction/oxidation coupling reagent at a pH of about 5 to about 11; and, isolating said antibody.

39. The method of claim 1 or claim 38, further comprising purifying the antibody, wherein the purifying comprises one or more chromatography steps.

40. A method of producing a recombinant IgG2 antibody, or an IgG2 antibody fragment comprising:

contacting an IgG2 antibody or an IgG2 antibody fragment that has been recombinantly produced by mammalian cells with a reduction/oxidation coupling reagent at a pH of about 5 to about 11 in the absence of or the presence of a chaotropic agent;

wherein (i) said IgG2 antibody to be subjected to the method elutes as several separate forms on RP-HPLC which differ by disulfide connectivity in the hinge region (ii) said contacting in the absence of a chaotropic agent enriches one of said several separate forms, and (iii) said contacting in the presence of a chaotropic agent enriches another of said several separate forms.

41. The method of claim 40, wherein prior to said method said IgG2 antibody or IgG2 antibody fragment is isolated from the culture medium of mammalian cells in a method comprising culturing a mammalian cell that expresses and secretes into culture medium an IgG2 antibody or an IgG2 antibody fragment; adding reduction/oxidation coupling reagent at a pH of about 5 to about 11 upon secretion of antibody from said cell.

42. The method of claim 40, wherein said contacting occurs in the presence of a chaotropic agent belbre, after or concurrently with said contacting with said reduction/oxidation coupling reagent.

43. A method of preparing a crystallized form of an intact recombinant IgG2 antibody comprising performing the method of claim 1 or claim 40;

and preparing a crystallized form of said recombinant IgG2 antibody.

44. The method of claim 43, wherein the recombinant IgG2 antibody is isolated after performing the method and prior to crystallizing said antibody.

* * * * *

UNITED STATES PATENT AND TRADEMARK OFFICE
CERTIFICATE OF CORRECTION

PATENT NO.        : 7,928,205 B2  
APPLICATION NO.   : 11/255528  
DATED             : April 19, 2011  
INVENTOR(S)       : Thomas Dillon et al.

Page 1 of 1

It is certified that error appears in the above-identified patent and that said Letters Patent is hereby corrected as shown below:

Column 60, line 49, "or" should be --of--.
Column 62, line 5, "belbre" should be --before--.

Signed and Sealed this
Twenty-seventh Day of September, 2011

David J. Kappos
*Director of the United States Patent and Trademark Office*